(12) United States Patent
He et al.

(10) Patent No.: US 9,242,998 B2
(45) Date of Patent: Jan. 26, 2016

(54) TETRACYCLIC HETEROCYCLE COMPOUNDS AND METHODS OF USE THEREOF FOR THE TREATMENT OF HEPATITIS C

(71) Applicants: Shuwen He, Fanwood, NJ (US); Xing Dai, Cranford, NJ (US); Anandan Palani, Bridgewater, NJ (US); Ravi Nargund, East Brunswick, NJ (US); Zhong Lai, East Brunswick, NJ (US); Nicolas Zorn, Durmenach (FR); Dong Xiao, Warren, NJ (US); Qun Dang, Westfield, NJ (US); Casey C. McComas, Pheonixville, PA (US); Peng Li, Shanghai (CN); Xuanjia Peng, Shanghai (CN); Richard Soll, Shanghai (CN)

(72) Inventors: Shuwen He, Fanwood, NJ (US); Xing Dai, Cranford, NJ (US); Anandan Palani, Bridgewater, NJ (US); Ravi Nargund, East Brunswick, NJ (US); Zhong Lai, East Brunswick, NJ (US); Nicolas Zorn, Durmenach (FR); Dong Xiao, Warren, NJ (US); Qun Dang, Westfield, NJ (US); Casey C. McComas, Pheonixville, PA (US); Peng Li, Shanghai (CN); Xuanjia Peng, Shanghai (CN); Richard Soll, Shanghai (CN)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/766,491

(22) PCT Filed: Feb. 3, 2014

(86) PCT No.: PCT/US2014/014365
§ 371 (c)(1),
(2) Date: Aug. 7, 2015

(87) PCT Pub. No.: WO2014/123795
PCT Pub. Date: Aug. 14, 2014

(65) Prior Publication Data
US 2015/0368265 A1     Dec. 24, 2015

(30) Foreign Application Priority Data
Feb. 7, 2013  (CN) ................. PCT/CN2013/000130

(51) Int. Cl.
*C07D 498/14* (2006.01)
*A61K 31/5365* (2006.01)
*A61K 31/5377* (2006.01)
*A61K 45/06* (2006.01)

(52) U.S. Cl.
CPC .......... *C07D 498/14* (2013.01); *A61K 31/5365* (2013.01); *A61K 31/5377* (2013.01); *A61K 45/06* (2013.01)

(58) Field of Classification Search
CPC ............. C07D 498/14; A61K 31/5365; A61K 31/5377
USPC ........................................ 514/229.5; 544/95
See application file for complete search history.

(56) References Cited

U.S. PATENT DOCUMENTS

| | | | |
|---|---|---|---|
| 6,777,392 B2 | 8/2004 | Maurya et al. |
| 7,105,499 B2 | 9/2006 | Carroll et al. |
| 7,112,600 B1 | 9/2006 | Hashimoto et al. |
| 7,125,855 B2 | 10/2006 | Bhat et al. |
| 7,202,224 B2 | 4/2007 | Eldrup et al. |
| 2003/0203948 A1 | 10/2003 | Fujishita et al. |
| 2004/0067901 A1 | 4/2004 | Bhat et al. |
| 2004/0110717 A1 | 6/2004 | Carroll et al. |
| 2006/0100262 A1 | 5/2006 | Conte et al. |
| 2009/0048239 A1 | 2/2009 | Conte et al. |
| 2012/0083483 A1 | 4/2012 | Coburn et al. |
| 2012/0328569 A1 | 12/2012 | McComas et al. |

FOREIGN PATENT DOCUMENTS

| | | |
|---|---|---|
| WO | WO0147883 | 7/2001 |
| WO | WO0177091 | 10/2001 |
| WO | WO0204425 | 1/2002 |
| WO | WO0206246 | 1/2002 |
| WO | WO0220497 | 3/2002 |
| WO | WO02057287 | 7/2002 |
| WO | WO02057425 | 7/2002 |
| WO | WO03068244 | 8/2003 |
| WO | WO2004000858 | 12/2003 |

(Continued)

OTHER PUBLICATIONS

Carroll et al., Inhibition of Hepatitis C Virus RNA Replication by 2'-Modified Nucleoside Analogs, J. Biol. Chem., 2003, 11979-11984, 278(14).

*Primary Examiner* — Kahsay Habte
(74) *Attorney, Agent, or Firm* — Anna L. Cocuzzo; Alysia A. Finnegan

(57) ABSTRACT

The present invention relates to compounds of formula (I) that are useful as hepatitis C virus (HCV) NS5B polymerase inhibitors, the synthesis of such compounds, and the use of such compounds for inhibiting HCV NS5B polymerase activity, for treating or preventing HCV infections and for inhibiting HCV viral replication and/or viral production in a cell-based system.

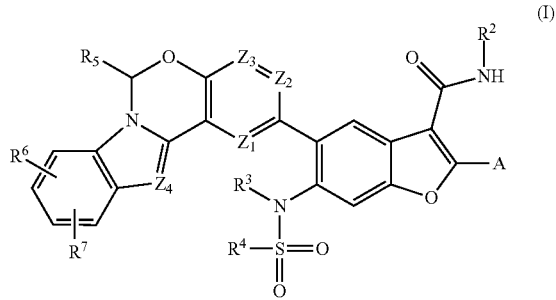

17 Claims, No Drawings

(56) References Cited

FOREIGN PATENT DOCUMENTS

| WO | WO2004003138 | 1/2004 |
|---|---|---|
| WO | WO2004007512 | 1/2004 |
| WO | WO2004041201 | 5/2004 |
| WO | WO2005003147 | 1/2005 |
| WO | WO2005016927 | 2/2005 |
| WO | WO2006020082 | 2/2006 |
| WO | WO2006066079 | 6/2006 |
| WO | WO2006066080 | 6/2006 |
| WO | WO2008075103 | 6/2008 |
| WO | WO2009010783 | 1/2009 |
| WO | WO2009010785 | 1/2009 |
| WO | WO2011106992 | 9/2011 |
| WO | WO 2011106992 A1 * | 9/2011 |
| WO | WO2012041014 | 4/2012 |
| WO | WO2013033900 | 3/2013 |
| WO | WO2013033971 | 3/2013 |
| WO | WO2014123793 | 8/2014 |
| WO | WO2014123794 | 8/2014 |

* cited by examiner

TETRACYCLIC HETEROCYCLE COMPOUNDS AND METHODS OF USE THEREOF FOR THE TREATMENT OF HEPATITIS C

FIELD OF THE INVENTION

The present disclosure relates to antiviral compounds that are useful as inhibitors of the hepatitis C virus (HCV) NS5B (non-structural protein 5B) polymerase, compositions comprising such compounds, the use of such compounds for treating HCV infection and/or reducing the likelihood or severity of symptoms of HCV infection, methods for inhibiting the function of the NS5B polymerase, and methods for inhibiting HCV viral replication and/or viral production.

CROSS-REFERENCE TO RELATED APPLICATIONS

This application is a §371 National Stage Application of PCT/US2014/014365, international filing date of Feb. 3, 2014, which claims the benefit of International Application No. PCT/CN2013/000130, filed Feb. 7, 2013, now expired.

BACKGROUND OF THE INVENTION

Hepatitis C virus (HCV) infection is a major health problem that leads to chronic liver disease, such as cirrhosis and hepatocellular carcinoma, in a substantial number of infected individuals. Current treatments for HCV infection include immunotherapy with recombinant interferon-α alone or in combination with the nucleoside analog ribavirin.

Several virally-encoded enzymes are putative targets for therapeutic intervention, including a metalloprotease (NS2-3), a serine protease (NS3, amino acid residues 1-180), a helicase (NS3, full length), an NS3 protease cofactor (NS4A), a membrane protein (NS4B), a zinc metalloprotein (NS5A) and an RNA-dependent RNA polymerase (NS5B).

One identified target for therapeutic intervention is HCV NS5B polymerase. Sven-Erik Behrens et al., *Identification and properties of the RNA-dependent RNA polymerase of hepatitis C virus*, 15(1) EMBO J. 12-22 (1996). Antagonists of NS5B activity are inhibitors of HCV replication. Steven S. Carroll et al., *Inhibition of Hepatitis C Virus RNA Replication by 2'-Modified Nucleoside Analogs*, 278(14) J. BIOL. CHEM. 11979-84 (2003).

There is a clear and long-felt need to develop effective therapeutics for treatment of HCV infection. Specifically, there is a need to develop compounds that selectively inhibit HCV viral replication and that would be useful for treating HCV-infected patients.

SUMMARY OF THE INVENTION

The present disclosure relates to novel compounds of formula I and/or pharmaceutically acceptable salts thereof. These compounds are useful, either as compounds or their pharmaceutically acceptable salts (when appropriate), in the inhibition of HCV (hepatitis C virus) NS5B (non-structural 5B) polymerase, the prevention or treatment of one or more of the symptoms of HCV infection, the inhibition of HCV viral replication and/or HCV viral production, and/or as pharmaceutical composition ingredients. As pharmaceutical composition ingredients, these compounds and their salts may be the primary active therapeutic agent, and, when appropriate, may be combined with other therapeutic agents including but not limited to other HCV antivirals, anti-infectives, immuno-modulators, antibiotics or vaccines, as well as the present Standard of Care treatment options for HCV.

In one aspect, the present invention relates to a compound of formula I:

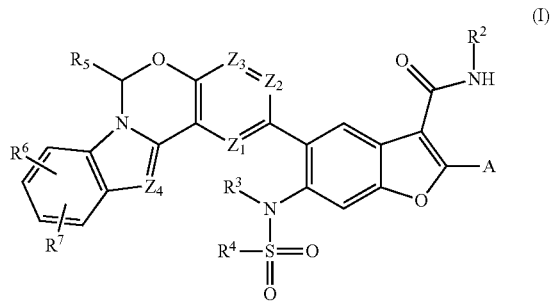

or a pharmaceutically acceptable salt thereof,
wherein:
$Z_1$, $Z_2$ and $Z_3$ are independently CH or N;
$Z_4$ is CH or N;
A is $C_3$-$C_6$ cycloalkyl, $C_2$-$C_4$ alkenyl, $C_3$-$C_6$ cycloalkenyl, 4- to 6-membered monocyclic heterocycloalkyl, 4- to 6-membered monocyclic heterocycloalkenyl, —C(=O)NR$^a$R$^b$, —C(=O)— (4- to 6-membered monocyclic heterocycloalkyl), —C(R$^c$)=NOR$^d$, or HetA, wherein cycloalkyl is optionally substituted by 1 or 2 substituents selected from $C_1$-$C_6$ alkyl and halo, wherein HetA is optionally substituted by 1 or 2 ring substituents $R^1$, and wherein the 4- to 6-membered monocyclic heterocycloalkyl is optionally substituted with oxo;

HetA is a 5- or 6-membered aromatic monocyclic ring with 1, 2 or 3 heteroatom ring atoms independently selected from N, O and S;

$R^a$, $R^b$, $R^c$, $R^d$ are independently selected from H and $C_1$-$C_6$ alkyl;

each occurrence of $R^1$ is independently selected from halo, —OH, $C_1$-$C_6$ alkyl, $C_1$-$C_6$ alkoxy, $C_1$-$C_6$ haloalkyl, —O—($C_1$-$C_6$ alkyl), —O—($C_1$-$C_6$ haloalkyl), oxo, cyano, and —O— phenyl-F;

$R^2$ is hydrogen, $C_1$-$C_6$ alkyl or —O($C_1$-$C_6$ alkyl);
$R^3$ is hydrogen or $C_1$-$C_6$ alkyl;
$R^4$ is $C_1$-$C_6$ alkyl or —O($C_1$-$C_6$ alkyl);
$R^5$ is hydrogen or $C_1$-$C_6$ hydroxyalkyl; and
$R^6$ and $R^7$ are independently hydrogen, halo, cyano or $C_1$-$C_4$ alkyl.

The present invention also includes pharmaceutical compositions containing a compound of the present invention and methods of preparing such pharmaceutical compositions. The present invention further includes methods of treating or reducing the likelihood or severity of HCV infection, methods for inhibiting the activity of the NS5B polymerase, and methods for inhibiting HCV viral replication and/or viral production.

Other embodiments, aspects and features of the present invention are either further described in or will be apparent from the ensuing description, examples and appended claims.

DETAILED DESCRIPTION OF THE INVENTION

The present invention includes compounds of formula I above, and pharmaceutically acceptable salts thereof. The compounds of formula I are HCV NS5B polymerase inhibitors.

In an aspect of the invention, at least one of $Z_1$, $Z_2$ and $Z_3$ is N.

In a first embodiment of the invention, $R^2$ and $R^4$ are independently $C_1$-$C_6$ alkyl. In this embodiment, all other groups are as provided in the general formula above or as in the first aspect.

In a second embodiment of the invention, $R^2$, $R^3$ and $R^4$ are methyl. In this embodiment, all other groups are as provided in the general formula above, as in the first aspect as in the first embodiment.

In a third embodiment of the invention, no more than one of $R^6$ and $R^7$ are halo. In all aspects of this embodiment, all other groups are as provided in the general formula above, as in the first aspect or as in the first or second embodiments.

In a fourth embodiment of the invention, each halo is F. In this embodiment, all other groups are as provided in the general formula above, as in the first aspect or as in the first through third embodiments.

In a fifth embodiment of the invention, $R^5$ is hydrogen or —$CH_2OH$. In this embodiment, all other groups are as provided in the general formula above, as in the first aspect or as in the first through fourth embodiments.

In a sixth embodiment of the invention, the compound of the invention has the formula:

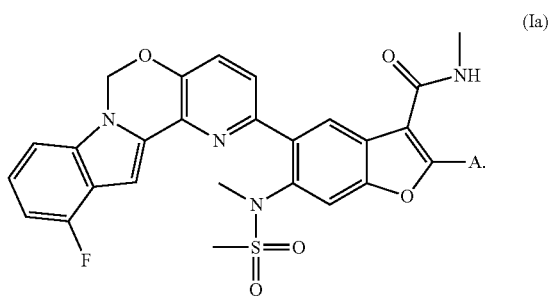

(Ia)

In this embodiment, all other groups are as provided in the general formula above, as in the first aspect or as in the first through fifth embodiments.

In a seventh embodiment of the invention, A is $C_3$-$C_6$ cycloalkyl, $C_2$-$C_4$ alkenyl, $C_3$-$C_6$ cycloalkeny, 4- to 6-membered monocyclic heterocycloalkyl, 4- to 6-membered monocyclic heterocycloalkenyl (optionally substituted with 1 or 2 substituents independently selected from $C_1$-$C_6$ alkyl, $C_1$-$C_6$ alkoxy, $C_1$-$C_6$ haloalkyl, oxo, halo, and —O—$C_1$-$C_6$ haloalkyl), 5-6 membered aromatic monocyclic ring with 1, 2 or 3 heteroatom ring atoms selected from N, O, and S (optionally substituted with 1 or 2 substituents independently selected from $C_1$-$C_6$ alkyl, $C_1$-$C_6$ alkoxy, $C_1$-$C_6$ haloalkyl, oxo, halo, —O-4-F-phenyl, and —O—$C_1$-$C_6$ haloalkyl). In an aspect of this seventh embodiment, A is cyclopropyl,

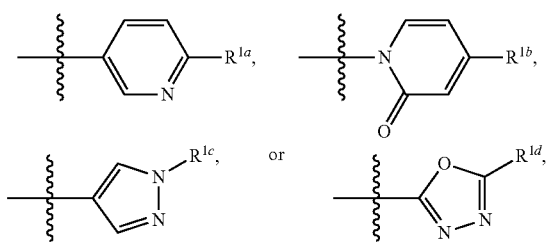

wherein $R^{1a}$ is F, methyl, ethyl, methoxy, ethoxy, —O-isopropyl, —$OCHF_2$, —$OCH_2CF_3$, —$CHF_2$, or —$CF_3$, $R^{1b}$ is hydrogen or methyl, $R^{1c}$ is methyl, ethyl, or isopropyl, and $R^{1d}$ is methyl or ethyl. In another aspect of this embodiment, A is cyclopropyl,

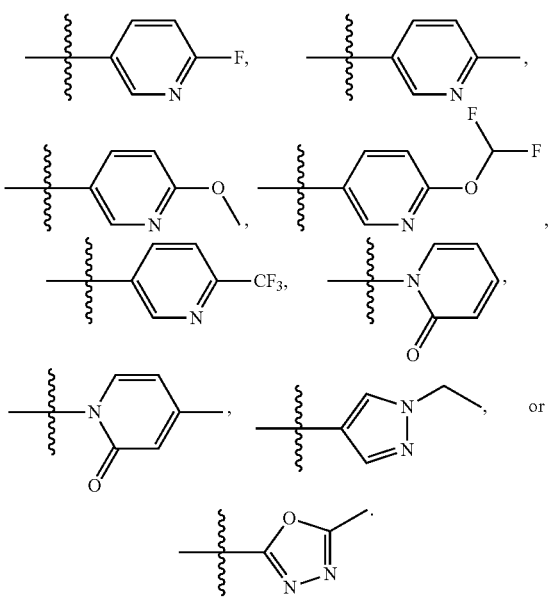

In all aspects of this embodiment, all other groups are as provided in the general formula above, as in the first aspect or as in the first through sixth embodiments.

In another embodiment of the invention, the compound of the invention is selected from the exemplary species depicted in Examples 1-7, 9-27, 30-32 and 34-59 shown below, and pharmaceutically acceptable salts thereof.

In another embodiment of the invention, the compound of the invention is selected from the exemplary species depicted in Examples 2, 4, 7, 11, 14, 25, 35, 37, 38 and 59 shown below, and pharmaceutically acceptable salts thereof.

Other embodiments of the present invention include the following:

(a) A pharmaceutical composition comprising an effective amount of a compound of formula I and a pharmaceutically acceptable carrier.

(b) The pharmaceutical composition of (a), further comprising a second therapeutic agent selected from the group consisting of HCV antiviral agents, immunomodulators, and anti-infective agents.

(c) The pharmaceutical composition of (b), wherein the HCV antiviral agent is an antiviral selected from the group consisting of direct inhibitors of HCV, including but not limited to NS3 and NS3/4A protease inhibitors, NS5A inhibitors and HCV NS5B polymerase inhibitors.

(d) A pharmaceutical combination that is (i) a compound of formula I and (ii) a second therapeutic agent selected from the group consisting of HCV antiviral agents, immunomodulators, and anti-infective agents; wherein the compound of formula I and the second therapeutic agent are each employed in an amount that renders the combination effective for inhibiting HCV NS5B activity, or for inhibiting HCV viral replication, or for treating HCV infection and/or reducing the likelihood or severity of symptoms of HCV infection.

(e) The combination of (d), wherein the HCV antiviral agents are one or more antiviral agents selected from the group consisting of direct inhibitors of HCV, including but not limited to NS3 and NS3/4A protease inhibitors, NS5A inhibitors and HCV NS5B polymerase inhibitors.

(f) A use of a compound of formula I in the preparation of a medicament for inhibiting HCV NS5B activity in a subject in need thereof.

(g) A use of a compound of formula I in the preparation of a medicament for preventing and/or treating infection by HCV in a subject in need thereof.

(h) A method of treating HCV infection and/or reducing the likelihood or severity of symptoms of HCV infection in a subject in need thereof, which comprises administering to the subject an effective amount of a compound of formula I.

(i) The method of (h), wherein the compound of formula I is administered in combination with an effective amount of at least one second therapeutic agent selected from the group consisting of HCV antiviral agents, immunomodulators, and anti-infective agents.

(j) The method of (i), wherein the HCV antiviral agent is an antiviral selected from the group consisting of direct inhibitors of HCV, including but not limited to NS3 and NS3/4A protease inhibitors, NS5A inhibitors and HCV NS5B polymerase inhibitors.

(k) A method of inhibiting HCV viral replication and/or HCV viral production in a cell-based system, which comprises administering to the subject an effective amount of a compound of formula I in combination with an effective amount of at least one second therapeutic agent selected from the group consisting of HCV antiviral agents, immunomodulators, and anti-infective agents.

(l) The method of (k), wherein the HCV antiviral agent is an antiviral selected from the group consisting of direct inhibitors of HCV, including but not limited to NS3 and NS3/4A protease inhibitors, NS5A inhibitors and HCV NS5B polymerase inhibitors.

(m) A method of inhibiting HCV NS5B activity in a subject in need thereof, which comprises administering to the subject the pharmaceutical composition of (a), (b), or (c) or the combination of (d) or (e).

(n) A method of treating HCV infection and/or reducing the likelihood or severity of symptoms of HCV infection in a subject in need thereof, which comprises administering to the subject the pharmaceutical composition of (a), (b), or (c) or the combination of (d) or (e).

In the embodiments of the compounds and salts provided above, it is to be understood that each embodiment may be combined with one or more other embodiments, to the extent that such a combination provides a stable compound or salt and is consistent with the description of the embodiments. It is further to be understood that the embodiments of compositions and methods provided as (a) through (n) above are understood to include all embodiments of the compounds and/or salts, including such embodiments as result from combinations of embodiments.

Additional embodiments of the invention include the pharmaceutical compositions, combinations, uses and methods set forth in (a) through (n) above, wherein the compound of the present invention employed therein is a compound of one of the embodiments, aspects, classes, sub-classes, or features of the compounds described above. In all of these embodiments, the compound may optionally be used in the form of a pharmaceutically acceptable salt or hydrate as appropriate.

The present invention also includes a compound of the present invention for use (i) in, (ii) as a medicament for, or (iii) in the preparation of a medicament for: (a) inhibiting HCV NS5B activity, or (b) inhibiting HCV viral replication, or (c) treating HCV infection and/or reducing the likelihood or severity of symptoms of HCV infection, or (d) use in medicine. In these uses, the compounds of the present invention can optionally be employed in combination with one or more second therapeutic agents selected from HCV antiviral agents, anti-infective agents, and immunomodulators.

Chemical names, common names, and chemical structures may be used interchangeably to describe the same structure. If a chemical compound is referred to using both a chemical structure and a chemical name and an ambiguity exists between the structure and the name, the structure is understood to predominate.

As used herein, the term "administration" and variants thereof (e.g., "administering" a compound) in reference to a compound of the invention mean providing the compound to the individual in need of treatment. When a compound of the invention is provided in combination with one or more other active agents (e.g., antiviral agents useful for treating HCV infection), "administration" and its variants are each understood to include concurrent and sequential provision of the compound or salt and other agents.

As used herein, the term "alkenyl" refers to an aliphatic hydrocarbon group containing at least one carbon-carbon double bond and having one of its hydrogen atoms replaced with a bond. An alkenyl group may be straight or branched and contain from about 2 to about 15 carbon atoms. In one embodiment, an alkenyl group contains from about 2 to about 12 carbon atoms. In another embodiment, an alkenyl group contains from about 2 to about 6 carbon atoms. Non-limiting examples of alkenyl groups include ethenyl, propenyl, n-butenyl, 3-methylbut-2-enyl, n-pentenyl, octenyl and decenyl. An alkenyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —NH$_2$, —NH(alkyl), —N(alkyl)$_2$, —NH(cycloalkyl), —O—C(O)-alkyl, —O—C(O)-aryl, —O—C(O)-cycloalkyl, —C(O)OH and —C(O)O-alkyl. The term "C$_2$-C$_6$ alkenyl" refers to an alkenyl group having from 2 to 6 carbon atoms. Unless otherwise indicated, an alkenyl group is unsubstituted.

As used herein, the term "alkoxy" refers to an "alkyl-O—" group. Alkoxy groups may be substituted as indicated.

The term "alkyl" refers to an aliphatic hydrocarbon group having one of its hydrogen atoms replaced with a bond. An alkyl group may be straight or branched and contain from about 1 to about 20 carbon atoms. In one embodiment, an alkyl group contains from about 1 to about 12 carbon atoms. In different embodiments, an alkyl group contains from 1 to 6 carbon atoms (C$_1$-C$_6$ alkyl) or from about 1 to about 3 carbon atoms (C$_1$-C$_3$ alkyl). Non-limiting examples of alkyl groups include methyl, ethyl, n-propyl, isopropyl, n-butyl, sec-butyl, isobutyl, tert-butyl, n-pentyl, neopentyl, isopentyl, n-hexyl, isohexyl and neohexyl. An alkyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —NH$_2$, —NH(alkyl), —N(alkyl)$_2$, —NH(cycloalkyl), —O—C(O)-alkyl, —O—C(O)-aryl, —O—C(O)-cycloalkyl, —C(O)OH and —C(O)O-alkyl. In one embodiment, an alkyl group is linear. In another embodiment, an alkyl group is branched. Unless otherwise indicated, an alkyl group is unsubstituted.

The term "alkynyl," as used herein, refers to an aliphatic hydrocarbon group containing at least one carbon-carbon triple bond and having one of its hydrogen atoms replaced with a bond. An alkynyl group may be straight or branched and contain from about 2 to about 15 carbon atoms. In one embodiment, an alkynyl group contains from about 2 to about 12 carbon atoms. In another embodiment, an alkynyl group contains from about 2 to about 6 carbon atoms. Non-limiting examples of alkynyl groups include ethynyl, propynyl, 2-butynyl and 3-methylbutynyl. An alkynyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —NH$_2$, —NH(alkyl), —N(alkyl)$_2$, —NH(cycloalkyl), —O—C(O)— alkyl, —O—C(O)-aryl, —O—C(O)-cycloalkyl, —C(O)OH and —C(O)O-alkyl. The term "C$_2$-C$_6$ alkynyl" refers to an alkynyl group having from 2 to 6 carbon atoms. Unless otherwise indicated, an alkynyl group is unsubstituted.

The term "aryl" (or "aryl ring system") refers to aromatic mono- and poly-carbocyclic ring systems wherein the individual carbocyclic rings in the polyring systems are fused or attached to each other via a single bond. As used herein, the term aryl includes aromatic mono- and poly-carbocyclic ring systems that include from 0 to 4 heteroatoms (non-carbon atoms) that are independently chosen from N, O and S. Suitable aryl groups include phenyl, naphthyl, biphenylenyl, pyridinyl, pyrimidinyl and pyrrolyl, as well as those discussed below. Aryl groups may be substituted as indicated. Aryl ring systems may include, where appropriate, an indication of the variable to which a particular ring atom is attached. Unless otherwise indicated, substituents to the aryl ring systems can be attached to any ring atom, provided that such attachment results in formation of a stable ring system.

The term "carbocycle" (and variations thereof such as "carbocyclic") as used herein, unless otherwise indicated, refers to (i) a C$_5$ to C$_7$ monocyclic, saturated or unsaturated ring, or (ii) a C$_8$ to C$_{10}$ bicyclic saturated or unsaturated ring system. Each ring in (ii) is either independent of, or fused to, the other ring, and each ring is saturated or unsaturated. Carbocycle groups may be substituted as indicated. When the carbocycles contain one or more heteroatoms independently chosen from N, O and S, the carbocycles may also be referred to as "heterocycles," as defined below. The carbocycle may be attached to the rest of the molecule at any carbon or nitrogen atom that results in a stable compound. The fused bicyclic carbocycles are a subset of the carbocycles; i.e., the term "fused bicyclic carbocycle" generally refers to a C$_8$ to C$_{10}$ bicyclic ring system in which each ring is saturated or unsaturated and two adjacent carbon atoms are shared by each of the rings in the ring system. A fused bicyclic carbocycle in which both rings are saturated is a saturated bicyclic ring system. Saturated carbocyclic rings are also referred to as cycloalkyl rings, e.g., cyclopropyl, cyclobutyl, etc. A fused bicyclic carbocycle in which one or both rings are unsaturated is an unsaturated bicyclic ring system. Carbocycle ring systems may include, where appropriate, an indication of the variable to which a particular ring atom is attached. Unless otherwise indicated, substituents to the ring systems can be attached to any ring atom, provided that such attachment results in formation of a stable ring system.

The term "composition" is intended to encompass a product comprising the specified ingredients, as well as any product which results, directly or indirectly, from combining the specified ingredients.

The term "compound" is intended to encompass chemical agents described by generic formula I in all forms, including hydrates and solvates of such chemical agents.

The term "cycloalkenyl," as used herein, refers to a non-aromatic mono- or multicyclic ring system comprising from about 4 to about 10 ring carbon atoms and containing at least one endocyclic double bond. In one embodiment, a cycloalkenyl contains from about 4 to about 7 ring carbon atoms. In another embodiment, a cycloalkenyl contains 5 or 6 ring atoms. Non-limiting examples of monocyclic cycloalkenyls include cyclopentenyl, cyclohexenyl, cyclohepta-1,3-dienyl, and the like. A cycloalkenyl group can be optionally substituted with one or more "ring system substituents" which may be the same or different, and are as defined herein below. A ring carbon atom of a cycloalkyl group may be functionalized as a carbonyl group. In one embodiment, a cycloalkenyl group is cyclopentenyl. In another embodiment, a cycloalkenyl group is cyclohexenyl. The term "4 to 7-membered cycloalkenyl" refers to a cycloalkenyl group having from 4 to 7 ring carbon atoms. Unless otherwise indicated, a cycloalkenyl group is unsubstituted.

The term "cycloalkyl," as used herein, refers to a non-aromatic mono- or multicyclic ring system comprising from about 3 to about 10 ring carbon atoms. In one embodiment, a cycloalkyl contains from about 5 to about 10 ring carbon atoms. In another embodiment, a cycloalkyl contains from about 3 to about 7 ring atoms. In another embodiment, a cycloalkyl contains from about 5 to about 7 ring atoms. In another embodiment, a cycloalkyl contains from about 5 to about 6 ring atoms. The term "cycloalkyl" also encompasses a cycloalkyl group, as defined above, which is fused to an aryl (e.g., benzene) or heteroaryl ring. Non-limiting examples of monocyclic cycloalkyls include cyclopropyl, cyclobutyl, cyclopentyl, cyclohexyl, cycloheptyl and cyclooctyl. Non-limiting examples of multicyclic cycloalkyls include 1-decalinyl, norbornyl, bicyclo[3.1.0]hexyl and adamantyl. A cycloalkyl group can be optionally substituted with one or more "ring system substituents" which may be the same or different, and are as defined herein below. In one embodiment, a cycloalkyl group is unsubstituted. The term "3 to 7-membered cycloalkyl" refers to a cycloalkyl group having from 3 to 7 ring carbon atoms. Unless otherwise indicated, a cycloalkyl group is unsubstituted. A ring carbon atom of a cycloalkyl group may be functionalized as a carbonyl group. An illustrative example of such a cycloalkyl group (also referred to herein as a "cycloalkanoyl" group) includes, but is not limited to, cyclobutanol:

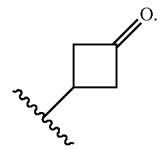 [SMILES: *C1CC(=O)C1]

The term "effective amount" as used herein means that amount of active compound or pharmaceutical agent that elicits the biological or medicinal response in a tissue, system, animal or human that is being sought by a researcher, veterinarian, medical doctor or other clinician. In one embodiment, the effective amount is a "therapeutically effective amount" for the alleviation of one or more symptoms of the disease or condition being treated. In another embodiment, the effective amount is a "prophylactically effective amount" for reduction of the severity or likelihood of one or more symptoms of the disease or condition. In another embodiment, the effective amount is a "therapeutically effective amount" for inhibition of HCV viral replication and/or HCV viral production. The term also includes herein the amount of active compound sufficient to inhibit HCV NS5B activity and thereby elicit the response being sought (i.e., an "inhibition effective amount"). When the active compound (i.e., active ingredient) is administered as the salt, references to the amount of active ingredient are to the free acid or free base form of the compound.

The term "haloalkyl," as used herein, refers to an alkyl group as defined above, wherein one or more of the alkyl group's hydrogen atoms has been replaced with a halogen. In one embodiment, a haloalkyl group has from 1 to 6 carbon atoms. In another embodiment, a haloalkyl group is substituted with from 1 to 3 F atoms. Non-limiting examples of haloalkyl groups include —$CH_2F$, —$CHF_2$, —$CF_3$, —$CH_2Cl$ and —$CCl_3$. The term "$C_1$-$C_6$ haloalkyl" refers to a haloalkyl group having from 1 to 6 carbon atoms.

The term "halogen" (or "halo") refers to atoms of fluorine, chlorine, bromine and iodine (alternatively referred to as fluoro, chloro, bromo, and iodo).

The term "heterocycloalkenyl," as used herein, refers to a heterocycloalkyl group, as defined above, wherein the heterocycloalkyl group contains from 4 to 10 ring atoms, and at least one endocyclic carbon-carbon or carbon-nitrogen double bond. A heterocycloalkenyl group can be joined via a ring carbon or ring nitrogen atom. In one embodiment, a heterocycloalkenyl group has from 4 to 7 ring atoms. In another embodiment, a heterocycloalkenyl group is monocyclic and has 5 or 6 ring atoms. In another embodiment, a heterocycloalkenyl group is bicyclic. A heterocycloalkenyl group can optionally substituted by one or more ring system substituents, wherein "ring system substituent" is as defined above. The nitrogen or sulfur atom of the heterocycloalkenyl can be optionally oxidized to the corresponding N-oxide, S-oxide or S,S-dioxide. Non-limiting examples of heterocycloalkenyl groups include 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl, dihydrothiazolyl, 3,4-dihydro-2H-pyranyl, dihydrofuranyl, fluoro-substituted dihydrofuranyl, 7-oxabicyclo[2.2.1]heptenyl, dihydrothiophenyl, dihydrothiopyranyl, and the like and the like. A ring carbon atom of a heterocycloalkenyl group may be functionalized as a carbonyl group. In one embodiment, a heterocycloalkenyl group is a 5-membered heterocycloalkenyl. In another embodiment, a heterocycloalkenyl group is a 6-membered heterocycloalkenyl. The term "4 to 7-membered heterocycloalkenyl" refers to a heterocycloalkenyl group having from 4 to 7 ring atoms. Unless otherwise indicated, a heterocycloalkenyl group is unsubstituted.

The term "heteroaryl," as used herein, refers to an aromatic monocyclic or multicyclic ring system comprising about 5 to about 14 ring atoms, wherein from 1 to 4 of the ring atoms is independently O, N or S and the remaining ring atoms are carbon atoms. In one embodiment, a heteroaryl group has 5 to 10 ring atoms. In another embodiment, a heteroaryl group is monocyclic and has 5 or 6 ring atoms. In another embodiment, a heteroaryl group is bicyclic and has 9 or 10 ring atoms. A heteroaryl group can be optionally substituted by one or more "ring system substituents" which may be the same or different, and are as defined herein below. A heteroaryl group is joined via a ring carbon atom, and any nitrogen atom of a heteroaryl can be optionally oxidized to the corresponding N-oxide. The term "heteroaryl" also encompasses a heteroaryl group, as defined above, which is fused to a benzene ring. The term "heteroaryl" also encompasses any fused polycyclic ring system containing at least one ring heteroatom selected from N, O and S, wherein at least one ring of the fused polycyclic ring system is aromatic. For example, the term "9 to 10-membered bicyclic heteroaryl" encompasses a non-aromatic 5 membered heterocyclic ring that is fused to a benzene or pyridyl ring. Non-limiting examples of heteroaryls include pyridyl, pyrazinyl, furanyl, thienyl, pyrimidinyl, pyridone (including N-substituted pyridones), isoxazolyl, isothiazolyl, oxazolyl, oxadiazolyl, thiazolyl, pyrazolyl, furazanyl, pyrrolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, benzimidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like, and all isomeric forms thereof. The term "heteroaryl" also refers to partially saturated heteroaryl moieties such as, for example, tetrahydroisoquinolyl, tetrahydroquinolyl and the like. In one embodiment, a heteroaryl group is a 5-membered heteroaryl. In another embodiment, a heteroaryl group is a 6-membered heteroaryl. In another embodiment, a heteroaryl group comprises a 5- to 6-membered heteroaryl group fused to a benzene ring. Unless otherwise indicated, a heteroaryl group is unsubstituted.

As used herein, the term "heterocycle" (and variations thereof such as "heterocyclic" or "heterocyclyl") broadly refers to (i) a stable 5- to 7-membered, saturated or unsaturated monocyclic ring, or (ii) a stable 8- to 10-membered bicyclic ring system, wherein each ring in (ii) is independent of, or fused to, the other ring or rings and each ring is saturated or unsaturated, and the monocyclic ring or bicyclic ring system contains one or more heteroatoms (e.g., from 1 to 6 heteroatoms, or from 1 to 4 heteroatoms) independently selected from N, O and S and a balance of carbon atoms (the monocyclic ring typically contains at least one carbon atom and the bicyclic ring systems typically contain at least two carbon atoms); and wherein any one or more of the nitrogen and sulfur heteroatoms is optionally oxidized, and any one or more of the nitrogen heteroatoms is optionally quaternized. Unless otherwise specified, the heterocyclic ring may be attached at any heteroatom or carbon atom, provided that attachment results in the creation of a stable structure. Heterocycle groups may be substituted as indicated, and unless otherwise specified, the substituents may be attached to any atom in the ring, whether a heteroatom or a carbon atom, provided that a stable chemical structure results. Representative examples include piperidinyl, piperazinyl, azepanyl, pyrrolidinyl, pyrazolidinyl, imidazolidinyl, oxazolidinyl, isoxazolidinyl, morpholinyl, thiomorpholinyl, thiazolidinyl, isothiazolidinyl, and tetrahydrofuryl (or tetrahydrofuranyl).

The term "heterocycloalkyl," as used herein, refers to a non-aromatic saturated monocyclic or multicyclic ring system comprising 3 to about 11 ring atoms, wherein from 1 to 4 of the ring atoms are independently O, S, or N, and the remainder of the ring atoms are carbon atoms. A heterocycloalkyl group can be joined via a ring carbon or ring nitrogen atom. In one embodiment, a heterocycloalkyl group is monocyclic and has from about 3 to about 7 ring atoms. In another embodiment, a heterocycloalkyl group is monocyclic has from about 4 to about 7 ring atoms. In another embodiment, a heterocycloalkyl group is monocyclic has from about 5 to about 7 ring atoms. In another embodiment, a heterocycloalkyl group is bicyclic and has from about 7 to about 11 ring atoms. In still another embodiment, a heterocycloalkyl group is monocyclic and has 5 or 6 ring atoms. In one embodiment, a heterocycloalkyl group is monocyclic. In another embodiment, a heterocycloalkyl group is bicyclic. There are no adjacent oxygen and/or sulfur atoms present in the ring system. Any —NH group in a heterocycloalkyl ring may exist protected such as, for example, as an —N(BOC), —N(Cbz), —N(Tos) group and the like; such protected heterocycloalkyl groups are considered part of this invention. The term "heterocycloalkyl" also encompasses a heterocycloalkyl group, as defined above, which is fused to an aryl (e.g., benzene) or heteroaryl ring. A heterocycloalkyl group can be optionally substituted by one or more "ring system substituents" which may be the same or different, and are as defined herein below. The nitrogen or sulfur atom of the heterocycloalkyl can be optionally oxidized to the corresponding N-oxide, S-oxide or S,S-dioxide. Non-limiting examples of monocyclic heterocycloalkyl rings include oxetanyl, piperidyl, pyrrolidinyl, piperazinyl, morpholinyl, thiomorpholinyl, thiazolidinyl, 1,4-dioxanyl, tetrahydrofuranyl, tetrahydrothiophenyl, delta-lactam, delta-lactone, and the like, and all isomers thereof.

A ring carbon atom of a heterocycloalkyl group may be functionalized as a carbonyl group. Illustrative example of such heterocycloalkyl groups, include:

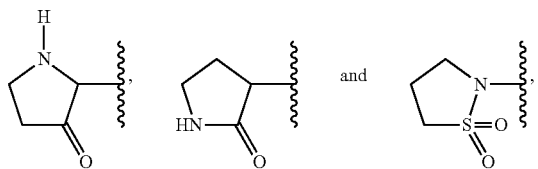 [SMILES: *C1NCCC1=O ; *C1CCNC1=O ; *N1CCCS1(=O)=O]

In one embodiment, a heterocycloalkyl group is a 5-membered monocyclic heterocycloalkyl. In another embodiment, a heterocycloalkyl group is a 6-membered monocyclic heterocycloalkyl. The term "3 to 7-membered monocyclic cycloalkyl" refers to a monocyclic heterocycloalkyl group having from 3 to 7 ring atoms. The term "4 to 7-membered monocyclic cycloalkyl" refers to a monocyclic heterocycloalkyl group having from 4 to 7 ring atoms. The term "5 to 7-membered monocyclic cycloalkyl" refers to a monocyclic heterocycloalkyl group having from 5 to 7 ring atoms. The term "7 to 11-membered bicyclic heterocycloalkyl" refers to a bicyclic heterocycloalkyl group having from 7 to 11 ring atoms. Unless otherwise indicated, an heterocycloalkyl group is unsubstituted.

The term "hydroxyalkyl," as used herein, refers to an alkyl group as defined above, wherein one or more of the alkyl group's hydrogen atoms has been replaced with an —OH group. In one embodiment, a hydroxyalkyl group has from 1 to 6 carbon atoms. Non-limiting examples of hydroxyalkyl groups include —CH$_2$OH, —CH$_2$CH$_2$OH, —CH$_2$CH$_2$CH$_2$OH and —CH$_2$CH(OH)CH$_3$. The term "C$_1$-C$_6$ hydroxyalkyl" refers to a hydroxyalkyl group having from 1 to 6 carbon atoms.

As used herein, the term "oxo" or "=O" forms a carbonyl moiety with the carbon atom to which it is attached.

By "pharmaceutically acceptable" is meant that the ingredients of the pharmaceutical composition must be compatible with each other and not deleterious to the recipient thereof.

The term "preventing," as used herein with respect to an HCV viral infection or HCV-virus related disorder, refers to reducing the likelihood of HCV infection.

The term "ring system substituent," as used herein, refers to a substituent group attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, -alkylene-aryl, -arylene-alkyl, -alkylene-heteroaryl, -alkenylene-heteroaryl, -alkynylene-heteroaryl, —OH, hydroxyalkyl, haloalkyl, —O-alkyl, —O-haloalkyl, -alkylene-O-alkyl, —O-aryl, —O— alkylene-aryl, acyl, —C(O)-aryl, halo, —NO$_2$, —CN, —SF$_5$, —C(O)OH, —C(O)O-alkyl, —C(O)O-aryl, —C(O)O-alkylene-aryl, —S(O)-alkyl, —S(O)$_2$-alkyl, —S(O)-aryl, —S(O)$_2$-aryl, —S(O)-heteroaryl, —S(O)$_2$-heteroaryl, —S-alkyl, —S-aryl, —S-heteroaryl, —S-alkylene-aryl, —S-alkylene-heteroaryl, —S(O)$_2$-alkylene-aryl, —S(O)$_2$-alkylene-heteroaryl, cycloalkyl, heterocycloalkyl, —O—C(O)-alkyl, —O—C(O)-aryl, —O—C(O)-cycloalkyl, —C(=N—CN)—NH$_2$, —C(=NH)—NH$_2$, —C(=NH)—NH(alkyl), —N(Y$_1$)(Y$_2$), -alkylene-N(Y$_1$)(Y$_2$), —C(O)N(Y$_1$)(Y$_2$) and —S(O)$_2$N(Y$_1$)(Y$_2$), wherein Y$_1$ and Y$_2$ can be the same or different and are independently selected from the group consisting of hydrogen, alkyl, aryl, cycloalkyl, and -alkylene-aryl. "Ring system substituent" may also mean a single moiety which simultaneously replaces two available hydrogens on two adjacent carbon atoms (one H on each carbon) on a ring system. Examples of such moiety are methylenedioxy, ethylenedioxy, —C(CH$_3$)$_2$— and the like which form moieties such as, for example:

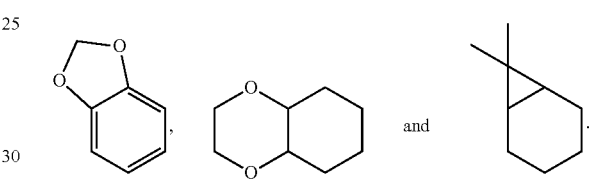

The term "subject" (alternatively referred to herein as "patient"), as used herein, refers to an animal, preferably a mammal, most preferably a human.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture.

In the compounds of formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of formula I. For example, different isotopic forms of hydrogen (H) include protium ($^1$H) and deuterium ($^2$H or D). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within formula I can be prepared without undue experimentation by conventional techniques well known to those skilled in the art or by processes analogous to those described in the Schemes and Examples herein using appropriate isotopically-enriched reagents and/or intermediates.

Unless expressly stated to the contrary, all ranges cited herein are inclusive. For example, a heteroaryl ring described as containing from "0 to 3 heteroatoms" means the ring can contain 0, 1, 2, or 3 heteroatoms. It is also to be understood that any range cited herein includes within its scope all of the sub-ranges within that range. The oxidized forms of the heteroatoms N and S are also included within the scope of the present invention.

When any variable (for example, $R^1$ or $R^3$) occurs more than one time in any constituent or in formula I or in any other formula depicting and describing compounds of the invention, its definition on each occurrence is independent of its definition at every other occurrence. Also, combinations of substituents and/or variables are permissible only if such combinations result in stable compounds.

Unless expressly stated to the contrary, substitution by a named substituent is permitted on any atom provided such substitution is chemically allowed and results in a stable compound. A "stable" compound is a compound that can be prepared and isolated and whose structure and properties remain or can be caused to remain essentially unchanged for a period of time sufficient to allow use of the compound for the purposes described herein (e.g., therapeutic or prophylactic administration to a subject).

Certain of the compounds of the present invention can have asymmetric centers and can occur as mixtures of stereoisomers, or as individual diastereomers, or enantiomers. All isomeric forms of these compounds, whether isolated or in mixtures, are within the scope of the present invention.

Certain of the compounds of the present invention can exist as tautomers. For the purposes of the present invention a reference to a compound of formula I is a reference to the compound per se, or to any one of its tautomers per se, or to mixtures of two or more tautomers.

The compounds of the present inventions are useful in the inhibition of HCV replication (e.g., HCV NS5B activity), the treatment of HCV infection and/or reduction of the likelihood or severity of symptoms of HCV infection. For example, the compounds of this invention are useful in treating infection by HCV after suspected past exposure to HCV by such means as blood transfusion, exchange of body fluids, bites, accidental needle stick, or exposure to patient blood during surgery.

The compounds of this invention are useful in the preparation and execution of screening assays for antiviral compounds. For example, the compounds of this invention are useful for identifying resistant HCV replicon cell lines harboring mutations within NS5B, which are excellent screening tools for more powerful antiviral compounds. Furthermore, the compounds of this invention are useful in establishing or determining the binding site of other antivirals to the HCV replicase.

The compounds of the present invention may be administered in the form of pharmaceutically acceptable salts. The term "pharmaceutically acceptable salt" refers to a salt that possesses the effectiveness of the parent compound and that is not biologically or otherwise undesirable (e.g., is neither toxic nor otherwise deleterious to the recipient thereof). Suitable salts include acid addition salts that may, for example, be formed by mixing a solution of the compound of the present invention with a solution of a pharmaceutically acceptable acid such as hydrochloric acid, sulfuric acid, acetic acid, trifluoroacetic acid, or benzoic acid. Many of the compounds of the invention carry an acidic moiety, in which case suitable pharmaceutically acceptable salts thereof can include alkali metal salts (e.g., sodium or potassium salts), alkaline earth metal salts (e.g., calcium or magnesium salts), and salts formed with suitable organic ligands such as quaternary ammonium salts. Also, in the case of an acid (—COOH) or alcohol group being present, pharmaceutically acceptable esters can be employed to modify the solubility or hydrolysis characteristics of the compound.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates ("mesylates"), naphthalenesulfonates, nitrates, oxalates, phosphates, propionates, salicylates, succinates, sulfates, tartarates, thiocyanates, toluenesulfonates (also known as tosylates) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamine, t-butyl amine, choline, and salts with amino acids such as arginine, lysine and the like. Basic nitrogen-containing groups may be quaternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

For the purposes of inhibiting HCV NS5B polymerase, treating HCV infection and/or reducing the likelihood or severity of symptoms of HCV infection and inhibiting HCV viral replication and/or HCV viral production, the compounds of the present invention, optionally in the form of a salt, can be administered by any means that produces contact of the active agent with the agent's site of action. They can be administered by one or more conventional means available for use in conjunction with pharmaceuticals, either as individual therapeutic agents or in a combination of therapeutic agents. They can be administered alone, but typically are administered with a pharmaceutical carrier selected on the basis of the chosen route of administration and standard pharmaceutical practice. The compounds of the invention can, for example, be administered by one or more of the following: orally, parenterally (including subcutaneous injections, intravenous, intramuscular, intrasternal injection or infusion techniques), by inhalation (such as in a spray form), or rectally, in the form of a unit dosage of a pharmaceutical composition containing an effective amount of the compound and conventional non-toxic pharmaceutically-acceptable carriers, adjuvants and vehicles. Liquid preparations suitable for oral administration (e.g., suspensions, syrups, elixirs and the like) can be prepared according to techniques known in the art and can employ any of the usual media such as water, glycols, oils, alcohols and the like. Solid preparations suitable for oral administration (e.g., powders, pills, capsules and tablets) can be prepared according to techniques known in the art and can employ such solid excipients as starches, sugars, kaolin, lubricants, binders, disintegrating agents and the like. Parenteral compositions can be prepared according to techniques known in the art and typically employ sterile water as a carrier and optionally other ingredients, such as solubility aids. Injectable solutions can be prepared according to methods known in the art wherein the carrier comprises a saline solution, a glucose solution or a solution containing a mixture of saline and glucose. Further description of methods suitable for use in preparing pharmaceutical compositions of the present invention and of ingredients suitable for use in said compositions is provided in *Remington's Pharmaceutical Sciences*, 18th edition (ed. A. R. Gennaro, Mack Publishing Co., 1990).

The compounds of this invention can be administered orally in a dosage range of 0.001 to 1000 mg/kg of mammal (e.g., human) body weight per day in a single dose or in divided doses. One dosage range is 0.01 to 500 mg/kg body weight per day orally in a single dose or in divided doses. Another dosage range is 0.1 to 100 mg/kg body weight per day orally in single or divided doses. For oral administration, the compositions can be provided in the form of tablets or capsules containing 1.0 to 500 mg of the active ingredient, particularly 1, 5, 10, 15, 20, 25, 50, 75, 100, 150, 200, 250, 300, 400, and 500 mg of the active ingredient for the symptomatic adjustment of the dosage to the patient to be treated. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, HCV viral genotype, viral resistance, and the host undergoing therapy.

As noted above, the present invention also relates to a method of inhibiting HCV NS5B activity, inhibiting HCV viral replication and/or HCV viral production, treating HCV infection and/or reducing the likelihood or severity of symptoms of HCV infection with a compound of the present invention in combination with one or more therapeutic agents and a pharmaceutical composition comprising a compound of the present invention and one or more therapeutic agents selected from the group consisting of a HCV antiviral agent, an immuno modulator, and an anti-infective agent. Such therapeutic agents active against HCV include, but are not limited to, ribavirin, levovirin, viramidine, thymosin alpha-1, R7025 (an enhanced interferon (Roche)), interferon-β, interferon-α, pegylated interferon-α (peginterferon-α), a combination of interferon-α and ribavirin, a combination of peginterferon-α and ribavirin, a combination of interferon-α and levovirin, and a combination of peginterferon-α and levovirin. Interferon-α includes, but is not limited to, recombinant interferon-α2a (such as ROFERON interferon available from Hoffmann-LaRoche, Nutley, N.J.), pegylated interferon-α2a (PEGASYS), interferon-α2b (such as INTRON-A interferon available from Schering Corp., Kenilworth, N.J.), pegylated interferon-α2b (PEGINTRON), a recombinant consensus interferon (such as interferon alphacon-1), albuferon (interferon-α bound to human serum albumin (Human Genome Sciences)), and a purified interferon-α product. Amgen's recombinant consensus interferon has the brand name INFERGEN. Levovirin is the L-enantiomer of ribavirin which has shown immuno-modulatory activity similar to ribavirin. Viramidine represents an analog of ribavirin disclosed in International Patent Application Publication WO 01/60379. In accordance with the method of the present invention, the individual components of the combination can be administered separately at different times during the course of therapy or concurrently in divided or single combination forms.

For the treatment of HCV infection, the compounds of the invention may also be administered in combination with the antiviral agent NS5B polymerase inhibitor R7128 (Roche). The compounds of the present invention also may be combined for the treatment of HCV infection with antiviral 2'-C-branched ribonucleosides disclosed in Rogers E. Harry-O'Kuru et al., *A Short, Flexible Route toward* 2'-*C*-*Branched Ribonucleosides*, 62 J. ORG. CHEM. 1754-59 (1997); Michael S. Wolfe & Rogers E. Harry-O'Kuru, *A Concise Synthesis of* 2'-*C*-*Methylribonucleosides*, 36(42) TETRAHEDRON LETTERS 7611-14 (1995); U.S. Pat. No. 3,480,613; and International Patent Application Publications WO 01/90121, WO 01/92282, WO 02/32920, WO 04/002999, WO 04/003000 and WO 04/002422; the entire contents of each of which are incorporated by reference. Such 2'-C-branched ribonucleosides include, but are not limited to, 2'-C-methyl-cytidine, 2'-C-methyl-uridine, 2'-C-methyl-adenosine, 2'-C-methyl-guanosine, and 9-(2-C-methyl-β-D-ribofuranosyl)-2,6-di-aminopurine, and the corresponding amino acid ester of the ribose C-2', C-3', and C-5' hydroxyls and the corresponding optionally substituted cyclic 1,3-propanediol esters of the 5'-phosphate derivatives.

For the treatment of HCV infection, the compounds of the present invention may also be administered in combination with an agent that is an inhibitor of HCV NS3 serine protease. HCV NS3 serine protease is an essential viral enzyme and has been described to be an excellent target for inhibition of HCV replication. Exemplary substrate and non-substrate based inhibitors of HCV NS3 protease inhibitors are disclosed in International Patent Application Publications WO 98/22496, WO 98/46630, WO 99/07733, WO 99/07734, WO 99/38888, WO 99/50230, WO 99/64442, WO 00/09543, WO 00/59929, WO 02/48116, WO 02/48172, WO 2008/057208 and WO 2008/057209, in British Patent No. GB 2 337 262, and in U.S. Pat. Nos. 6,323,180 and 7,470,664.

The compounds of the present invention may also be combined for the treatment of HCV infection with nucleosides having anti-HCV properties, such as those disclosed in International Patent Application Publications WO 02/51425, WO 01/79246, WO 02/32920, WO 02/48165 and WO 2005/003147 (including R1656, (2'R)-2'-deoxy-2'-fluoro-2'-C-methylcytidine, shown as compounds 3-6 on page 77); WO 01/68663; WO 99/43691; WO 02/18404 and WO 2006/021341, and U.S. Patent Application Publication US 2005/0038240, including 4'-azido nucleosides such as R1626, 4'-azidocytidine; U.S. Patent Application Publications US 2002/0019363, US 2003/0236216, US 2004/0006007, US 2004/0063658 and US 2004/0110717; U.S. Pat. Nos. 7,105,499, 7,125,855, 7,202,224; and International Patent Application Publications WO 02/100415, WO 03/026589, WO 03/026675, WO 03/093290, WO 04/011478, WO 04/013300 and WO 04/028481; the content of each is incorporated herein by reference in its entirety.

For the treatment of HCV infection, the compounds of the present invention may also be administered in combination with an agent that is an inhibitor of HCV NS5B polymerase. Such HCV NS5B polymerase inhibitors that may be used as combination therapy include, but are not limited to, those disclosed in International Patent Application Publications WO 02/057287, WO 02/057425, WO 03/068244, WO 2004/000858, WO 04/003138 and WO 2004/007512; U.S. Pat. Nos. 6,777,392, 7,105,499, 7,125,855, 7,202,224 and U.S. Patent Application Publications US 2004/0067901 and US 2004/0110717; the content of each is incorporated herein by reference in its entirety. Other such HCV polymerase inhibitors include, but are not limited to, valopicitabine (NM-283; Idenix) and 2'-F-2'-beta-methylcytidine (see also WO 2005/003147).

In one embodiment, additional nucleoside HCV NS5B polymerase inhibitors that are used in combination with the present HCV NS5B inhibitors are selected from the following compounds: 4-amino-7-(2-C-methyl-β-D-arabinofuranosyl)-7H-pyrrolo[2,3-d]pyrimidine; 4-amino-7-(2-C-methyl-β-D-ribofuranosyl)-7H-pyrrolo[2,3-d]pyrimidine; 4-methylamino-7-(2-C-methyl-β-D-ribofuranosyl)-7H-pyrrolo[2,3-d]pyrimidine; 4-dimethylamino-7-(2-C-methyl-β-D-ribofuranosyl)-7H-pyrrolo[2,3-d]pyrimidine; 4-cyclopropylamino-7-(2-C-methyl-β-D-ribofuranosyl)-7H-pyrrolo[2,3-d]pyrimidine; 4-amino-7-(2-C-vinyl-β-D-ribofuranosyl)-7H-pyrrolo[2,3-d]pyrimidine; 4-amino-7-(2-C-hydroxymethyl-β-D-ribofuranosyl)-7H-pyrrolo[2,3-d]pyrimidine; 4-amino-7-(2-C-fluoromethyl-β-D-ribofuranosyl)-7H-pyrrolo[2,3-d]pyrimidine; 4-amino-5-methyl-7-(2-C-methyl-β-D-ribofuranosyl)-7H-pyrrolo[2,3-d]pyrimidine; 4-amino-7-(2-C-methyl-β-D-ribofuranosyl)-7H-pyrrolo[2,3-d]pyrimidine-5-carboxylic acid; 4-amino-5-bromo-7-(2-C-methyl-β-D-ribofuranosyl)-7H-pyrrolo[2,3-d]pyrimidine; 4-amino-5-chloro-7-(2-C-methyl-β-D-ribofuranosyl)-7H-pyrrolo[2,3-d]pyrimidine; 4-amino-5-fluoro-7-(2-C-methyl-β-D-ribofuranosyl)-7H-pyrrolo[2,3-d]pyrimidine; 2,4-diamino-7-(2-C-methyl-β-D-ribofuranosyl)-7H-pyrrolo[2,3-d]pyrimidine; 2-amino-7-(2-C-methyl-β-D-ribofuranosyl)-7H-pyrrolo[2,3-d]pyrimidine; 2-amino-4-cyclopropylamino-7-(2-C-methyl-β-D-ribofuranosyl)-7H-pyrrolo[2,3-d]pyrimidine; 2-amino-7-(2-C-methyl-β-D-ribofuranosyl)-7H-pyrrolo[2,3-d]pyrimidin-4(3H)-one; 4-amino-7-(2-C-ethyl-β-D-ribofuranosyl)-7H-pyrrolo[2,3-d]pyrimidine; 4-amino-7-(2-C,2-O-dimethyl-β-D-ribofuranosyl)-7H-pyrrolo[2,3-d]pyrimidine; 7-(2-C-methyl-β-D-ribofuranosyl)-7H-pyrrolo[2,3-d]pyrimidin-4(3H)-one; 2-amino-5-methyl-7-(2-C,2-O-dimethyl-β-D-ribofuranosyl)-7H-pyrrolo[2,3-d]pyrimidin-4(3H)-one; 4-amino-7-(3-deoxy-2-C-methyl-β-D-ribofuranosyl)-7H-pyrrolo[2,3-d]pyrimidine; 4-amino-7-(3-deoxy-2-C-methyl-β-D-arabinofuranosyl)-7H-pyrrolo[2,3-d]pyrimidine; 4-amino-2-fluoro-7-(2-C-methyl-β-D-ribofuranosyl)-7H-pyrrolo[2,3-d]pyrimidine; 4-amino-7-(3-C-methyl-β-D-ribofuranosyl)-7H-pyrrolo[2,3-d]pyrimidine; 4-amino-7-(3-C-methyl-β-D-xylofuranosyl)-7H-pyrrolo[2,3-d]pyrimidine; 4-amino-7-(2,4-di-C-methyl-β-D-ribofuranosyl)-7H-pyrrolo[2,3-d]pyrimidine; 4-amino-7-(3-deoxy-3-fluoro-2-C-methyl-β-D-ribofuranosyl)-7H-pyrrolo[2,3-d]pyrimidine; and the corresponding 5'-triphosphates; or a pharmaceutically acceptable salt thereof.

The compounds of the present invention may also be combined for the treatment of HCV infection with non-nucleoside inhibitors of HCV polymerase such as those disclosed in U.S. Patent Application Publications US 2006/0100262 and US 2009/0048239; International Patent Application Publications WO 01/77091, WO 01/47883, WO 02/04425, WO 02/06246, WO 02/20497, WO 2005/016927 (in particular JTK003), WO 2004/041201, WO 2006/066079, WO 2006/066080, WO 2008/075103, WO 2009/010783 and WO 2009/010785; the content of each is incorporated herein by reference in its entirety.

In one embodiment, additional non-nucleoside HCV NS5B polymerase inhibitors that are used in combination with the present HCV NS5B inhibitors are selected from the following compounds: 14-cyclohexyl-6-[2-(dimethylamino)ethyl]-7-oxo-5,6,7,8-tetrahydroindolo[2,1-a][2,5]benzodiazocine-11-carboxylic acid; 14-cyclohexyl-6-(2-morpholin-4-ylethyl)-5,6,7,8-tetrahydroindolo[2,1-a][2,5]benzodiazocine-11-carboxylic acid; 14-cyclohexyl-6-[2-(dimethylamino)ethyl]-3-methoxy-5,6,7,8-tetrahydroindolo[2,1-a][2,5]benzodiazocine-11-carboxylic acid; 14-cyclohexyl-3-methoxy-6-methyl-5,6,7,8-tetrahydroindolo[2,1-a][2,5]benzodiazocine-11-carboxylic acid; methyl ({[(14-cyclohexyl-3-methoxy-6-methyl-5,6,7,8-tetrahydroindolo[2,1-a][2,5]benzodiazocin-11-yl)carbonyl]amino}sulfonyl)acetate; ({[(14-cyclohexyl-3-methoxy-6-methyl-5,6,7,8-tetrahydroindolo[2,1-a][2,5]benzodiazocin-11-yl)carbonyl]amino}sulfonyl)acetic acid; 14-cyclohexyl-N-[(dimethylamino)sulfonyl]-3-methoxy-6-methyl-5,6,7,8-tetrahydroindolo[2,1-a][2,5]benzodiazocine-11-carboxamide; 3-chloro-14-cyclohexyl-6-[2-(dimethylamino)ethyl]-7-oxo-5,6,7,8-tetrahydroindolo[2,1-a][2,5]benzodiazocine 11-carboxylic acid; N-(11-carboxy-14-cyclohexyl-7,8-dihydro-6H-indolo[1,2-e][1,5]benzoxazocin-7-yl)-N,N-dimethylethane-1,2-diaminium bis(trifluoroacetate); 14-cyclohexyl-7,8-dihydro-6H-indolo[1,2-e][1,5]benzoxazocine-11-carboxylic acid; 14-cyclohexyl-6-methyl-7-oxo-5,6,7,8-tetrahydroindolo[2,1-a][2,5]benzodiazocine-11-carboxylic acid; 14-cyclohexyl-3-methoxy-6-methyl-7-oxo-5,6,7,8-tetrahydroindolo[2,1-a][2,5]benzodiazocine-11-carboxylic acid; 14-cyclohexyl-6-[2-(dimethylamino)ethyl]-3-methoxy-7-oxo-5,6,7,8-tetrahydroindolo[2,1-a][2,5]benzodiazocine-11-carboxylic acid; 14-cyclohexyl-6-[3-(dimethylamino)propyl]-7-oxo-5,6,7,8-tetrahydroindolo[2,1-a][2,5]benzodiazocine-11-carboxylic acid; 14-cyclohexyl-7-oxo-6-(2-piperidin-1-ylethyl)-5,6,7,8-tetrahydroindolo[2,1-a][2,5]benzodiazocine-11-carboxylic acid; 14-cyclohexyl-6-(2-morpholin-4-ylethyl)-7-oxo-5,6,7,8-tetrahydroindolo[2,1-a][2,5]benzodiazocine-11-carboxylic acid; 14-cyclohexyl-6-[2-(diethylamino)ethyl]-7-oxo-5,6,7,8-tetrahydroindolo[2,1-a][2,5]benzodiazocine-11-carboxylic acid; 14-cyclohexyl-6-(1-methylpiperidin-4-yl)-7-oxo-5,6,7,8-tetrahydroindolo[2,1-a][2,5]benzodiazocine-11-carboxylic acid; 14-cyclohexyl-N-[(dimethylamino)sulfonyl]-7-oxo-6-(2-piperidin-1-ylethyl)-5,6,7,8-tetrahydroindolo[2,1-a][2,5]benzodiazocine-11-carboxamide; 14-cyclohexyl-6-[2-(dimethylamino)ethyl]-N-[(dimethylamino)sulfonyl]-7-oxo-5,6,7,8-tetrahydroindolo[2,1-a][2,5]benzodiazocine-11-carboxamide; 14-cyclopentyl-6-[2-(dimethylamino)ethyl]-7-oxo-5,6,7,8-tetrahydroindolo[2,1-a][2,5]benzodiazocine-11-carboxylic acid; 14-cyclohexyl-5,6,7,8-tetrahydroindolo[2,1-a][2,5]benzodiazocine-11-carboxylic acid; 6-allyl-14-cyclohexyl-3-methoxy-5,6,7,8-tetrahydroindolo[2,1-a][2,5]benzodiazocine-11-carboxylic acid; 14-cyclopentyl-6-[2-(dimethylamino)ethyl]-5,6,7,8-tetrahydroindolo[2,1-a][2,5]benzodiazocine-11-carboxylic acid; 14-cyclohexyl-6-[2-(dimethylamino)ethyl]-5,6,7,8-tetrahydroindolo[2,1-a][2,5]benzodiazocine-11-carboxylic acid; 13-cyclohexyl-5-methyl-4,5,6,7-tetrahydrofuro[3',2':6,7][1,4]diazocino[1,8-a]indole-10-carboxylic acid; 15-cyclohexyl-6-[2-(dimethylamino)ethyl]-7,6,7,8,9-tetrahydro-5H-indolo[2,1-a][2,6]benzodiazonine-12-carboxylic acid; 15-cyclohexyl-8-oxo-6,7,8,9-tetrahydro-5H-indolo[2,1-a][2,5]benzodiazonine-12-carboxylic acid; 13-cyclohexyl-6-oxo-6,7-dihydro-5H-indolo[1,2-d][1,4]benzodiazepine-10-carboxylic acid; and pharmaceutically acceptable salts thereof.

In another embodiment, the present HCV NS5B polymerase inhibitors are used in combination with non-nucleoside HCV NS5A inhibitors and pharmaceutically acceptable salts thereof.

The HCV NS5B inhibitory activity of the present compounds may be tested using assays known in the art. The HCV NS5B polymerase inhibitors described herein have activities in a genotype 1b replicon assay as described in the Examples. The assay is performed by incubating a replicon harboring cell-line in the presence of inhibitor for a set period of time and measuring the effect of the inhibitor on HCV replicon replication either directly by quantifying replicon RNA level, or indirectly by measuring enzymatic activity of a co-encoded reporter enzyme such as luciferase or β-lactamase. By performing a series of such measurements at different inhibitor concentrations, the effective inhibitory concentration of the inhibitor ($EC_{50}$ or $EC_{90}$) is determined See Jan M. Vrolijk et al., *A replicons-based bioassay for the measurement of interferons in patients with chronic hepatitis C*, 110 J. VIROLOGICAL METHODS 201 (2003). Such assays may also be run in an automated format for high through-put screening. See Paul Zuck et al., *A cell-based β-lactamase reporter gene assay for the identification of inhibitors of hepatitis C virus replication*, 334 ANALYTICAL BIOCHEMISTRY 344 (2004).

The present invention also includes processes for making compounds of formula I. The compounds of the present invention can be readily prepared according to the following reaction schemes and examples, or modifications thereof, using readily available starting materials, reagents and conventional synthesis procedures. In these reactions, it is also possible to make use of variants which are themselves known to those of ordinary skill in this art, but are not mentioned in greater detail. Furthermore, other methods for preparing compounds of the invention will be readily apparent to the person of ordinary skill in the art in light of the following reaction schemes and examples. Unless otherwise indicated, all variables are as defined above. The following reaction schemes and examples serve only to illustrate the invention and its practice.

GENERAL SCHEMES

The Compounds of Formula (I) may be prepared from known or readily prepared starting materials, following methods known to one skilled in the art of organic synthesis. Methods useful for making the Compounds of Formula (I) are set forth in the Examples below and generalized in Schemes 1-4 below. Alternative synthetic pathways and analogous structures will be apparent to those skilled in the art of organic synthesis. All stereoisomers and tautomeric forms of the compounds are contemplated.

Some commercially available starting materials and intermediates used for the synthesis of the Compounds of Formula (I) are available. These starting materials and intermediates are available from commercial suppliers such as Sigma-Aldrich (St. Louis, Mo.) and Acros Organics Co. (Fair Lawn, N.J.). Such starting materials and intermediates compounds are used as received.

Scheme 1 shows methods useful for making the intermediates of formula C and D, which can be converted to Compounds of Formula (I).

Scheme 1

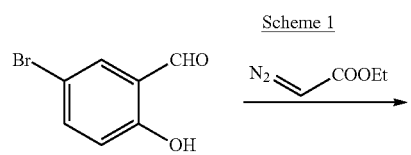

-continued

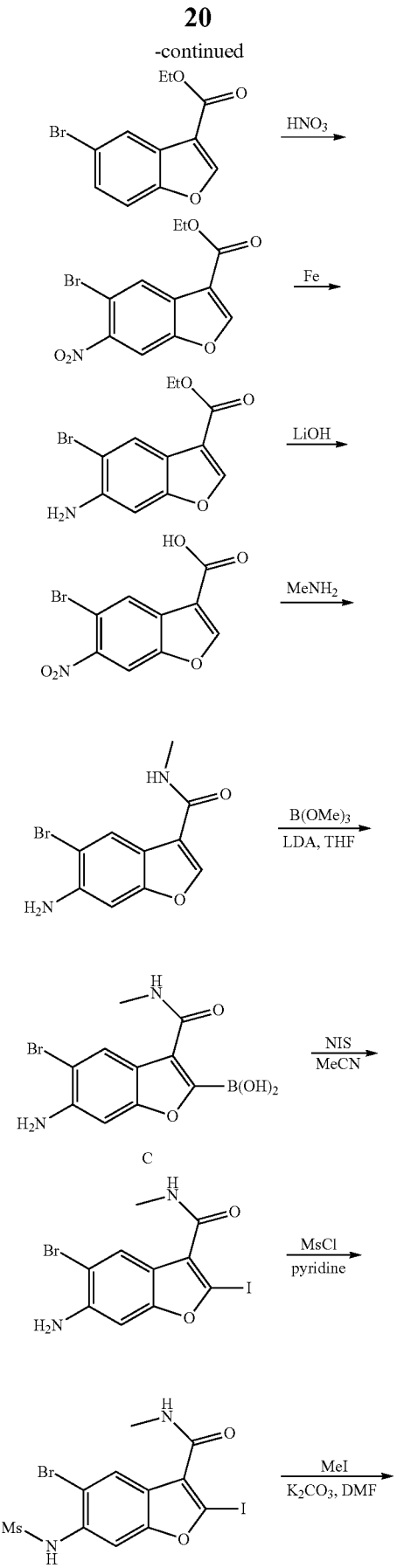

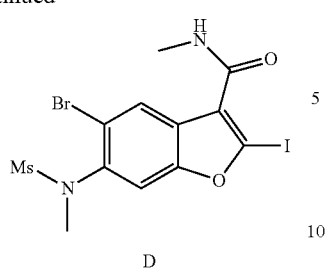

D

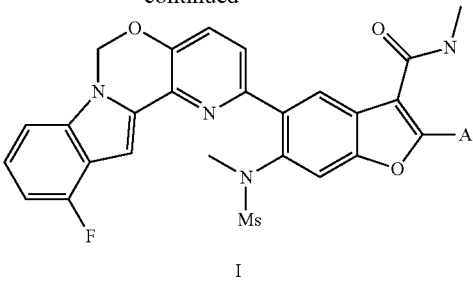

I

Scheme 2 shows a method useful for converting intermediate of formula C to Compounds of formula (I).

Alternatively, Scheme 3 shows a method useful for converting intermediate of formula D to Compounds of formula (I). Moiety A was introduced by either Suzuki coupling reaction or C—N coupling reaction or carbonylation reaction (followed by further transformations).

Scheme 3

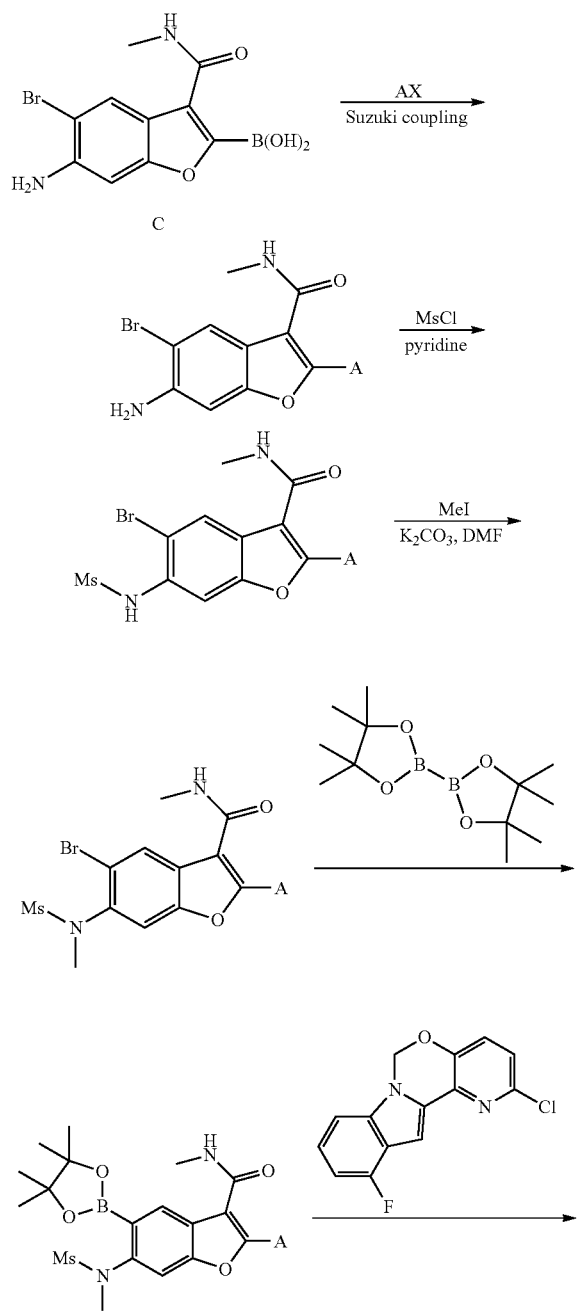

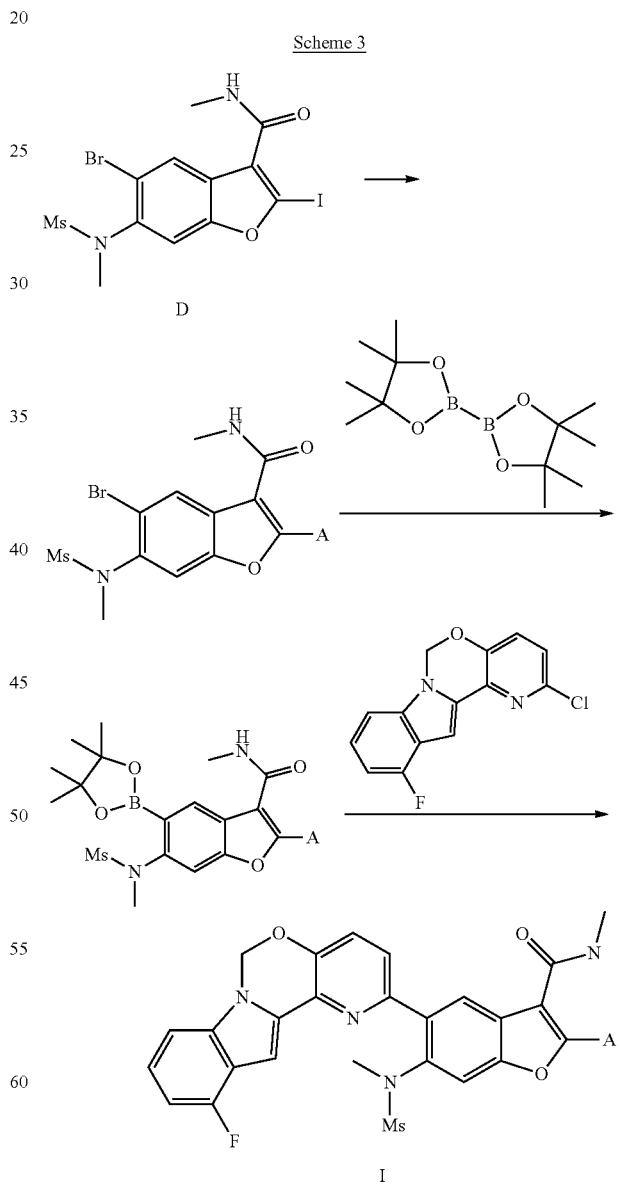

Alternatively, Scheme 4 shows a method useful for synthesizing Compound of formula (I) by Stille coupling reaction.

Scheme 4

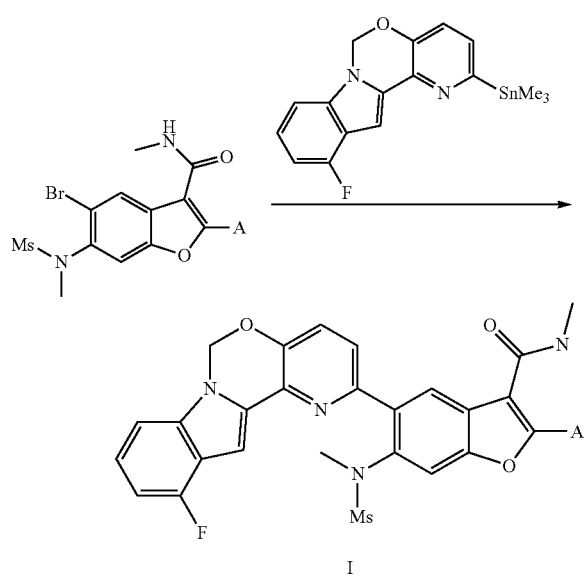

I

LIST OF ABBREVIATIONS a.q. Aqueous
$Ar_2$ Argon gas
Boc t-butyloxycarbonyl
$Boc_2O$ Di-tert-butyl-dicarbonate
$B(OMe)_3$ Trimethoxyborane
$Br_2$ Bromine
n-BuLi n-butyllithium
conc. concentrated
$CDCl_3$ Trichloro($^2$H)methane or deuterio-trichloromethane
$CHCl_3$ Chloroform
$CH_3COOK$ Potassium acetate
$CH_2I_2$ Methylene iodide
CO Carbon monoxide
$Cs_2CO_3$ Cesium carbonate
DAST Diethylaminosulfur trifluoride
DCM, $CH_2Cl_2$ Dichloromethane
DDQ Dichlorodicyanoquinone
DMAP 4-dimethylaminopyridine
DMF Dimethylformamide
DMSO Dimethylsulfoxide
EDCI N-(3-Dimethylaminopropyl)-N'-ethylcarbodiimide (also EDC)
Et Ethyl
$Et_3N$ Triethylamine
$Et_2O$ Diethylether
EtOAc, EA Ethyl acetate
EtOH, $CH_3CH_2OH$ Ethanol
$F_2ClCCOONa$ Sodium chlorodifluoroacetate
Fe Iron
FeCl Iron chloride
$HBF_4$ Fluoroboric acid
HBr Hydrogen bromide
HCl Hydrochloric acid
$H_2$ Hydrogen gas or atmosphere
$HNO_3$ Nitric acid
$H_2O$ Water
$H_2SO_4$ Sulfuric acid
HOAc Acetic acid
HOBT 1-Hydroxy benzotriazole
$^1$H-NMR Proton Nuclear Magnetic Resonance
HPLC High Performance Liquid Chromatography
IPA Isopropyl alcohol
$K_2CO_3$ Potassium carbonate
KOAc Potassium acetate
$K_2HPO_4$ Dipotassium phosphate
$K_3PO_4$ Potassium Phosphate
LDA Lithium diisopropylamide
LiCl Lithium chloride
LiOH Lithium hydroxide
$MeNH_2$, $CH_3NH_2$ Methanamine
MeCN, $CH_3CN$ Acetonitrile
Met, $CH_3I$ Methyl iodide
MeOD Methan($^2$H)ol
MeOH, $CH_3OH$ Methanol
$(Me_3Sn)_2$ Hexamethylditin
MS Mass spectroscopy
Ms Methanesulfonyl (or mesyl) group
MsCl Methanesulfonyl chloride
$N_2$ Nitrogen gas or atmosphere
$NaBH_4$ Sodium borohydride
$Na_2CO_3$ Sodium carbonate
NaF Sodium fluoride
$NaHCO_3$ Sodium bicarbonate
NaI Sodium iodide
$Na_2SO_4$ Sodium sulfate (anhydrous)
$NH_4Cl$ Ammonium chloride
NIS N-iodosuccinimide
$OPPh_3$ Triphenyl phosphine
Pd Palladium
$Pd_2(dba)_3$ Tris(dibenzylideneacetone)dipalladium(0)
$Pd(dppf)Cl_2$ 1,1'-bis(diphenylphosphino)ferrocene-palladium(II)dichloride
$Pd(dtbpf)Cl_2$ 1,1'-bis(di-tert-butylphosphino)ferrocene-dichloropalladium(II)
$Pd(OAc)_2$ Palladium(II)acetate
$Pd(PPh_3)_2Cl_2$ 1,1'-bis(tetrakis(triphenylphosphine))palladium(II)dichloride
PE Petroleum ether
Ph Phenyl
PPA Polyphosphoric acid
RT Room temperature, approximately 25° C.
sat saturated
SFC Supercritical fluid chromatography
p-TsCl p-toluenesulfonyl chloride
TEA Triethylamine
TFA Trifluoroacetic acid
THF Tetrahydrofuran
TLC Thin layer chromatography
$ZnEt_2$ Diethylzinc

EXAMPLES

Example 1

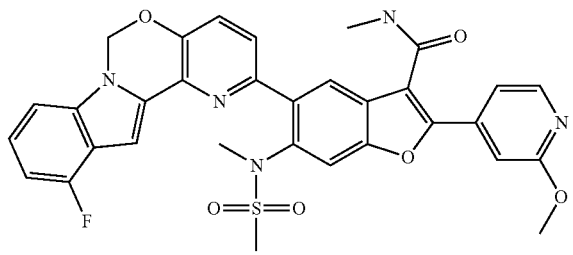 [SMILES: CNC(=O)c1c(-c2ccnc(OC)c2)oc2cc(N(C)S(C)(=O)=O)c(-c3ccc4c(n3)-c3cc5c(F)cccc5n3CO4)cc12]

Step 1 - Synthesis of ethyl 5-bromobenzofuran-3-carboxylate

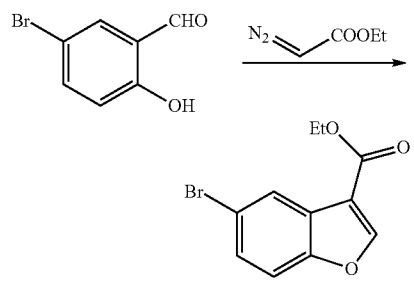

HBF$_4$.Et$_2$O (16.2 g, 99.5 mmol) was added to a solution of 5-bromo-2-hydroxybenzaldehyde (200 g, 995 mmol) in CH$_2$Cl$_2$ (500 mL), and then a solution of ethyl diazoacetate (180 g, 1.42 mol) in CH$_2$Cl$_2$ (500 mL) was introduced as evolution of N$_2$ gas while the reaction was not allowed over 38° C. Once gas evolution ceased, the reaction mixture was concentrated by rotary evaporator and conc. H$_2$SO$_4$ (129 g, 1.29 mol, 98%) was added to the mixture while stirring. After 20 minutes, the acidic mixture was neutralized with Na$_2$CO$_3$ (a.q.). After the mixture was stored and crystallized overnight, ethyl 5-bromobenzofuran-3-carboxylate (100 g, yield: 75%) was obtained by filtration. $^1$H-NMR (400 MHz, CDCl$_3$) δ 8.25 (s, 1H), 8.15~8.21 (m, 1H), 7.44~7.50 (m, 1H), 7.37~7.42 (m, 1H), 4.41 (q, J=7.2 Hz, 2H), 1.43 (t, J=7.2 Hz, 3H).

Step 2 - Synthesis of ethyl 5-bromo-6-nitrobenzofuran-3-carboxylate

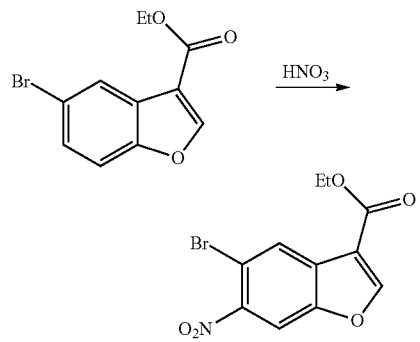

To a solution of ethyl 5-bromobenzofuran-3-carboxylate (95 g, 353 mmol) in CHCl$_3$ (1000 mL), fuming HNO$_3$ (192 mL, 95%) was added dropwise at −20° C. over 90 min and stirred at 0° C. for 1 hour. The reaction mixture was added to ice water and extracted with CH$_2$Cl$_2$. The organic layer was washed with NaHCO$_3$ and brine. The solvent was removed by distillation to provide the crude product of ethyl 5-bromo-6-nitrobenzofuran-3-carboxylate (95 g, yield: 85%). It was used for the next step without further purification.

Step 3 - Synthesis of ethyl 6-amino-5-bromobenzofuran-3-carboxylate

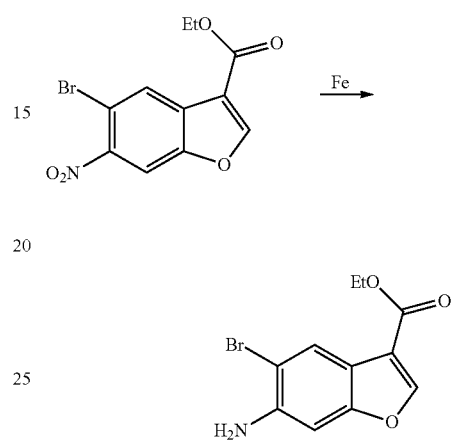

A mixture of crude compound ethyl 5-bromo-6-nitrobenzofuran-3-carboxylate (95 g, 302 mmol), iron filings (50.67 g, 907 mmol) and NH$_4$Cl (97 g, 1.82 mol) in MeOH-THF—H$_2$O (2:2:1, 1000 mL) were stirred at reflux for 3 hours. After being filtered and concentrated in vacuum, the residue was purified by column chromatography (eluted with PE:EA from 20:1 to 10:1) to furnish ethyl 6-amino-5-bromobenzofuran-3-carboxylate (58.00 g, yield: 68%). $^1$H-NMR (400 MHz, DMSO-d$_6$) δ 8.46 (s, 1H), 7.85 (s, 1H), 7.03 (s, 1H), 5.55 (br s, 2H), 4.31 (q, J=7.2 Hz, 2H), 1.32 (t, J=7.2 Hz, 3H).

Step 4 - Synthesis of 6-amino-5-bromobenzofuran-3-carboxylic acid

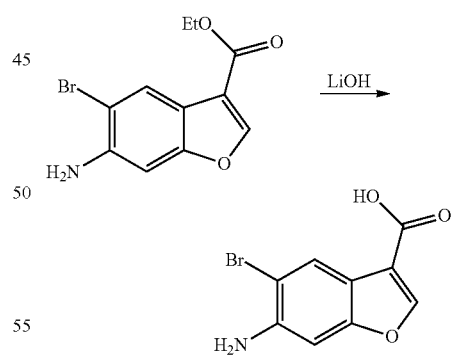

To a solution of the compound ethyl 6-amino-5-bromobenzofuran-3-carboxylate (58 g, 204 mmol) in 1,4-dioxane and H$_2$O (850 mL and 150 mL) was added LiOH.H$_2$O (42.8 g, 1.02 mol). The reaction mixture was refluxed for 2 hours, and then 400 mL H$_2$O was added to the reaction mixture. After acidifying to pH 4~5 with HCl, the resulting solid was filtered to give 6-amino-5-bromobenzofuran-3-carboxylic acid (51 g, yield: 97%). $^1$H-NMR (400 MHz, DMSO-d$_6$) δ 8.36 (s, 1H), 7.87 (s, 1H), 7.02 (s, 1H), 5.51 (br s, 2H).

Step 5 - Synthesis of 6-amino-5-bromo-N-methylbenzofuran-3-carboxamide

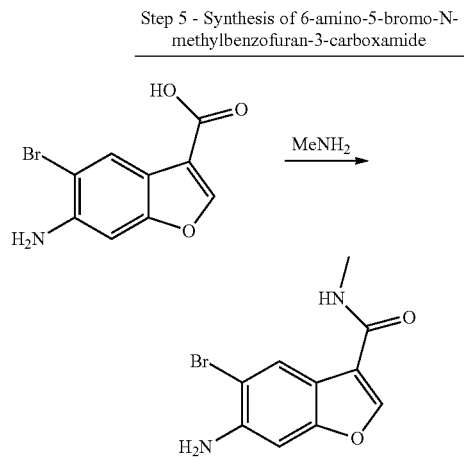

To a solution of 6-amino-5-bromobenzofuran-3-carboxylic acid (51 g, 199 mmol) in dry DMF (500 mL) were add EDCI (53.1 g, 298.77 mmol) and HOBT (40.4 g, 299 mmol). The reaction mixture was stirred at room temperature for 2 h, and then Et₃N (60.5 g, 598 mmol) and MeNH₂.HCl (40.3 g, 598 mmol) were added to the reaction mixture. After stirring for another 2 hours, the reaction mixture was concentrated in vacuum and 300 mL Na₂CO₃ (a.q.) was added to the mixture. The resulting solid was filtered to give the crude product, which was purified by column chromatography (DCM:MeOH=30:1) to give 6-amino-5-bromo-N-methylbenzofuran-3-carboxamide (38 g, yield: 71%). ¹H-NMR (400 MHz, DMSO-d₆) δ 8.19~8.21 (m, 2H), 7.98 (s, 1H), 6.97 (s, 1H), 5.46 (br s, 2H), 2.75 (d, J=4.4 Hz, 3H).

Step 6 - Synthesis of (6-amino-5-bromo-3-(methylcarbamoyl)benzofuran-2-yl)boronic acid

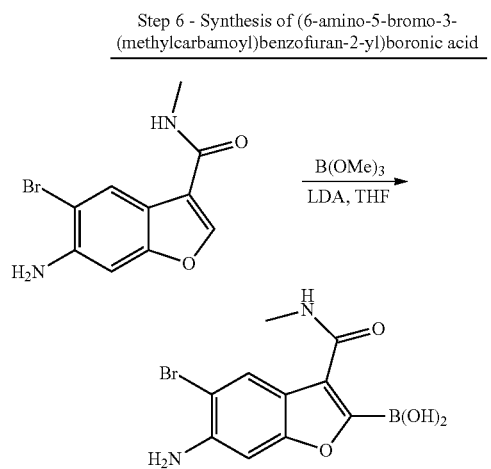

To a solution of LDA in THF (62.5 mmol, 70 mL, freshly prepared), 6-amino-5-bromo-N-methylbenzofuran-3-carboxamide (4 g, 14.86 mmol) in THF (60 mL) was added dropwise at −78° C. under N₂. After the mixture was stirred for 1 hour, trimethyl borate (6.18 g, 59.5 mmol) was added dropwise at −78° C. After the mixture was stirred for 1 hour, NH₄Cl (a.q.) was added, and the mixture was extracted with EtOAc (100 mL×3), dried over Na₂SO₄, filtrated and concentrated to give (6-amino-5-bromo-3-(methylcarbamoyl)benzofuran-2-yl)boronic acid (3.3 g, yield: 70%). ¹H-NMR (DMSO-d₆, 400 MHz) δ 9.56 (s, 2H), 8.46 (d, J=4.8 Hz, 1H), 8.00 (s, 1H), 6.95 (s, 1H), 5.20~5.82 (br s, 2H), 2.87 (d, J=4.8 Hz, 3H). MS (M+H)⁺: 313/315.

Step 7 - Synthesis of 6-amino-5-bromo-2-iodo-N-methylbenzofuran-3-carboxamide

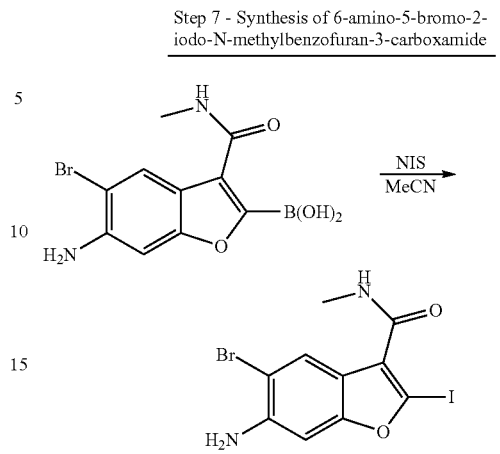

To a solution of (6-amino-5-bromo-3-(methylcarbamoyl)benzofuran-2-yl)boronic acid (2 g, 6.4 mmol) in MeCN (20 mL) was added NIS (1.44 g, 6.4 mmol) at 0° C., and then the mixture was stirred at 25° C. overnight. After being concentrated in vacuum, the residue was purified by column chromatography (DCM:EtOAc=10:1) to give to give pure 6-amino-5-bromo-2-iodo-N-methylbenzofuran-3-carboxamide (2 g, yield: 80%). ¹H-NMR (CDCl₃, 400 MHz) δ 7.84 (s, 1H), 6.80 (s, 1H), 6.45 (s, 1H), 2.92 (s, 3H). MS (M+H)⁺: 395/397.

Step 8 - Synthesis of 5-bromo-2-iodo-N-methyl-6-(methylsulfonamido)benzofuran-3-carboxamide

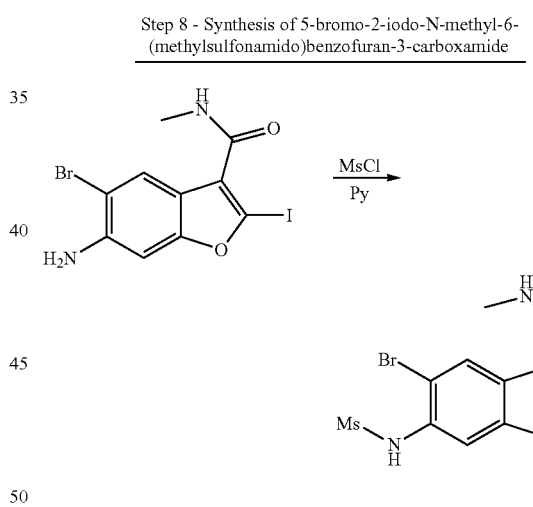

To a solution of 6-amino-5-bromo-2-iodo-N-methylbenzofuran-3-carboxamide (1 g, 2.53 mmol) in pyridine, MsCl (580 mg, 5.06 mmol) was added dropwise at 0° C. The mixture was allowed to warm to room temperature and stirred for 1.5 h. After the solvent was removed, the reaction mixture was adjusted to pH=5-6 with 1 N HCl. After filtration, the solid was dissolved in THF:H₂O=5:1 (15 mL) and then LiOH.H₂O (800 mg, 20 mmol) was added. The mixture was stirred for 30 minutes at room temperature. After the solvent was removed, the reaction mixture was adjusted to pH=5-6 with 1 N HCl. Finally the precipitate was collected to give 5-bromo-2-iodo-N-methyl-6-(methylsulfonamido)benzofuran-3-carboxamide (800 mg, 90% purity by HPLC, yield: 60%), which was used for the next step without further purification. ¹H-NMR (CDCl₃, 400 MHz) δ 8.37 (s, 1H), 7.84 (s, 1H), 6.86 (s, 1H), 6.29 (s, 1H), 3.07 (d, J=4.8 Hz, 3H), 2.99 (s, 3H). MS (M+H)⁺: 473/475.

Step 9 - Synthesis of 5-bromo-2-iodo-N-methyl-6-(N-methylmethylsulfonamido)benzofuran-3-carboxamide

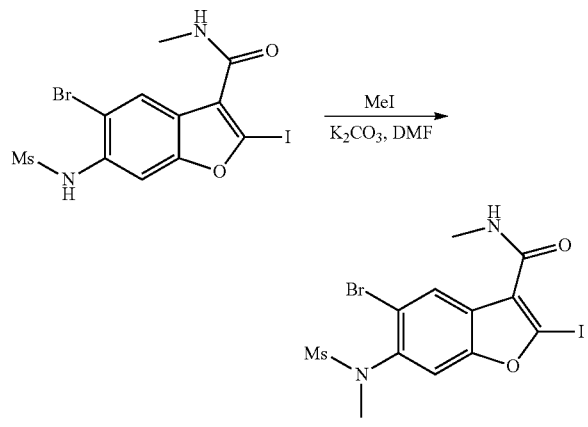

To a suspension of 5-bromo-2-iodo-N-methyl-6-(methylsulfonamido)benzofuran-3-carboxamide (177 mg, 90% purity, 0.34 mmol) and K₂CO₃ (140 mg, 1.01 mmol) in DMF (3 mL) was added dropwise CH₃I (79 mg, 0.68 mol) at 0° C. under N₂, and then the mixture was stirred at 80° C. for 1 hour. After concentrated in vacuum, the residue was suspended in H₂O and extracted with DCM. The residue was purified by column chromatography (eluted with DCM:EtOAc from 10:1 to 2:1) to give 5-bromo-2-iodo-N-methyl-6-(N-methylmethylsulfonamido)benzofuran-3-carboxamide (150 mg, yield: 90%). ¹H-NMR (CDCl₃, 400 MHz) δ 8.38 (s, 1H), 7.66 (s, 1H), 6.27 (s, 1H), 3.32 (s, 3H), 3.08 (d, J=4.8 Hz, 3H), 2.89 (s, 3H). MS (M+H)⁺: 487/489.

Step 10 - Synthesis of 5-bromo-2-(2-methoxypyridin-4-yl)-N-methyl-6-(N-methylmethylsulfonamido)benzofuran-3-carboxamide

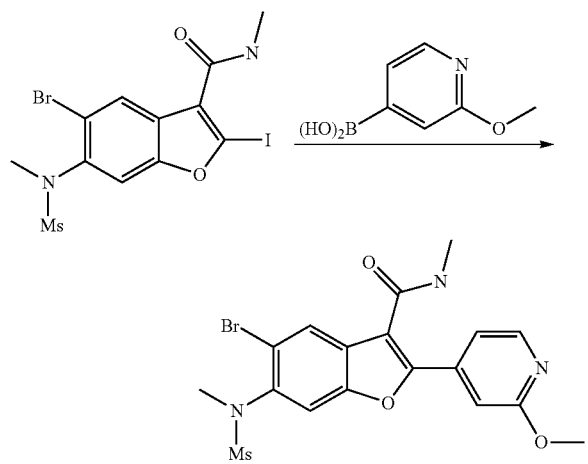

To a N₂ degassed solution of 5-bromo-2-iodo-N-methyl-6-(N-methylmethylsulfonamido)benzofuran-3-carboxamide (300 mg, 0.3 mmol), (2-methoxypyridin-4-yl)boronic acid (94 mg, 0.3 mmol) and K₂CO₃ (195 mg, 0.9 mmol) in DMF (4 mL) was added Pd(dppf)Cl₂ (5 mg) under N₂. The mixture was stirred at 100° C. for 1 h. After the solvent was removed, the residue was purified by prep-TLC (DCM:EtOAc=5:1) to give the product of compound 2 (150 mg, yield: 52%). ¹H-NMR (CDCl₃, 400 MHz) δ 8.29 (d, J=5.6 Hz, 1H), 8.10 (s, 1H), 7.71 (s, 1H), 7.32~7.34 (m, 1H), 7.22 (s, 1H), 5.96 (s, 1H), 3.98 (s, 3H), 3.33 (s, 3H), 3.09 (s, 3H), 3.02 (d, J=4.8 Hz, 3H). MS (M+H)⁺: 468/470.

Step 11 - Synthesis of 2-(2-methoxypyridin-4-yl)-N-methyl-6-(N-methylmethylsulfonamido)-5-(4,4,5,5-tetramethyl-1,3,2-dioxaborolan-2-yl)benzofuran-3-carboxamide

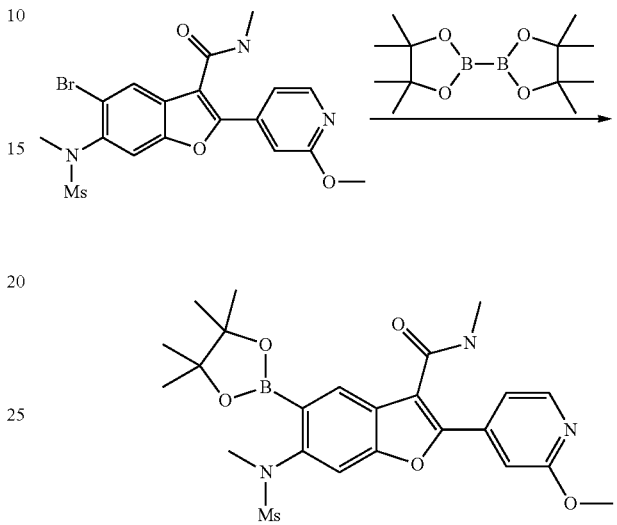

To a N₂ degassed solution of 5-bromo-2-(2-methoxypyridin-4-yl)-N-methyl-6-(N-methylmethylsulfonamido)benzofuran-3-carboxamide (150 mg, 0.3 mmol), KOAc (94 mg, 0.9 mmol) and bis(pinacolato)diboron (411 mg, 1.6 mmol) in dioxane (5 mL) and H₂O (0.1 mL) was added Pd(dppf)Cl₂ (3 mg) under N₂, and the mixture was stirred at 130° C. for 3 hours. After the solvent was removed, the residue was purified by prep-TLC (DCM:EtOAc=5:1) to give the product of 2-(2-methoxypyridin-4-yl)-N-methyl-6-(N-methylmethylsulfonamido)-5-(4,4,5,5-tetramethyl-1,3,2-dioxaborolan-2-yl)benzofuran-3-carboxamide (120 mg, yield: 72%). ¹H-NMR (CDCl₃, 400 MHz) δ 8.26 (d, J=5.6 Hz, 1H), 8.20 (s, 1H), 7.59 (s, 1H), 7.38~7.41 (m, 1H), 7.29 (s, 1H), 6.04 (s, 1H), 3.97 (s, 3H), 3.36 (s, 3H), 3.06 (d, J=4.8 Hz, 3H), 2.95 (s, 3H), 1.36 (s, 12H). MS (M+H)⁺: 516.

Step 12 - Synthesis of tert-butyl 4-fluoro-1H-indole-1-carboxylate

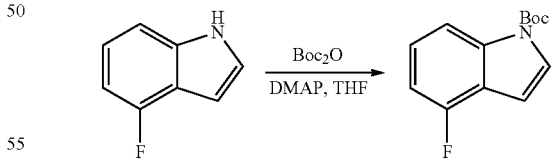

To a solution of 4-fluoro-1H-indole (150 g, 1.11 mol) and DMAP (4.5 g, 3% Wt) in THF (2.5 L) was added (Boc)₂O (255 g, 1.16 mol) dropwise. The mixture was stirred at room temperature overnight. The organic solvent was removed in vacuum, and the residue was purified by column chromatography (PE) to give tert-butyl 4-fluoro-1H-indole-1-carboxylate (250 g, yield: 96%). ¹H-NMR (CDCl₃, 400 MHz) δ 7.92 (d, J=8.4 Hz, 1H), 7.55 (d, J=3.6 Hz, 1H), 7.23 (m, 1H), 6.90 (m, 1H), 6.66 (d, J=3.6 Hz, 1H), 1.67 (s, 9H). MS (M+H)⁺: 236.

Step 13 - Synthesis of (1-(tert-butoxycarbonyl)-4-fluoro-1H-indole-2-yl)boronic acid

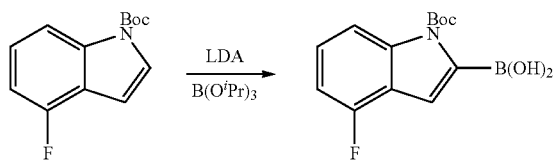

To a solution of diisopropylamine (175 mL, 1.25 mol) in THF (800 mL) at 0° C. was added n-BuLi (500 mL, 1.25 mol) dropwise. The mixture was stirred at 0° C. for 40 min. Then the mixture was cooled to −78° C. Tert-butyl 4-fluoro-1H-indole-1-carboxylate (118 g, 0.50 mol) in THF (300 mL) was added dropwise slowly, followed by triisopropyl borate (231 mL, 1.00 mol). The mixture was stirred at −78° C. for another 40 min. The reaction was monitored by HPLC. When the reaction was completed, the reaction was quenched with NH$_4$Cl (sat. 500 mL). Then the mixture was adjusted to pH=6 with 1 N HCl. Extracted with EtOAc (2000 mL) and the combined organic layers were washed with brine (500 mL), dried over Na$_2$SO$_4$, filtered and concentrated. The obtained solid was recrystallized with EtOAc and PE to give (1-(tert-butoxycarbonyl)-4-fluoro-1H-indol-2-yl)boronic acid (93 g, yield: 64%, store in fridge). $^1$H-NMR (CDCl$_3$, 400 MHz) δ 7.77 (d, J=8.4 Hz, 1H), 7.57 (s, 1H), 7.44 (s, 2H), 7.24 (m, 1H), 6.90 (m, 1H), 1.66 (s, 9H). MS (M+H)$^+$: 280.

Step 14 - Synthesis of 4-fluoro-1H-indol-2-ylboronic acid

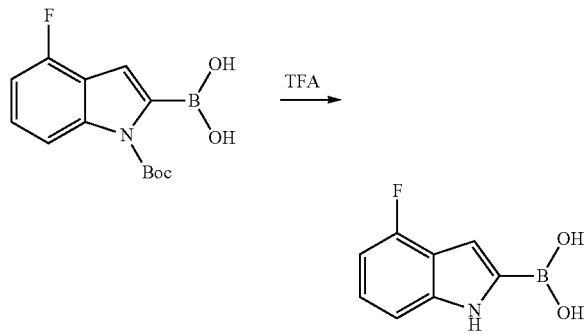

TFA (60 mL) was added 1-(tert-butoxycarbonyl)-4-fluoro-1H-indol-2-ylboronic acid (10 g, 35.83 mmol) in portions at 0° C. and then the mixture was stirred at room temperature for 3 hours. The mixture was poured into ice water, stirred for 10 minutes and filtered through a pad to give the crude 4-fluoro-1H-indol-2-ylboronic acid (6.0 g, yield: 94%) without further purification. $^1$H-NMR (DMSO-d$_6$, 400 MHz) δ 11.09 (s, 1H), 8.35 (br s, 2H), 7.22 (d, J=8.00 Hz, 1H), 7.02~7.07 (m, 2H), 6.68~6.72 (m, 1H). MS (M+H)$^+$: 180.

Step 15 - Synthesis of 6-chloro-2-iodopyridin-3-ol 6-chloropyridin-3-ol (5.0 g, 38.6 mmol) was dissolved in water (50 mL) and placed under an N$_2$ atmosphere. Na$_2$CO$_3$ (8.2 g, 77.4 mmol) was added followed by iodine (9.8 g, 38.8 mmol). The reaction mixture was stirred at room temperature for 2 hours. The mixture was poured into 1M Na$_2$S$_2$O$_3$ and extracted with EtOAc. The combined organic phases were washed with brine, dried over Na$_2$SO$_4$ and concentrated to give the product of 6-chloro-2-iodopyridin-3-ol (7.0 g, yield: 70.9%). $^1$H-NMR (CDCl$_3$, 400 MHz) δ 7.17 (d, J=8.4 Hz, 1H), 7.06 (d, J=8.4 Hz, 1H). MS (M+H)$^+$: 256/258.

Step 16 - Synthesis of 6-chloro-2-(4-fluoro-1H-indol-2-yl)pyridin-3-ol

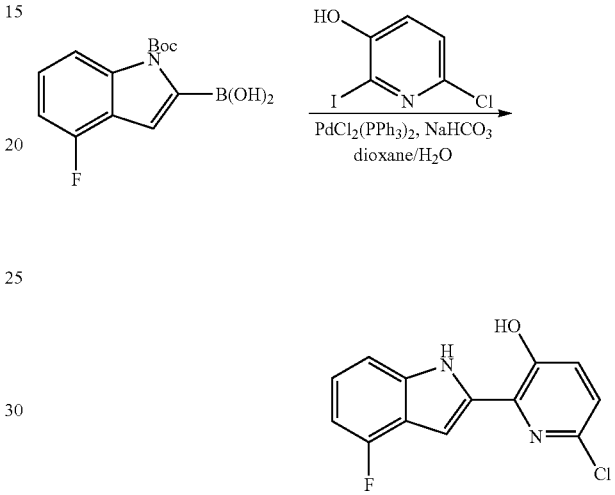

A mixture of (1-(tert-butoxycarbonyl)-4-fluoro-1H-indol-2-yl)boronic acid (5 g, 18.0 mmol), 6-chloro-2-iodopyridin-3-ol (3.82 g, 15.0 mol) and NaHCO$_3$ (3.78 g, 45.0 mol) in 1,4-dioxane (76 mL) and water (7 mL) was stirred at room temperature for 15 min. Then Pd(PPh$_3$)$_2$Cl$_2$ (527 mg, 0.75 mmol) was added under nitrogen atmosphere, and the mixture was heated at 100° C. under N$_2$ for 16 hours. The reaction mixture was cooled to room temperature, diluted with EtOAc (50 mL), filtered and concentrated. The residue was diluted with H$_2$O (60 mL) and EtOAc (30 mL), and the layer was separated, the aqueous layer was extracted with EtOAc (3*30 mL). The combined organic layers were washed with brine (50 mL), dried over Na$_2$SO$_4$, filtered and concentrated. The residue was purified by column chromatography (PE/EtOAc=20/1~3/1) to give 6-chloro-2-(4-fluoro-1H-indol-2-yl)pyridin-3-ol (3 g, yield: 76.5%). $^1$H-NMR (MeOD, 400 MHz) δ 7.36 (s, 1H), 7.23~7.27 (m, 2H), 7.03~7.11 (m, 2H), 6.6~36.68 (m, 1H). MS (M+H)$^+$: 263/265.

Step 17 - Synthesis of 2-chloro-11-fluoro-6H-pyrido[2′,3′:4,5][1,3]oxazino[3,4-a] indole

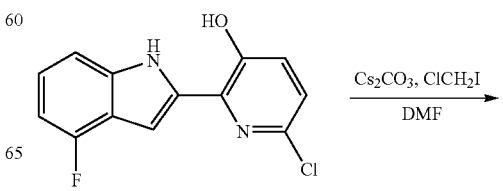

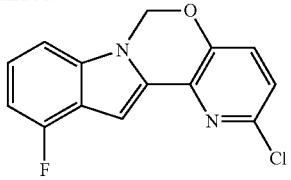

A solution of 6-chloro-2-(4-fluoro-1H-indol-2-yl)pyridin-3-ol (2 g, 7.6 mmol) and Cs₂CO₃ (7.46 g, 22.89 mmol) in DMF (100 mL) was stirred at 100° C. (internal temperature) for 15 min, and then chloroiodomethane (2.85 g, 15.3 mmol) in DMF (2 mL) was added dropwise.

After the reaction was completed, the mixture was filtered and concentrated. The residue was diluted with water (50 mL) and extracted with EA (30 mL*3). The organic layer was washed with brine, dried over Na₂SO₄ and concentrated. The residue was purified by column chromatography (PE:EA=10:1) to afford 2-chloro-11-fluoro-6H-pyrido[2',3':5,6][1,3]oxazino[3,4-a]indole (1.8 g, yield: 86.1%). ¹H-NMR (DMSO-d₆, 400 MHz) δ 7.64 (d, J=8.8 Hz, 1H), 7.39~7.46 (m, 2H), 7.21~7.25 (m, 1H), 7.06 (s, 1H), 6.88~6.92 (m, 1H), 6.18 (s, 2H). MS (M+H)⁺: 275/277.

To a degassed solution of 2-(2-methoxypyridin-4-yl)-N-methyl-6-(N-methylmethylsulfonamido)-5-(4,4,5,5-tetramethyl-1,3,2-dioxaborolan-2-yl)benzofuran-3-carboxamide (60 mg, 0.12 mmol), 2-chloro-11-fluoro-6H-pyrido[2',3':5,6][1,3]oxazino[3,4-a]indole (35 mg, 0.13 mmol) and Na₂CO₃ (25 mg, 0.23 mmol) in dioxane (1.5 mL) and H₂O (0.1 mL) was added Pd₂(dba)₃ (3 mg) and X-Phos (3 mg) under N₂. Then the mixture was stirred at 100° C. for 2 hours. The reaction mixture was cooled to RT and filtered. The filtrate was washed with H₂O and dried over Na₂SO₄. After concentrated, the residue was purified by prep-HPLC to give the product of 5-(11-fluoro-6H-pyrido[2',3':5,6][1,3]oxazino[3,4-a]indol-2-yl)-2-(2-methoxypyridin-4-yl)-N-methyl-6-(N-methylmethylsulfonamido)benzofuran-3-carboxamide (35 mg, yield: 48%). ¹H-NMR (CDCl₃, 400 MHz) δ 8.29 (s, 1H), 8.28 (s, 1H), 7.98 (s, 1H), 7.69 (s, 2H), 7.40~7.49 (m, 1H), 7.30 (s, 1H), 7.19~7.24 (m, 2H), 7.10~7.18 (m, 1H), 6.82~6.87 (m, 1H), 6.11 (s, 1H), 5.99 (s, 2H), 3.99 (s, 3H), 3.36 (s, 3H), 3.04 (d, J=4.8 Hz, 3H), 2.75 (s, 3H). MS (M+H)⁺: 628.

Examples 2-16

Examples 2-16, depicted in the table below, were prepared in accordance with the method described in Example 1.

Step 18 - Synthesis of 5-(11-fluoro-6H-pyrido[2',3':4,5][1,3]oxazino[3,4-a]indol-2-yl)-2-(2-methoxypyridin-4-yl)-N-methyl-6-(N-methylmethylsulfonamido)benzofuran-3-carboxamide
(Example 1)

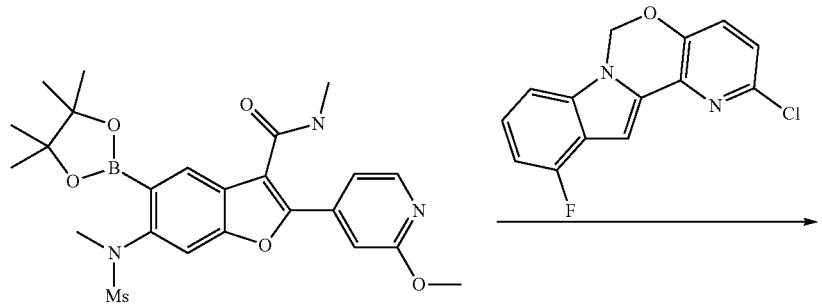

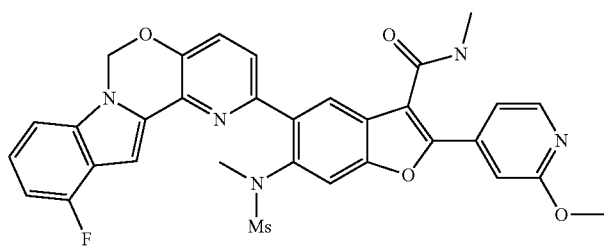

| Example | Structure | NMR | MS (M + H)+ |
|---|---|---|---|
| 2 | 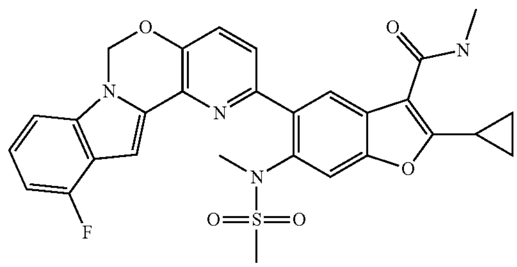 [SMILES: CNC(=O)c1c(C2CC2)oc2cc(N(C)S(C)(=O)=O)c(-c3ccc4c(n3)-c3cc5c(F)cccc5n3CO4)cc12] | ¹H-NMR (CDCl₃, 400 MHz) δ 7.85 (s, 1H), 7.85 (s, 1H), 7.49 (d, J = 2.4 Hz, 2H), 7.21 (s, 1H), 7.19~7.26 (m, 2H), 6.85~6.81 (m, 1H), 6.13 (s, 1H), 5.97 (s, 2H), 3.13 (s, 3H), 3.02 (d, J = 4.8 Hz, 3H), 2.81 (s, 3H), 2.03~1.96 (m, 1H), 1.24~1.22 (m, 2H), 1.18-4.16 (m, 2H). | 561 |
| 3 | 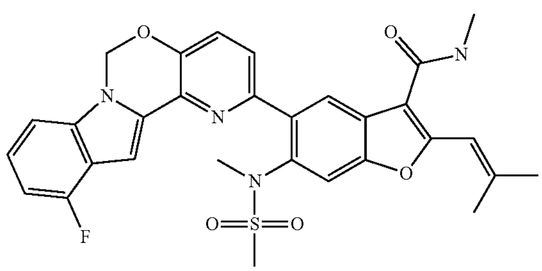 [SMILES: CNC(=O)c1c(C=C(C)C)oc2cc(N(C)S(C)(=O)=O)c(-c3ccc4c(n3)-c3cc5c(F)cccc5n3CO4)cc12] | ¹H-NMR (CDCl₃, 400 MHz) δ 7.89 (s, 1H), 7.54 (s, 1H), 7.38~7.46 (m, 2H), 7.11~7.16 (m, 2H), 7.03 (d, J = 8.4 Hz, 1H), 6.75~6.80 (m, 1H), 6.62 (s, 1H), 5.91~5.93 (m, 3H), 3.28 (s, 3H), 2.95 (d, J = 4.8 Hz, 3H), 2.67 (s, 3H), 2.14 (s, 3H), 1.98 (s, 3H). | 575 |
| 4 | 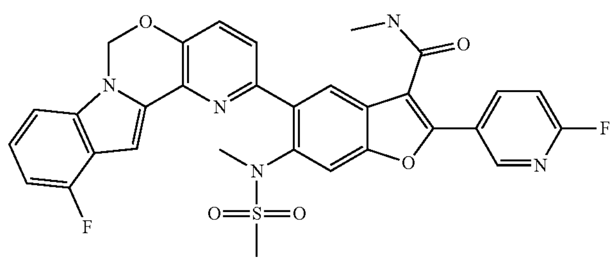 [SMILES: CNC(=O)c1c(-c2ccc(F)nc2)oc2cc(N(C)S(C)(=O)=O)c(-c3ccc4c(n3)-c3cc5c(F)cccc5n3CO4)cc12] | ¹H-NMR (CDCl₃, 400 MHz) δ 8.78 (s, 1H), 8.47~8.52 (m, 1H), 7.89 (s, 1H), 7.63 (s, 1H), 7.42~7.46 (m, 2H), 7.13~7.18 (m, 2H), 6.99~7.06 (m, 2H), 6.76~6.81 (m, 1H), 6.06 (d, J = 4.4 Hz, 1H), 5.94 (s, 2H), 3.29 (s, 3H), 2.97 (d, J = 4.8 Hz, 3H), 2.72 (s, 3H). | 616 |
| 5 | 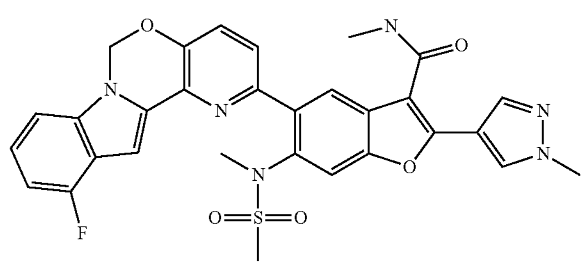 [SMILES: CNC(=O)c1c(-c2cnn(C)c2)oc2cc(N(C)S(C)(=O)=O)c(-c3ccc4c(n3)-c3cc5c(F)cccc5n3CO4)cc12] | ¹H-NMR (DMSO-d₆, 400 MHz) δ 8.45 (s, 1H), 8.29 (d, J = 8.0 Hz,, 1H), 8.04 (s, 1H ), 7.93 (s, 1H ), 7.83 (s, 1H), 7.68 (d, J = 8.8 Hz, 1H), 7.59 (d, J = 8.4 Hz, 1H), 7.48 (d, J = 8.0 Hz, 1H), 7.23 (d, J = 8.0 Hz, 1H), 7.08 (s, 1H), 6.88-6.93 (m, 1H), 6.24 (s, 2H), 3.92 (s, 3H), 3.27 (s, 3H), 2.91 (s, 3H), 2.81 (d, J = 4.4 Hz, 3H). | 601 |
| 6 | 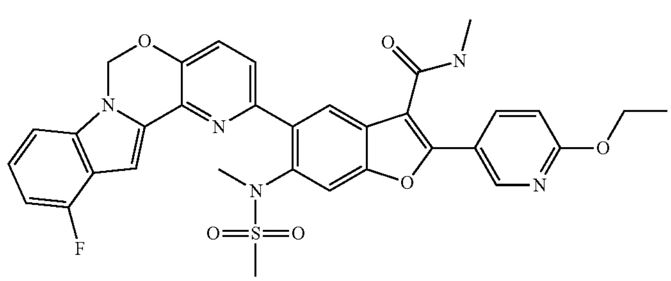 [SMILES: CCOc1ccc(-c2oc3cc(N(C)S(C)(=O)=O)c(-c4ccc5c(n4)-c4cc6c(F)cccc6n4CO5)cc3c2C(=O)NC)cn1] | ¹H-NMR (CDCl₃, 400 MHz) δ 8.71 (d, J = 2.4 Hz, 1H), 8.13-8.16 (m, 1H), 7.96 (s, 1H), 7.63 (s, 1H), 7.46 (s, 2H), 7.17-7.22 (m, 2H), 7.09 (d, J = 8.4 Hz, 1H), 6.81~6.86 (m, 2H), 6.12 (br s, 1H), 5.98 (s, 2H), 4.43 (q, J = 7.6 Hz, 2H), 3.35 (s, 3H), 2.98 (d, J = 4.8 Hz, 3H), 2.73 (s, 3H), 1.42 (t, J = 7.6 Hz, 3H). | 642 |
| 7 | 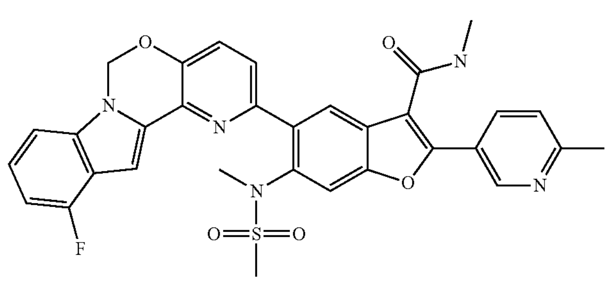 [SMILES: CNC(=O)c1c(-c2ccc(C)nc2)oc2cc(N(C)S(C)(=O)=O)c(-c3ccc4c(n3)-c3cc5c(F)cccc5n3CO4)cc12] | ¹H-NMR (CDCl₃, 400 MHz) δ 9.05 (s, 1H), 8.24 (d, J = 6.4 Hz, 1H), 8.03 (s, 1H), 7.71 (s, 1H), 7.49~7.54 (m, 2H), 7.32 (d, J = 8.0 Hz, 1H), 7.20~7.26 (m, 2H), 7.13 (d, J = 8.0 Hz, 1H), 6.83~6.89 (m, 1H), 6.02 (s, 3H), 3.38 (s, 3H), 3.03 (d, J = 5.2 Hz, 3H), 2.78 (s, 3H), 2.66 (s, 3H). | 612 |

-continued

| Example | Structure | NMR | MS (M + H)+ |
|---|---|---|---|
| 8 | 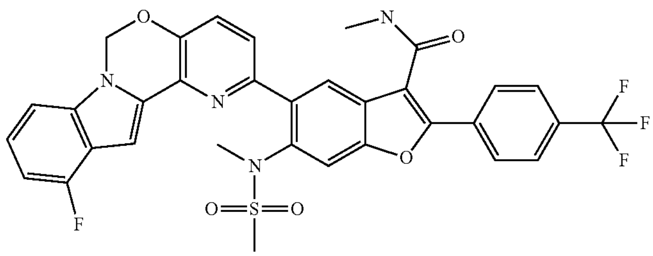 [SMILES: CNC(=O)c1c(-c2ccc(C(F)(F)F)cc2)oc2cc(N(C)S(C)(=O)=O)c(-c3ccc4c(n3)-c3cc5c(F)cccc5n3CO4)cc12] | ¹H-NMR (CDCl₃, 400 MHz) δ 8.08 (d, J = 8.4 Hz, 2H), 7.97 (s, 1H), 7.96 (d, J = 8.4 Hz, 2H), 7.68 (s, 1H), 7.26 (s, 2H), 7.18~7.24 (m, 2H), 7.10 (d, J = 8.4 Hz, 1H), 6.84 (dd, J = 8.0, 10.0 Hz, 2H), 6.13 (br s, 1H), 5.98 (s, 2H), 3.35 (s, 3H), 3.00 (d, J = 4.8 Hz, 3H), 2.75 (s, 3H). | 665 |
| 9 | 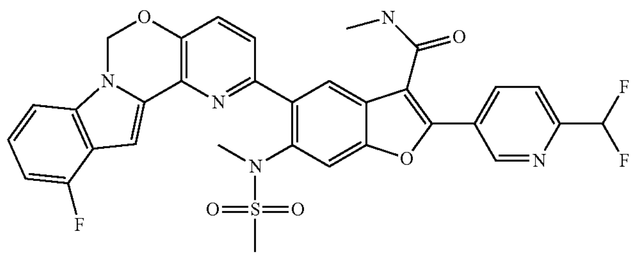 [SMILES: CNC(=O)c1c(-c2ccc(C(F)F)nc2)oc2cc(N(C)S(C)(=O)=O)c(-c3ccc4c(n3)-c3cc5c(F)cccc5n3CO4)cc12] | ¹H-NMR (CDCl₃, 400 MHz) δ 9.24 (s, 1H), 8.54~8.60 (m, 1H), 7.98 (s, 1H), 7.72~7.80 (m, 2H), 7.52 (s, 2H), 7.21~7.26 (m, 2H), 7.13 (d, J = 8.0 Hz, 1H), 6.88 (s, 1H), 6.17~6.71 (m, 1H), 6.17 (d, J = 4.4 Hz, 1H), 6.01 (s, 2H), 3.36 (s, 3H), 3.05 (d, J = 5.2 Hz, 3H), 2.80 (s, 3H). | 648 |
| 10 | 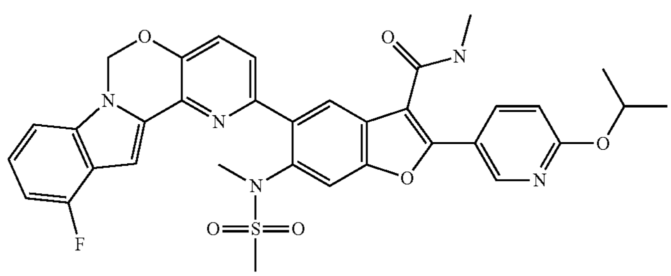 [SMILES: CNC(=O)c1c(-c2ccc(OC(C)C)nc2)oc2cc(N(C)S(C)(=O)=O)c(-c3ccc4c(n3)-c3cc5c(F)cccc5n3CO4)cc12] | ¹H-NMR (CDCl₃, 400 MHz) δ 8.72 (s, 1H), 8.12~8.15 (m, 1H), 7.99 (s, 1H), 7.65 (s, 1H), 7.46~7.50 (m, 2H), 7.17~7.20 (m, 2H), 7.09~7.11 (m, 1H), 6.77~6.85 (m, 2H), 5.99 (s, 2H), 5.92~5.93 (m, 1H), 5.35~5.42 (m, 1H), 3.35 (s, 3H), 2.99 (d, J = 4.8 Hz, 3H), 2.73 (s, 3H), 1.38 (d, J = 6.4 Hz, 6H). | 656 |
| 11 | 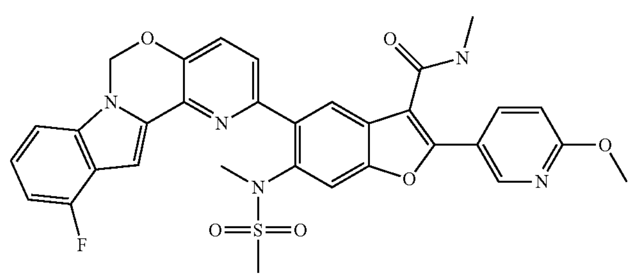 [SMILES: CNC(=O)c1c(-c2ccc(OC)nc2)oc2cc(N(C)S(C)(=O)=O)c(-c3ccc4c(n3)-c3cc5c(F)cccc5n3CO4)cc12] | ¹H-NMR (CDCl₃, 400 MHz) δ 8.76 (s, 1H), 8.75 (q, J = 2.4 Hz, 1H), 7.99 (s, 1H), 7.67 (s, 1H), 7.49 (d, J = 2.4 Hz, 2H), 7.18~7.24 (m, 2H), 7.12 (d, J = 2.4 Hz, 1H), 7.82~7.88 (m, 2H), 5.99 (s, 2H), 5.97 (d, J = 2.4 Hz, 1H), 4.01 (s, 3H), 3.37 (s, 3H), 3.01 (d, J = 3.2 Hz, 3H), 2.75 (s, 3H). | 628 |
| 12 | 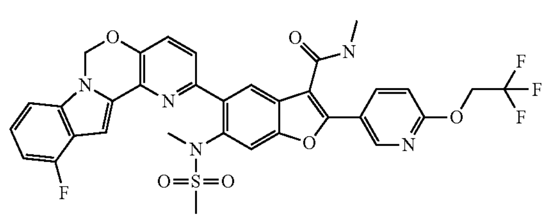 [SMILES: CNC(=O)c1c(-c2ccc(OCC(F)(F)F)nc2)oc2cc(N(C)S(C)(=O)=O)c(-c3ccc4c(n3)-c3cc5c(F)cccc5n3CO4)cc12] | ¹H-NMR (CDCl₃, 400 MHz) δ 8.78 (d, J = 1.6 Hz, 1H), 8.32 (dd, J = 1.6, 8.8 Hz, 1H), 7.97 (s, 1H), 7.69 (s, 1H), 7.49~7.54 (m, 2H), 7.20~7.26 (m, 2H), 7.13 (d, J = 8.0 Hz, 1H), 7.00 (d, J = 8.8 Hz, 1H), 6.86 (dd, J = 8.0, 8.8 Hz, 2H), 6.09 (d, J = 4.4 Hz, 1H), 6.01 (s, 2H), 4.86 (q, J = 8.0 Hz, 2H), 3.37 (s, 3H), 3.03 (d, J = 4.8 Hz, 3H), 2.78 (s, 3H). | 696 |

-continued
| Example | Structure | NMR | MS (M + H)+ |
|---|---|---|---|
| 13 | 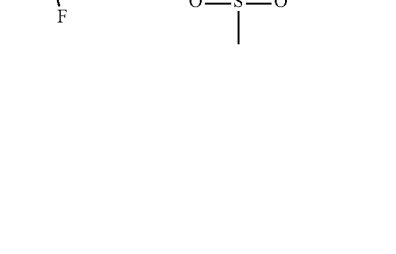 | ¹H-NMR (CDCl₃, 400 MHz) δ 9.13 (s, 1H), 7.89 (s, 1H), 7.64 (s, 1H), 7.45 (d, J = 0.6 Hz, 2H), 7.16~7.13 (m, 2H), 7.06 (d, J = 8.4 Hz, 1H), 5.98 (s, 1H), 5.94 (s, 2H), 4.05 (s, 3H), 3.28 (s, 3H), 2.99 (d, J = 4.8 Hz, 3H), 2.73 (s, 3H). | 629 |
| 14 | 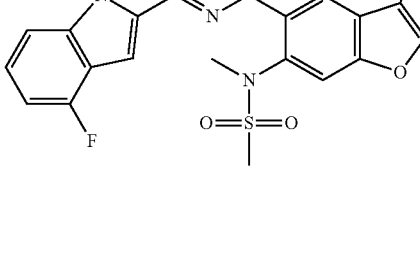 | ¹H-NMR (DMSO-d₆, 400 MHz) δ 8.49 (s, 1H), 8.28 (d, J = 4.8 Hz, 1H), 8.07 (s, 1H), 7.93 (s, 1H), 7.84 (s, 1H), 7.69 (d, J = 8.4 Hz, 1H), 7.60 (d, J = 8.8 Hz, 1H), 7.49 (d, J = 8.0 Hz, 1H), 7.21~7.27 (m, 1H), 7.09 (s, 1H), 6.91 (t, J = 8.8 Hz, 1H) 6.25 (s, 2H), 4.23 (dd, J = 14.4 Hz, 7.6 Hz, 2H), 3.28 (s, 3H), 2.92 (s, 3H), 2.82 (d, J = 4.8 Hz, 3H), 1.40 (t, J = 7.2 Hz, 3H). | 615 |
| 15 | 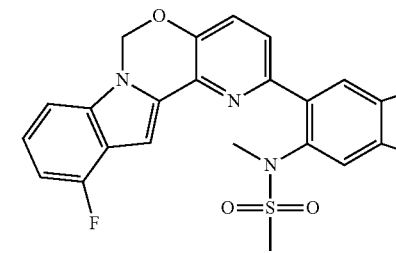 | ¹H-NMR (CDCl₃, 400 MHz) δ 8.34 (d, J = 5.2 Hz,1H), 8.13 (s,1H), 7.99 (d, J = 9.6 Hz, 1H), 7.67 (s, 1H), 7.50 (d, J = 3.2 Hz, 2H), 7.23 (s, 2H), 7.12~7.08 (m, 2H), 6.87 (t, J = 10.0 Hz, 9.2 Hz, 1H), 6.00 (d, 2H), 5.87.(d, J = 5.2 Hz, 1H), 4.05 (s, 3H), 3.39 (s, 3H), 2.94 (d, J = 4.8 Hz, 3H), 2.71 (s, 1H). | 628 |
| 16 | 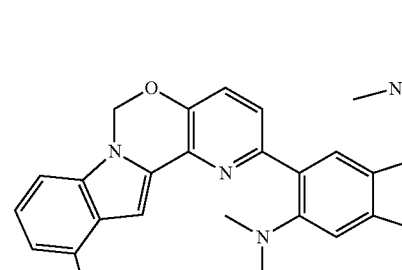 | ¹H-NMR (CDCl₃, 400 MHz) δ 8.31 (s, 1H), 7.71 (s, 1H), 7.51 (s, 2H), 7.20~7.23 (m, 2H), 7.13 (d, J = 8.4 Hz, 1H), 6.86 (t, J = 8.8 Hz, 1H), 6.56 (s, 1H), 6.02 (s, 2H), 5.95 (br s, 1H), 3.98 (s, 3H), 3.41 (s, 3H), 2.96 (d, J = 4.8 Hz, 3H), 2.71 (s, 3H), 2.37 (s, 3H). | 615 |

Example 17

5-(11-fluoro-6H-pyrido[2',3':5,6][1,3]oxazino[3,4-a]indol-2-yl)-2-(2-hydroxypyridin-3-yl)-N-methyl-6-(N-methylmethylsulfonamido)benzofuran-3-carboxamide

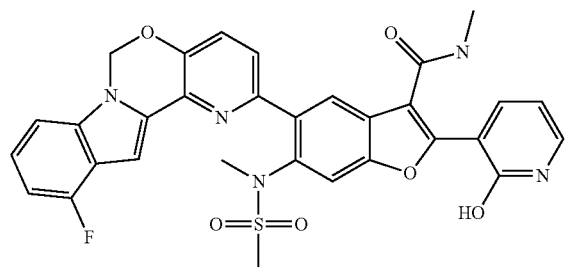 [SMILES: CNC(=O)c1c(-c2cccnc2O)oc2cc(N(C)S(C)(=O)=O)c(-c3ccc4c(n3)-c3cc5c(F)cccc5n3CO4)cc12]

Step 1 - Synthesis of 5-(11-fluoro-6H-pyrido[2',3':4,5][1,3]oxazino[3,4-a]indol-2-yl)-2-(2-hydroxypyridin-3-yl)-N-methyl-6-(N-methylmethylsulfonamido)benzofuran-3-carboxamide

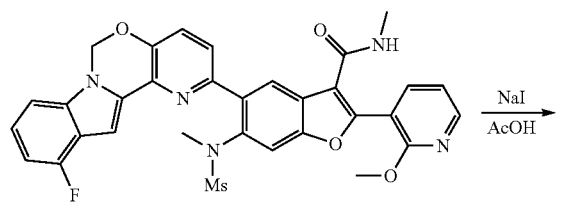

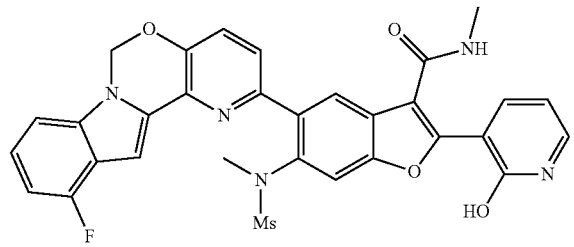

A mixture of 5-(11-fluoro-6H-pyrido[2',3':5,6][1,3]oxazino[3,4-a]indol-2-yl)-2-(2-methoxypyridin-3-yl)-N-methyl-6-(N-methylmethylsulfonamido)benzofuran-3-carboxamide (45 mg, 0.07 mmol) and NaI (54 mg, 0.36 mmol) in HOAc (1 mL) was stirred at 100° C. under $N_2$ for 5 h. After the reaction, it was extracted with EtOAc (10 mL×3) and $Na_2CO_3$ (a.q., 5 mL). The organic layer was washed with brine (5 mL×3), dried over aq. $Na_2SO_4$ and concentrated. The residue was purified by prep-HPLC to give 5-(11-fluoro-6H-pyrido[2',3':5,6][1,3]oxazino[3,4-a]indol-2-yl)-2-(2-hydroxypyridin-3-yl)-N-methyl-6-(N-methylmethylsulfonamido)benzofuran-3-carboxamide (10 mg, yield: 23%). $^1$H-NMR (CDCl$_3$, 400 MHz) δ 8.20 (s, 1H), 8.11 (s, 1H), 7.97 (d, J=5.2 Hz, 1H), 7.96 (s, 1H), 7.66 (d, J=1.2 Hz, 1H), 7.55 (m, 2H), 7.23 (s, 2H), 7.14 (d, J=8.4 Hz, 1H), 6.85 (s, 1H), 6.60 (t, J=6.8 Hz, 1H), 6.01 (s, 2H), 5.30 (s, 1H), 3.41 (s, 3H), 2.96 (d, J=4.8 Hz, 3H), 2.70 (s, 3H). MS (M+H)$^+$: 614.

Example 18

5-(11-fluoro-6H-pyrido[2',3':5,6][1,3]oxazino[3,4-a]indol-2-yl)-2-(2-methoxypyridin-3-yl)-N-methyl-6-(N-methylmethylsulfonamido)benzofuran-3-carboxamide

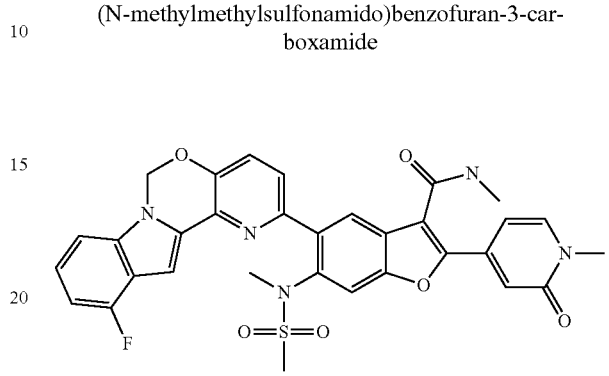

Step 1 - Synthesis of 5-(11-fluoro-6H-pyrido[2',3':4,5][1,3]oxazino[3,4-a]indol-2-yl)-N-methyl-6-(N-methylmethylsulfonamido)-2-(2-oxo-1,2-dihydropyridin-4-yl)benzofuran-3-carboxamide

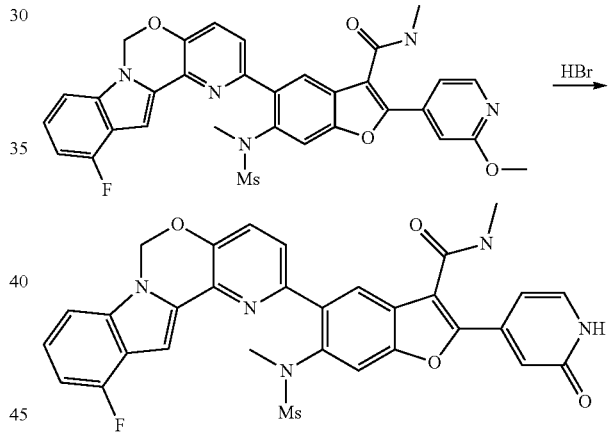

To a solution of 5-(11-fluoro-6H-pyrido[2',3':5,6][1,3]oxazino[3,4-a]indol-2-yl)-2-(2-methoxypyridin-4-yl)-N-methyl-6-(N-methylmethylsulfonamido)benzofuran-3-carboxamide (30 mg, 0.05 mmol) in HOAc (1 mL) was added HBr—HOAc (1 mL) at 0° C. Then the mixture was stirred at 80° C. for 2 hours. The solvent was removed by vacuum and NaHCO$_3$ (a.q.) was added. The mixture was extracted with DCM, and the organic phase was dried over Na$_2$SO$_4$. After concentrated in vacuo, the residue was purified by prep-HPLC to give the product of 5-(11-fluoro-6H-pyrido[2',3':5,6][1,3]oxazino[3,4-a]indol-2-yl)-N-methyl-6-(N-methylmethylsulfonamido)-2-(2-oxo-1,2-dihydropyridin-4-yl)benzofuran-3-carboxamide (15 mg, yield: 52%). $^1$H-NMR (DMSO-d$_6$, 400 MHz) δ 8.73~8.75 (m, 1H), 8.11 (s, 1H), 7.85 (s, 1H), 7.73 (q, J=8.8 Hz, 1H), 7.59~7.62 (m, 2H), 7.51~7.61 (m, 2H), 7.25~7.27 (m, 1H), 7.11 (s, 1H), 6.88~6.96 (m, 1H), 6.65 (d, J=2.8 Hz, 1H), 6.27 (s, 2H), 3.31 (s, 3H), 2.97 (s, 3H), 2.85 (d, J=4.0 Hz, 3H). MS (M+H)$^+$: 614.

Step 2 - Synthesis of 5-(11-fluoro-6H-pyrido[2',3':4,5][1,3]oxazino[3,4-a]indol-2-yl)-2-(2-methoxypyridin-3-yl)-N-methyl-6-(N-methylmethylsulfonamido)benzofuran-3-carboxamide

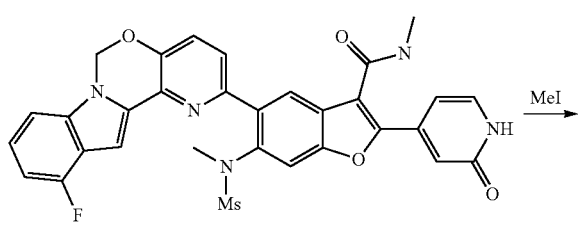

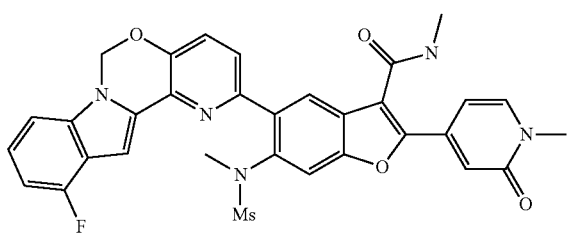

To a suspension of 5-(11-fluoro-6H-pyrido[2',3':5,6][1,3]oxazino[3,4-a]indol-2-yl)-N-methyl-6-(N-methylmethylsulfonamido)-2-(2-oxo-1,2-dihydropyridin-4-yl)benzofuran-3-carboxamide (20 mg, 0.03 mmol) and K₂CO₃ (10 mg, 0.06 mmol) in DMF (1 mL) was added CH₃I (5 mg, 0.03 mol) at 0° C. under N₂, and then the mixture was stirred for 12 hours at room temperature. After being concentrated in vacuo, the resulting residue was suspended in H₂O and extracted with DCM. The combined organic layer was washed with H₂O and dried over Na₂SO₄. After concentration, the residue was purified by prep-HPLC to give the product of 5-(11-fluoro-6H-pyrido[2',3':5,6][1,3]oxazino[3,4-a]indol-2-yl)-N-methyl-2-(1-methyl-2-oxo-1,2-dihydropyridin-4-yl)-6-(N-methylmethylsulfonamido)benzofuran-3-carboxamide (10 mg, yield: 49%). ¹H-NMR (DMSO-d₆, 400 MHz) δ 8.7~28.74 (m, 1H), 8.10 (s, 1H), 7.84~7.86 (m, 2H), 7.70~7.72 (m, 1H), 7.59~7.62 (m, 1H), 7.50~7.53 (m, 1H), 7.24~7.28 (m, 1H), 7.23 (s, 1H), 6.96~7.09 (m, 2H), 6.67~6.91 (m, 1H), 6.27 (s, 2H), 3.48 (s, 3H), 3.31 (s, 3H), 2.97 (s, 3H), 2.85 (d, J=4.4 Hz, 3H). MS (M+H)⁺: 628.

Examples 19 and 20

19

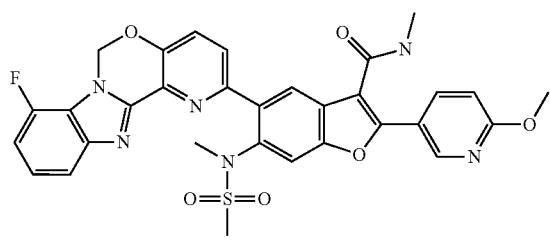 [SMILES: CNC(=O)c1c(-c2ccc(OC)nc2)oc2cc(N(C)S(C)(=O)=O)c(-c3ccc4c(n3)-c3cc5c(F)cccc5n3C(CO)O4)cc12]

20

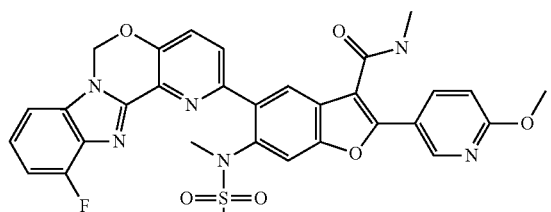

Step 1 - Synthesis of methyl 3-hydroxypicolinate

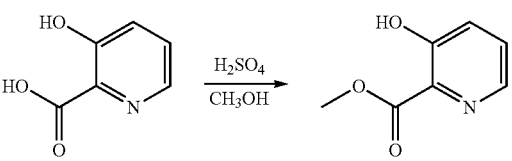

A solution of 3-hydroxypicolinic acid (30 g, 0.22 mol) in CH₃OH (300 mL) was stirred at RT and conc. H₂SO₄ (30 mL) was added dropwise. The resulting mixture was stirred at 80° C. overnight. After the pH was adjusted to 7 with solid Na₂CO₃, the mixture was filtrated and the precipitate was thoroughly washed with EtOAc several times. The filtrate was concentrated to give crude methyl 3-hydroxypicolinate (27 g, yield: 82.8%). ¹H-NMR (CDCl₃, 400 MHz) δ 10.57 (s, 1H), 8.22~8.20 (m, 1H), 7.32~7.29 (m, 1H), 3.93 (s, 3H). MS (M+H)⁺: 154.

Step 2 - Synthesis of methyl 6-bromo-3-hydroxypicolinate

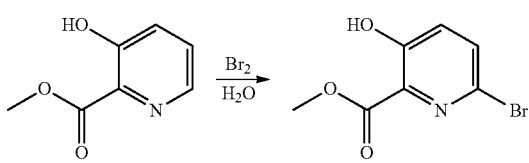

A solution of methyl 3-hydroxypicolinate (5 g, 32.65 mmol) in 60 mL of H₂O was stirred at RT and Br₂ (5.22 g, 32.65 mmol) was added dropwise. The mixture was stirred at RT overnight, and the resulting solid was collected and washed with water to afford methyl 6-bromo-3-hydroxypicolinate. Then the filtrate was basified with Na₂CO₃ until pH reached 7, and after extracted with EtOAc, the organic layer was concentrated to give the 2ⁿᵈ part of methyl 6-bromo-3-hydroxypicolinate (6.1 g total, yield: 80.7%). ¹H-NMR (CDCl₃, 400 MHz) δ 10.67 (s, 1H), 7.54 (t, J=8.0 Hz, 1H), 7.24 (d, J=4.0 Hz, 1H), 4.02 (s, 3H). MS (M+H)⁺: 232/234.

Step 3 - Synthesis of methyl 6-bromo-3-methoxypicolinate

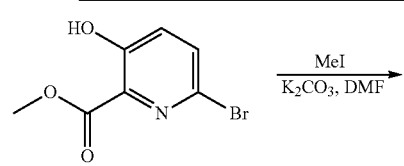

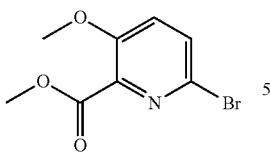

A mixture of methyl 6-bromo-3-hydroxypicolinate (4 g, 17.2 mmol), CH₃I (7.15 g, 34.5 mmol) and K₂CO₃ (4.76 g, 34.5 mmol) in DMF (50 mL) was stirred at RT for 3 hours. After concentrated, the mixture was diluted with H₂O and extracted with EtOAc (50 mL*3). The organic layer was dried over Na₂SO₄ and concentrated to give crude methyl 6-bromo-3-methoxypicolinate (4 g, yield: 90%). ¹H-NMR (CDCl₃, 400 MHz) δ 7.56 (d, J=8.0 Hz, 1H), 7.25 (d, J=8.0 Hz, 1H), 3.94 (s, 3H), 3.90 (s, 3H). MS (M+H)⁺: 256/258.

Step 4 - Synthesis of 6-bromo-3-methoxypicolinic acid

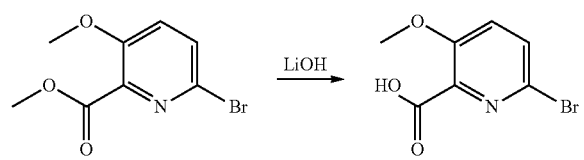

A mixture of methyl 6-bromo-3-methoxypicolinate (4 g, 18.4 mmol) and LiOH—H₂O (1.6 g, 36.9 mmol) in dioxane/H₂O (5/1, 40 mL) was stirred at RT overnight. After pH was adjusted to 7, the mixture was filtered to provide crude 6-bromo-3-methoxypicolinic acid (3.1 g, yield: 81%). ¹H-NMR (CDCl₃, 400 MHz) δ 10.71 (m, 1H), 7.70 (d, J=8.0 Hz, 1H), 7.40 (d, J=8.0 Hz, 1H), 4.01 (s, 3H). MS (M+H)⁺: 232/234.

Step 5 - Synthesis of 2-(6-bromo-3-methoxypyridin-2-yl)-4-fluoro-1H-benzo[d]imidazole and 6-bromo-2-(4-fluoro-1H-benzo[d]imidazol-2-yl)pyridin-3-ol

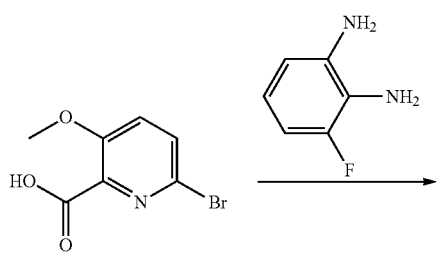

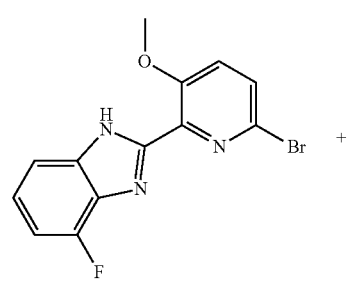

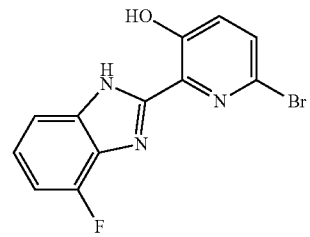

A mixture of 6-bromo-3-methoxypicolinic acid (1.84 g, 7.93 mmol) and 3-fluorobenzene-1,2-diamine (1.0 g, 7.93 mmol) was stirred in PPA (3 mL) on a pre-heated oil-bath at 120° C. for 14 h. The mixture was poured to ice-water and basified to pH=8 with Na₂CO₃. Then the mixture was filtrated to collect the brown solid as 6-bromo-2-(4-fluoro-1H-benzo[d]imidazol-2-yl)pyridin-3-ol (900 mg, yield: 37%). The filtrated was extracted with ethyl acetate, and the organic layer was washed with brine and dried over Na₂SO₄. After concentrated, the residue was purified by column chromatography to give the product of 2-(6-bromo-3-methoxypyridin-2-yl)-4-fluoro-1H-benzo[d]imidazole (350 mg, yield: 14%). ¹H-NMR (CDCl₃, 400 MHz) δ 10.43~10.56 (m, 1H), 7.46 (d, J=8.8 Hz, 1H), 7.33 (d, J=8.8 Hz, 1H), 7.21~7.30 (m, 2H), 6.90~6.98 (m, 1H), 4.05 (s, 3H). MS (M+H)⁺: 322/324.

Step 6 - Synthesis of 6-bromo-2-(4-fluoro-1H-benzo[d]imidazol-2-yl)pyridin-3-ol

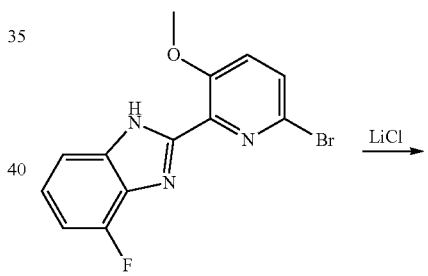

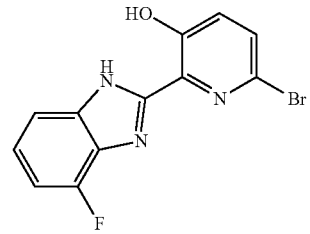

To a solution of 2-(6-bromo-3-methoxypyridin-2-yl)-4-fluoro-1H-benzo[d]imidazole (350 mg, 1.12 mmol) in DMF (10 mL) was added LiCl (650 mg, 15.5 mmol) under N₂ protection. The mixture was stirred on a pre-heated oil-bath at 100° C. overnight. After extracted with EtOAc, the organic phase was dried over Na₂SO₄ and concentrated. The residue was purified by prep-TLC (PE:EA=5:1) to give the product of 6-bromo-2-(4-fluoro-1H-benzo[d]imidazol-2-yl)pyridin-3-ol (200 mg, yield: 60%). ¹H-NMR (DMSO-d₆, 400 MHz) δ 13.75 (s, 1H), 12.70 (s, 1H), 7.64 (d, J=8.4 Hz, 1H), 7.50 (d, J=8.4 Hz, 1H), 7.41 (s, 1H), 7.30 (s, 1H), 7.12 (s, 1H). MS (M+H)⁺: 308/310.

Step 7 - Synthesis of 2-bromo-11-fluoro-6H-benzo[4,5]imidazo[1,2-c]pyrido[2,3-e][1,3]oxazine and 2-bromo-8-fluoro-6H-benzo[4,5]imidazo[1,2-c]pyrido[2,3-e][1,3]oxazine

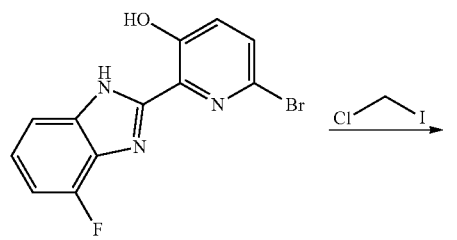

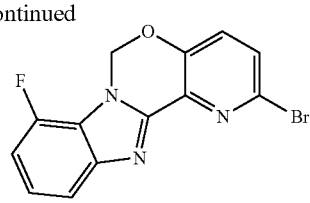

To a mixture of compound 7 (540 mg, 1.75 mmol) and Cs$_2$CO$_3$ (1.15 g, 3.50 mmol) in DMF (27 mL) was added chloroiodomethane (0.14 mL) in DMF (5.4 mL) under N$_2$ protection. The mixture was stirred at 90° C. overnight, and after concentrated, the mixture was diluted with water and extract with EtOAc. The organic layer was dried over Na$_2$SO$_4$ and concentrated, the resulting yellow solid was obtained as a mixture of 2-bromo-11-fluoro-6H-benzo[4,5]imidazo[1,2-c]pyrido[2,3-e][1,3]oxazine and 2-bromo-8-fluoro-6H-benzo[4,5]imidazo[1,2-c]pyrido[2,3-e][1,3]oxazine (360 mg total, ~1:1, yield: ~35% each), which couldn't be separated with column and was used for the next step without further purification. A sample of pure 2-bromo-8-fluoro-6H-benzo[4,5]imidazo[1,2-c]pyrido[2,3-e][1,3]oxazine was obtained by prep-TLC and identified with 2D NMR. $^1$H-NMR (DMSO-d$_6$, 400 MHz) δ 7.73 (d, J=8.8 Hz, 1H), 7.50 (d, J=8.8 Hz, 1H), 7.53 (d, J=8.0 Hz, 1H), 7.31~7.36 (m, 1H), 7.10~7.15 (m, 1H), 6.37 (s, 2H). MS (M+H)$^+$: 320/322.

Step 8 - Synthesis of 5-(8-fluoro-6H-benzo[4,5]imidazo[1,2-c]pyrido[2,3-e][1,3]oxazin-2-yl)-2-(6-methoxypyridin-3-yl)-N-methyl-6-(N-methylmethylsulfonamido)benzofuran-3-carboxamide (Example 19) and 5-(11-fluoro-6H-benzo[4,5]imidazo[1,2-c]pyrido[2,3-e][1,3]oxazin-2-yl)-2-(6-methoxypyridin-3-yl)-N-methyl-6-(N-methylmethylsulfonamido)benzofuran-3-carboxamide (Example 20)

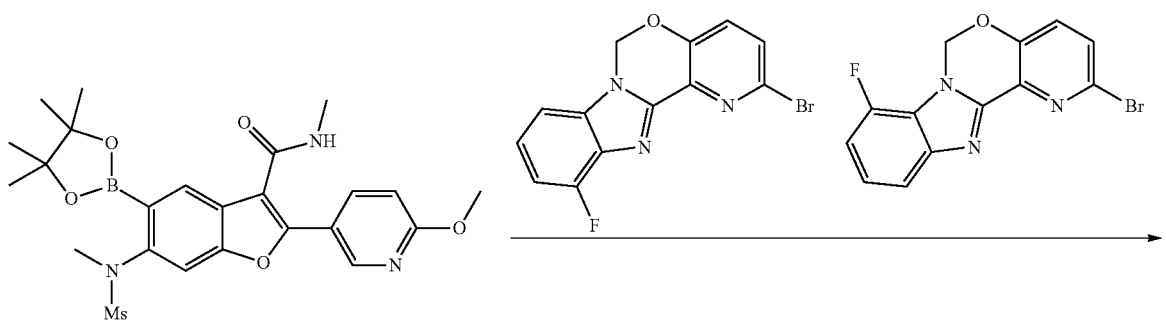

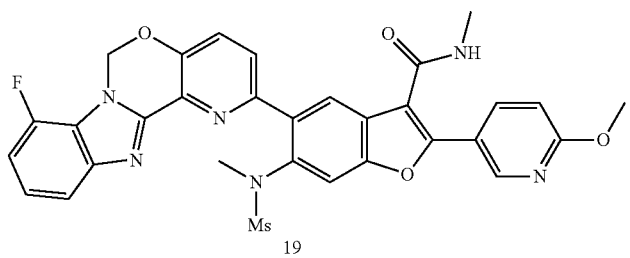

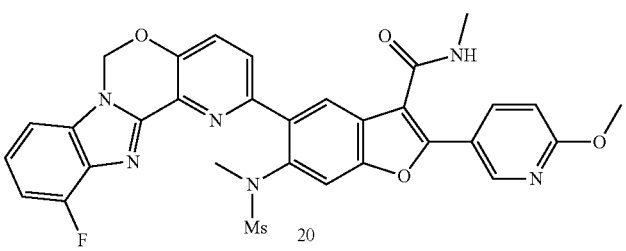

To a stirring mixture of 2-(6-methoxypyridin-3-yl)-N-methyl-6-(N-methylmethylsulfonamido)-5-(4,4,5,5-tetramethyl-1,3,2-dioxaborolan-2-yl)benzofuran-3-carboxamide (160 mg, 0.32 mmol), 2-bromo-11-fluoro-6H-benzo[4,5]imidazo[1,2-c]pyrido[2,3-e][1,3]oxazine and 2-bromo-8-fluoro-6H-benzo[4,5]imidazo[1,2-c]pyrido[2,3-e][1,3]oxazine (100 mg, ~1:1 mixture, 0.32 mmol total) and K$_2$CO$_3$ (86 mg, 0.64 mmol) in dioxane/H$_2$O (2.0 mL/0.2 mL) was added Pd(dppf)Cl$_2$ (32 mg) under N$_2$ protection. The mixture was stirred at 90° C. for 10 h. The mixture was concentrated and the residue was extract with EtOAc. The residue was washed with H$_2$O, brine, dried over Na$_2$SO$_4$. After being concentrated, the crude product was purified by prep-HPLC to give two individual regio-isomers.

5-(8-fluoro-6H-benzo[4,5]imidazo[1,2-c]pyrido[2,3-e][1,3]oxazin-2-yl)-2-(6-methoxypyridin-3-yl)-N-methyl-6-(N-methylmethylsulfonamido)benzofuran-3-carboxamide (80 mg, yield: 70%, based on the content of corresponding bromide). $^1$H-NMR (CDCl$_3$, 400 MHz) δ 8.76 (d, J=2.4 Hz, 1H), 8.22 (d, J=8.8 Hz, 1H), 8.03 (s, 1H), 7.77 (d, J=4.8 Hz, 1H), 7.56~7.63 (m, 3H), 7.20~7.23 (m, 1H), 7.03~7.07 (m, 1H), 6.82 (d, J=8.4 Hz, 1H), 6.41 (s, 1H), 6.30 (s, 2H), 4.00 (s, 3H), 3.20 (s, 3H), 3.02 (d, J=5.2 Hz, 3H), 2.97 (s, 3H). MS (M+H)$^+$: 629.

5-(11-fluoro-6H-benzo[4,5]imidazo[1,2-c]pyrido[2,3-e][1,3]oxazin-2-yl)-2-(6-methoxypyridin-3-yl)-N-methyl-6-(N-methylmethylsulfonamido)benzofuran-3-carboxamide (70 mg, yield: 65%, based on the content of corresponding bromide). $^1$H-NMR (CDCl$_3$, 400 MHz) δ 8.70 (d, J=2.4 Hz, 1H), 8.16~8.19 (m, 1H), 7.99 (s, 1H), 7.73 (d, J=8.4 Hz, 1H), 7.50 (d, J=8.8 Hz, 2H), 7.23~7.26 (m, 1H), 7.10 (d, J=8.0 Hz, 1H), 6.93~6.97 (m, 1H), 6.77 (d, J=8.8 Hz, 1H), 6.59 (s, 1H), 6.08 (s, 2H), 3.94 (s, 3H), 3.14 (s, 3H), 2.99 (d, J=4.8 Hz, 3H), 2.95 (s, 3H). MS (M+H)$^+$: 629.

Example 21

(S or R)-5-(11-fluoro-6-(hydroxymethyl)-6H-pyrido[2',3':5,6][1,3]oxazino[3,4-a]indol-2-yl)-2-(6-methoxypyridin-3-yl)-N-methyl-6-(N-methylmethylsulfonamido)benzofuran-3-carboxamide

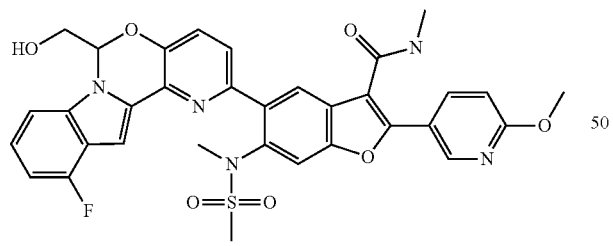

Step 1 - Synthesis of 6-chloro-2-(4-fluoroindolin-2-yl)pyridin-3-ol

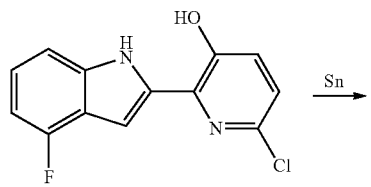

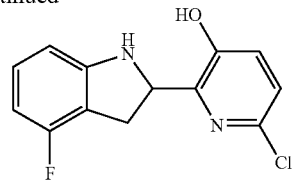

A mixture of 6-chloro-2-(4-fluoro-1H-indol-2-yl)pyridin-3-ol (10 g, 38 mmol) and metal Sn (23 g, 190 mmol) in CH$_3$CH$_2$OH/concentrated HCl (60 mL/40 mL) was stirred under reflux for 3 h. The mixture was cooled to room temperature and adjusted to pH=7 by saturated NaOH and filtered though a Celite pad. The filtrate was extracted with EtOAc, washed by brine, dried over Na$_2$SO$_4$ and concentrated. The residue was purified by silica gel chromatography (PE:EtOAc=10:1) to get 6-chloro-2-(4-fluoroindolin-2-yl)pyridin-3-ol (8 g, yield: 80%). $^1$H-NMR (CDCl$_3$, 400 MHz) δ 9.86 (s, 1H), 7.10~7.20 (m, 3H), 6.33~6.91 (m, 2H), 5.15~5.21 (m, 1H), 4.61 (s, 1H), 3.65~3.71 (m, 1H), 3.04~3.11 (m, 1H). MS (M+H)$^+$: 265.

Step 2 - Synthesis of ethyl 2-chloro-11-fluoro-12,12a-dihydro-6H-pyrido[2',3':5,6][1,3]oxazine[3,4-a]indole-6-carboxylate

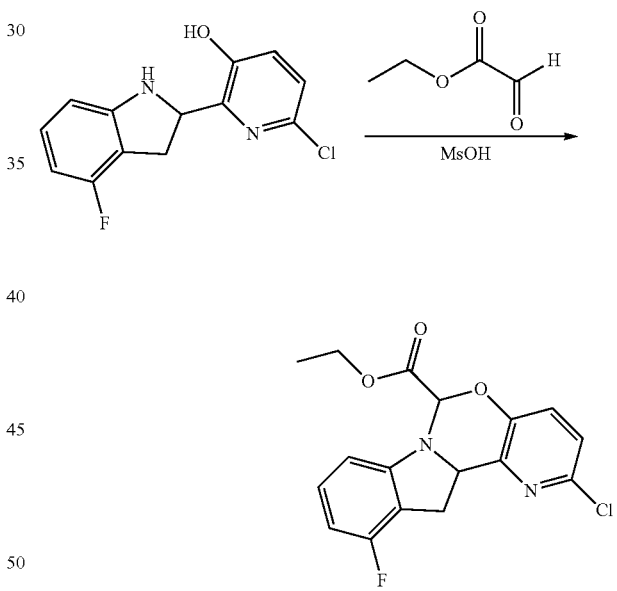

To a solution of 6-chloro-2-(4-fluoroindolin-2-yl)pyridin-3-ol (8.53 g, 32.31 mmol) and glyoxylic acid ethyl ester (6.59 g, 64.59 mmol) in THF (80 mL), MsOH (0.31 g, 3.23 mmol) was added. The mixture was stirred at 50° C. for 2 hours. The mixture was diluted with water and extracted with EtOAc. The organic layer was washed with brine (30 mL), dried over Na$_2$SO$_4$ and concentrated. The residue was purified by column chromatography (PE: EtOAc=10:1) to afford ethyl 2-chloro-11-fluoro-12,12a-dihydro-6H-pyrido[2',3':5,6][1,3]oxazino[3,4-a]indole-6-carboxylate (10.2 g, yield: 90.3%). $^1$H-NMR (CDCl$_3$, 400 MHz) δ 7.04~7.13 (m, 3H), 6.63 (d, J=8.0 Hz, 1H), 6.55 (t, J=8.4 Hz, 1H), 6.03 (s, 1H), 5.09 (d, J=8.8 Hz, 1H), 4.22~4.34 (m, 2H), 3.73 (d, J=16.4 Hz, 1H), 3.44~3.51 (m, 1H), 1.29 (d, J=7.2 Hz, 3H). MS (M+H)$^+$: 349.

Step 3 - Synthesis of ethyl 2-chloro-11-fluoro-6H-pyrido[2',3':5,6][1,3]oxazine[3,4-a]indole-6-carboxylate

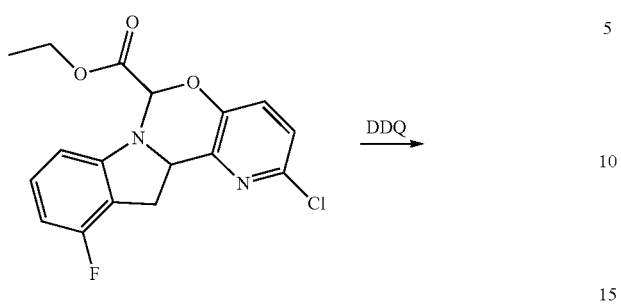

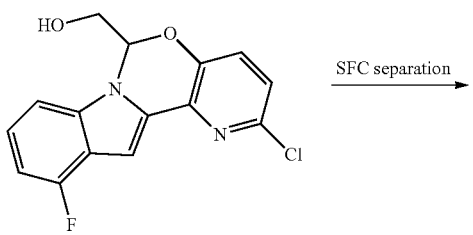

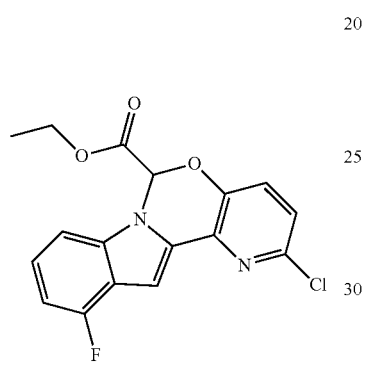

To a solution of ethyl 2-chloro-11-fluoro-12,12a-dihydro-6H-pyrido[2',3':5,6][1,3]oxazino[3,4-a]indole-6-carboxylate (10.22 g, 29.36 mmol) and DDQ (8.67 g, 38.17 mmol) in toluene (80 mL) was stirred at 80° C. for 2 hours. The mixture was then diluted with water (50 mL) and extracted with EtOAc (30 mL*3). The organic layer was washed with brine (30 mL), dried over Na₂SO₄ and concentrated. The residue was purified by column chromatography (PE:EtOAc=20:1) to afford ethyl 2-chloro-11-fluoro-6H-pyrido[2',3':5,6][1,3]oxazino[3,4-a]indole-6-carboxylate (8.64 g, yield: 85%), which was also prepared from 6-chloro-2-(4-fluoro-1H-indol-2-yl)pyridin-3-ol and methyl 2,2-dibromoacetate in the presence of base, such as DBU etc. ¹H-NMR (CDCl₃, 400 MHz) δ 7.33 (d, J=8.4 Hz, 1H), 7.30 (s, 1H), 7.09~7.18 (m, 3H), 6.78~6.83 (m, 1H), 6.52 (s, 1H), 3.96~4.09 (m, 2H), 1.02 (t, J=7.2 Hz, 3H). MS (M+H)⁺: 347.

Step 4 - Synthesis of (2-chloro-11-fluoro-6H-pyrido[2',3':5,6][1,3]oxazino[3,4-a]indol-6-yl)methanol

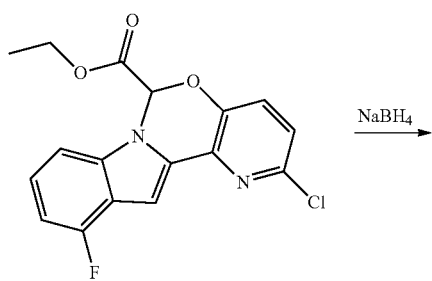

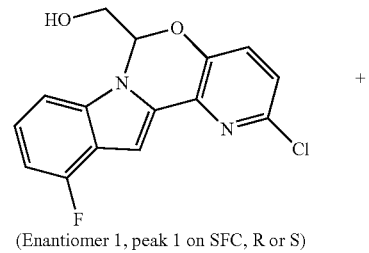

To a solution of ethyl 2-chloro-11-fluoro-6H-pyrido[2',3':5,6][1,3]oxazino[3,4-a]indole-6-carboxylate (3 g, 8.73 mmol) and NaBH₄ (1.58 g, 43.67 mmol) in CH₃OH/DCM (30 mL/10 mL) was stirred at room temperature for 2 hours. The mixture was poured to H₂O and extracted with ethyl acetate. The organic layer was washed with brine, dried over Na₂SO₄ and concentrated in vacuum to give (2-chloro-11-fluoro-6H-pyrido[2',3':5,6][1,3]oxazino[3,4-a]indol-6-yl)methanol (2.54 g, yield: 95.5%).

The product was purified by SFC to give two single enantiomers.

(R or S)-(2-chloro-11-fluoro-6H-pyrido[2',3':5,6][1,3]oxazino[3,4-a]indol-6-yl)methanol (enantiomer 1, peak 1 on SFC, AD-3_5_5_40_2,4ML, HPLC_RT=1.522 min).

(S or R)-(2-chloro-11-fluoro-6H-pyrido[2',3':5,6][1,3]oxazino[3,4-a]indol-6-yl)methanol (enantiomer 1, peak 2 on SFC, AD-3_5_5_40_2,4ML, HPLC_RT=1.731 min).

Step 5 - Synthesis of (S or R)-5-(11-fluoro-6-(hydroxymethyl)-6H-pyrido[2',3':5,6][1,3]oxazino[3,4-a]indol-2-yl)-2-(6-methoxypyridin-3-yl)-N-methyl-6-(N-methylmethylsulfonamido)benzofuran-3-carboxamide

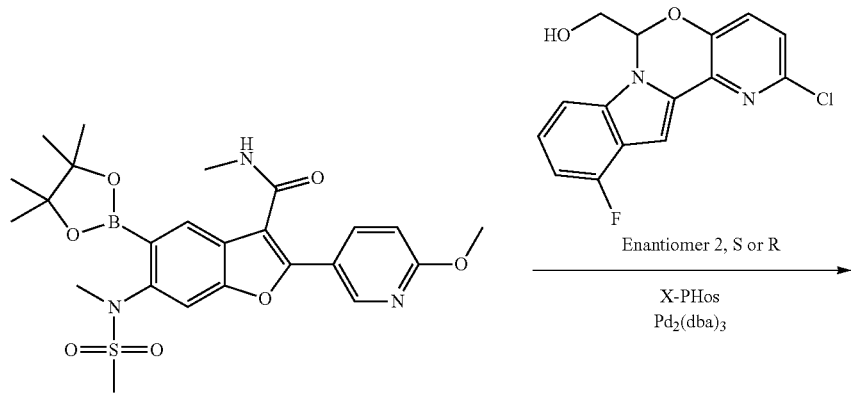

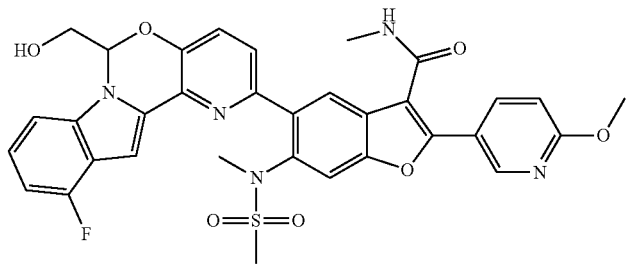

To a solution of (S or R)-(2-chloro-11-fluoro-6H-pyrido[2',3':5,6][1,3]oxazino[3,4-a]indol-6-yl)methanol (35 mg, 0.115 mmol), 2-(6-methoxypyridin-3-yl)-N-methyl-6-(N-methylmethylsulfonamido)-5-(4,4,5,5-tetramethyl-1,3,2-dioxaborolan-2-yl)benzofuran-3-carboxamide (50 mg, 0.097 mmol) and sodium carbonate (20 mg, 0.188 mmol) in 2 mL of 1,4-dioxane and 0.2 mL of water was added $Pd_2(dba)_3$ (10 mg) and X-Phos (10 mg) under nitrogen. The reaction mixture was heated at 70° C. for 16 hours and concentrated in vacuo to remove 1,4-dioxane. And then the residue was suspended in water and extracted with EtOAc. The combined organic phase was washed with brine, dried over $Na_2SO_4$ and concentrated. The residue was purified by prep-HPLC to give the product of (S or R)-5-(11-fluoro-6-(hydroxymethyl)-6H-pyrido[2',3':5,6][1,3]oxazino[3,4-a]indol-2-yl)-2-(6-methoxypyridin-3-yl)-N-methyl-6-(N-methylmethylsulfonamido)benzofuran-3-carboxamide (30 mg, yield: 47%). $^1$H-NMR (CDCl$_3$, 400 MHz) δ 8.72 (d, J=2.4 Hz, 1H), 8.14~8.17 (m, 1H), 7.99 (s, 1H), 7.64 (s, 1H), 7.43~7.48 (m, 2H), 7.14~7.23 (m, 3H), 6.81~6.86 (m, 2H), 6.42~6.45 (m, 1H), 6.06 (brs, 1H), 4.01 (s, 3H), 3.98~4.00 (m, 1H), 3.85~3.88 (m, 1H), 3.37 (s, 3H), 2.96 (d, J=4.8 Hz, 3H), 2.72 (s, 3H), 2.27 (s, 1H). MS (M+H)$^+$: 658.

Examples 22-24

Examples 22-24, depicted in the table below, were prepared in accordance with the method described in Example 21.

| Examples | Structure | NMR | MS (M + H)$^+$ |
|---|---|---|---|
| 22 | S or R | $^1$H-NMR (CDCl$_3$, 400 MHz) δ 9.23 (s, 1H), 8.56 (d, J = 8.0 Hz, 1H), 7.99 (s, 1H), 7.76 (d, J = 8.0 Hz, 1H), 7.72 (s, 1H), 7.45~7.56 (m, 2H), 7.20~7.25 (m, 2H), 7.13~7.20 (m, 1H), 6.88 (s, 1H), 6.85 (d, J = 9.6 Hz, 1H), 6.43~6.70 (m, 1H), 6.10 (d, J = 4.4 Hz, 1H), 4.03 (td, J = 5.6, 12 Hz, 1H), 3.87~3.95 (m, 1H), 3.37 (s, 3H), 3.04 (d, J = 5.2 Hz, 3H), 2.77 (s, 3H). | 678 |

| Examples | Structure | NMR | MS (M + H)+ |
|---|---|---|---|
| 23 | 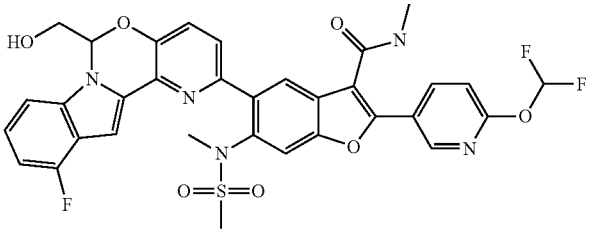 S or R | ¹H-NMR (CDCl₃, 400 MHz) δ 8.77 (s, 1H), 8.37 (d, J = 8.8 Hz, 1H), 7.91 (s, 1H), 7.67 (s, 0.25H), 7.63 (s, 1H), 7.49 (s, 0.5H), 7.44 (s, 2H), 7.31 (s, 0.25H), 7.09~7.15 (m, 2H), 6.96 (d, J = 9.2 Hz, 1H), 6.79 (t, J = 8.4 Hz, 1H), 6.40 (t, J = 4.8 Hz, 1H), 5.95 (s, 1H), 3.91~4.00 (m, 1H), 3.81~3.87 (m, 1H), 3.31 (s, 3H), 2.98 (d, J = 4.4 Hz, 3H), 2.70 (s, 3H), 1.82~1.86 (m, 1H). | 694 |
| 24 | 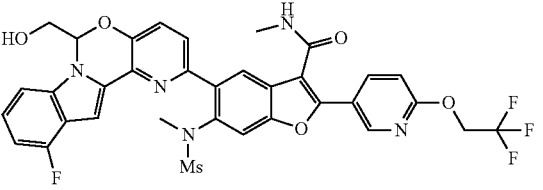 S or R | ¹H-NMR (CDCl₃, 400 MHz) δ 8.81 (s, 1H), 8.32~8.38 (m, 1H), 8.06 (s, 1H), 7.73 (s, 1H), 7.50~7.55 (m, 2H), 7.22~7.28 (m, 3H), 7.04 (d, J = 8.8 Hz, 1H), 6.92 (d, J = 8.8 Hz, 1H), 6.52 (t, J = 5.2 Hz, 1H), 6.27 (d, J = 4.8 Hz, 1H), 4.88~4.94 (m, 2H), 4.06 (s, 1H), 3.95 (s, 1H), 3.44 (s, 3H), 3.05 (d, J = 4.8 Hz, 3H), 2.82 (s, 3H). | 726 |

Examples 25 and 26

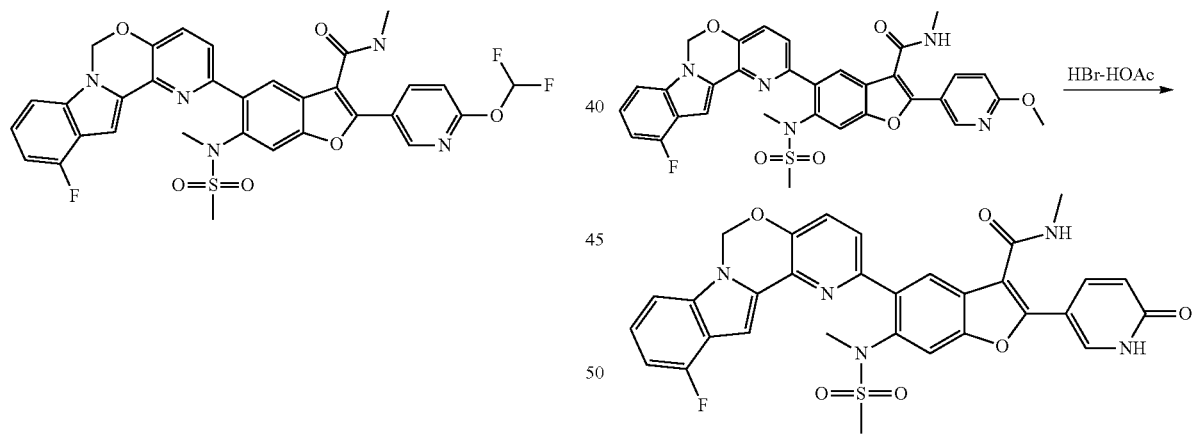

Step 1 - Synthesis of 5-(11-fluoro-6H-pyrido[2',3':5,6][1,3]oxazino[3,4-a]indol-2-yl)-N-methyl-6-(N-methylmethylsulfonamido)-2-(6-oxo-1,6-dihydropyridin-3-yl)benzofuran-3-carboxamide

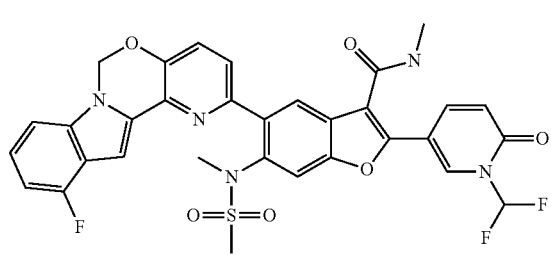

To a solution of 5-(11-fluoro-6H-pyrido[2',3':5,6][1,3]oxazino[3,4-a]indol-2-yl)-2-(6-methoxypyridin-3-yl)-N-methyl-6-(N-methylmethylsulfonamido)benzofuran-3-carboxamide (40 mg, 0.64 mmol) in HOAc (4 mL) was added HBr—HOAc (4 ml) at 0° C. Then the mixture was stirred at 80° C. for 2 hours. After the solvent was removed by vacuum, the residue was washed with Na₂CO₃ (a.q.), extracted with DCM, dried over Na₂SO₄, filtrated and concentrated in vacuo. The residue was purified by prep-HPLC to give the product 5-(11-fluoro-6H-pyrido[2',3':5,6][1,3]oxazino[3,4-a]indol-2-yl)-N-methyl-6-(N-methylmethylsulfonamido)-2-(6-oxo-1,6-dihydropyridin-3-yl)benzofuran-3-carboxamide (20 mg, yield: 50%). ¹H-NMR (MeOD, 400 MHz) δ 8.33 (s, 1H), 7.96 (q, J=9.6 Hz, 1H), 7.84 (s, 1H), 7.88 (s, 1H), 7.55 (d, J=9.6 Hz, 2H), 7.28 (d, J=9.6 Hz, 1H), 7.15~7.21 (m, 2H), 6.87 (q, J=9.6 Hz, 1H), 6.53 (t, J=9.6 Hz, 1H), 6.06 (s, 2H), 3.31 (s, 3H), 2.95 (d, J=9.6 Hz, 3H), 2.85 (s, 3H). MS (M+H)+: 614.

Step 2 - Synthesis of 2-(6-(difluoromethoxy)pyridin-3-yl)-5-(11-fluoro-6H-pyrido[2′,3′:5,6][1,3]oxazino[3,4-a]indol-2-yl)-N-methyl-6-(N-methylmethylsulfonamido)benzofuran-3-carboxamide (Compound 25) & 2-(1-(difluoromethyl)-6-oxo-1,6-dihydropyridin-3-yl)-5-(11-fluoro-6H-pyrido[2′,3′:5,6][1,3]oxazino[3,4-a]indol-2-yl)-N-methyl-6-(N-methylmethylsulfonamido)benzofuran-3-carboxamide (Compound 26)

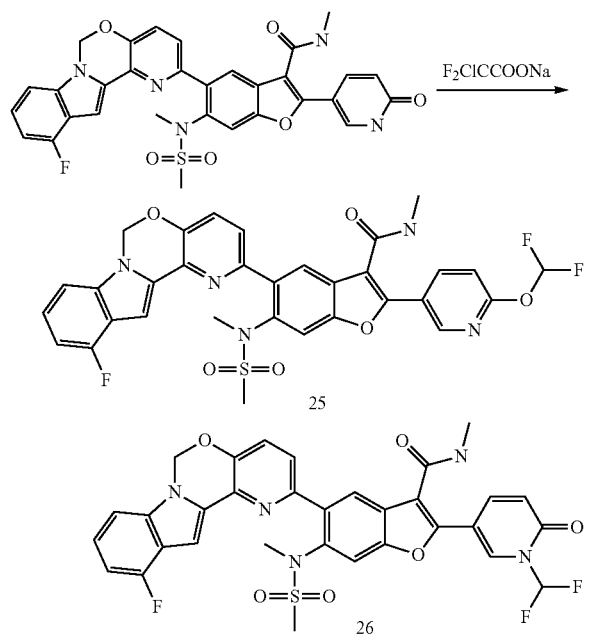

To a suspension of 5-(11-fluoro-6H-pyrido[2′,3′:5,6][1,3] oxazino[3,4-a]indol-2-yl)-N-methyl-6-(N-methylmethylsulfonamido)-2-(6-oxo-1,6-dihydropyridin-3-yl)benzofuran-3-carboxamide (40 mg, 0.06 mmol) in MeCN (5 mL) was added F₂ClCCOONa (20 mg, 0.13 mol) under N₂, and then the mixture was stirred at 100° C. for 12 hours. After concentrated in vacuo, the resulting residue was suspended in H₂O and extracted with DCM. The combined organic layer was washed with H₂O, brine, dried over Na₂SO₄, filtrated and concentrated in vacuo. The residue was purified by prep-HPLC to give the product of 2-(6-(difluoromethoxy)pyridin-3-yl)-5-(11-fluoro-6H-pyrido[2′,3′:5,6][1,3]oxazino[3,4-a]indol-2-yl)-N-methyl-6-(N-methylmethylsulfonamido) benzofuran-3-carboxamide and 2-(1-(difluoromethyl)-6-oxo-1,6-dihydropyridin-3-yl)-5-(11-fluoro-6H-pyrido[2′,3′:5,6][1,3]oxazino[3,4-a]indol-2-yl)-N-methyl-6-(N-methylmethylsulfonamido)benzofuran-3-carboxamide. 2-(6-(difluoromethoxy)pyridin-3-yl)-5-(11-fluoro-6H-pyrido[2′,3′:5,6][1,3]oxazino[3,4-a]indol-2-yl)-N-methyl-6-(N-methylmethylsulfonamido)benzofuran-3-carboxamide (20 mg, yield: 47%). ¹H-NMR (CDCl₃, 400 MHz) δ 8.84 (d, J=2.0 Hz, 1H), 8.43~8.47 (m, 1H), 7.96 (s, 1H), 7.73 (s, 0.25H), 7.69 (s, 1H), 7.55 (s, 0.5H), 7.50~7.52 (m, 2H), 7.37 (s, 0.25H), 7.20~7.24 (m, 2H), 7.13 (d, J=4.4 Hz, 1H), 7.04 (d, J=4.2 Hz, 1H), 6.84~6.87 (m, 1H), 6.07 (s, 1H), 5.99 (s, 2H), 3.35 (s, 3H), 3.05 (d, J=4.8 Hz, 3H), 2.78 (s, 3H). MS (M+H)+: 664. 2-(1-(difluoromethyl)-6-oxo-1,6-dihydropyridin-3-yl)-5-(11-fluoro-6H-pyrido[2′,3′:5,6][1,3]oxazino[3, 4-a]indol-2-yl)-N-methyl-6-(N-methylmethylsulfonamido) benzofuran-3-carboxamide (10 mg, yield: 23%). ¹H-NMR (CDCl₃, 400 MHz) δ 8.67 (d, J=2.0 Hz, 1H), 8.12~8.15 (m, 1H), 7.92 (s, 1H), 7.76 (s, 0.25H), 7.69 (s, 0.5H), 7.61 (s, 0.25H), 7.51~7.53 (m, 2H), 7.50 (s, 1H), 7.21~7.24 (m, 2H), 7.14 (d, J=8.0 Hz, 1H), 6.84~6.89 (m, 1H), 6.67 (d, J=8.0 Hz, 1H), 6.14 (s, 1H), 6.02 (s, 2H), 3.35 (s, 3H), 3.08 (d, J=4.8 Hz, 3H), 2.81 (s, 3H). MS (M+H)+: 664.

Example 27

5-(11-fluoro-6H-pyrido[2′,3′:5,6][1,3]oxazino[3,4-a] indol-2-yl)-2-(6-(4-fluorophenoxy)pyridin-3-yl)-N-methyl-6-(N-methylmethylsulfonamido)benzofuran-3-carboxamide

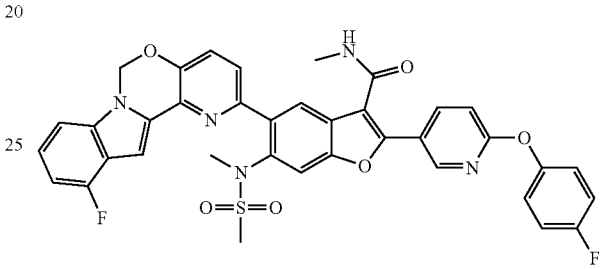

Step 1 - Synthesis of 6-amino-5-bromo-2-(6-fluoropyridin-3-yl)-N-methylbenzofuran-3-carboxamide

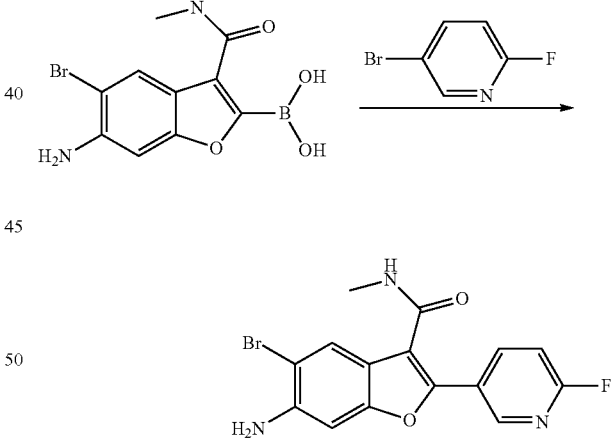

To a solution of (6-amino-5-bromo-3-(methylcarbamoyl) benzofuran-2-yl)boronic acid (500 mg, 1.61 mmol) in dioxane/H₂O (5 mL/0.5 mL) was added 5-bromo-2-fluoropyridine (420 mg, 2.42 mmol), Pd(dppf)Cl₂(10 mg) and K₃PO₄.3H₂O (855 mg, 3.21 mmol). The mixture was stirred at 50° C. for 10 h. The mixture was evaporated and washed with MeOH to obtain the yellow solid as the product of 6-amino-5-bromo-2-(6-fluoropyridin-3-yl)-N-methylbenzofuran-3-carboxamide (300 mg, yield: 51%). ¹H-NMR (DMSO-d6, 400 MHz) δ 8.76 (s, 1H), 8.44~8.51 (m, 2H), 7.75 (s, 1H), 7.39~7.42 (m, 1H), 7.09 (s, 1H), 5.71 (s, 2H), 2.88 (d, J=8.4 Hz, 3H). (M+H)+: 364/366.

Step 2 - Synthesis of 6-amino-5-bromo-2-(6-(4-(fluorophenoxy)pyridin-3-yl)-N-methylbenzofuran-3-carboxamide

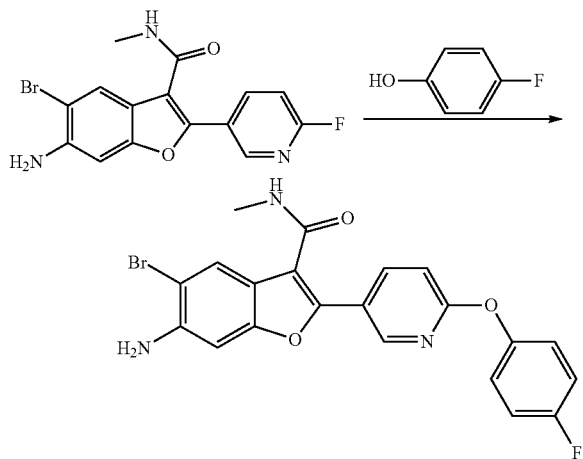

To a degassed solution of 6-amino-5-bromo-2-(6-fluoropyridin-3-yl)-N-methylbenzofuran-3-carboxamide (500 mg, 1.41 mmol) and 4-fluorophenol (460 mg, 5.21 mmol) in DMF/THF (1 mL/7 mL) was added $K_2CO_3$ (260 mg, 5.62 mmol) under $N_2$. The mixture was heated at 90° C. for 8 h. The reaction mixture was concentrated in vacuo and it was extracted with EtOAc. It was washed with $H_2O$, brine and dried over $Na_2SO_4$. After being concentrated, the residue was purified by column chromatography (PE:EA=4:1) to give the product of 6-amino-5-bromo-2-(6-(4-fluorophenoxy)pyridin-3-yl)-N-methylbenzofuran-3-carboxamide (380 mg, yield: 61%). $^1$H-NMR (CDCl$_3$, 400 MHz) δ 8.61 (d, J=2.4 Hz, 1H), 8.23~8.25 (m, 1H), 7.74 (s, 1H), 7.02~7.09 (m, 4H), 6.91 (d, J=8.8 Hz, 1H), 8.85 (d, J=4.8 Hz, 1H), 5.76 (s, 1H), 4.20 (s, 2H), 2.95 (d, J=5.2 Hz, 3H). (M+H)$^+$: 456/458.

Step 3 - Synthesis of 5-bromo-2-(6-(4-fluorophenoxy)pyridin-3-yl)-N-methyl-6-(methylsulfonamido)benzofuran-3-carboxamide

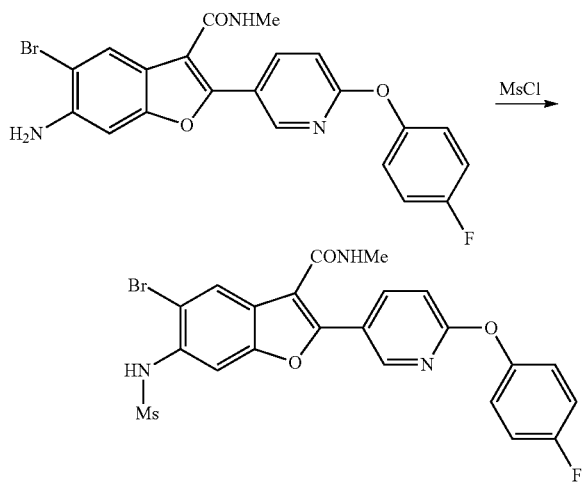

To a degassed solution of 6-amino-5-bromo-2-(6-(4-fluorophenoxy)pyridin-3-yl)-N-methylbenzofuran-3-carboxamide (100 mg, 0.22 mmol) and DMAP (10 mg, 0.02 mmol) in Pyridine (5 ml) under $N_2$ was added MsCl (32 mg, 0.38 mmol) at 0° C. Then it was stirred at 20° C. for 15 h. The reaction mixture was concentrated and extracted with DCM. After it was washed with brine, dried over $Na_2SO_4$ and concentrated, the residue was purified by prep-TLC to give 5-bromo-2-(6-(4-fluorophenoxy)pyridin-3-yl)-N-methyl-6-(methylsulfonamido)benzofuran-3-carboxamide (100 mg, yield: 85%). $^1$H-NMR (CDCl$_3$, 400 MHz) δ 9.65 (s, 1H), 8.73 (s, 1H), 8.54 (d, J=4.8 Hz, 1H), 8.39 (d, J=2.8 Hz, 1H), 8.03 (s, 1H), 7.84 (s, 1H), 7.33~7.38 (m, 4H), 7.28 (d, J=8.8 Hz, 1H). (M+H)$^+$: 534/536.

Step 4 - Synthesis of 5-bromo-2-(6-(4-fluorophenoxy)pyridin-3-yl)-N-methyl-6-(N-methylmethylsulfonamido)benzofuran-3-carboxamide

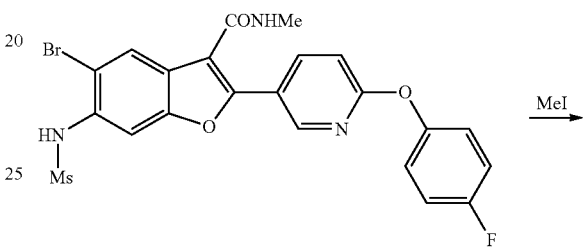

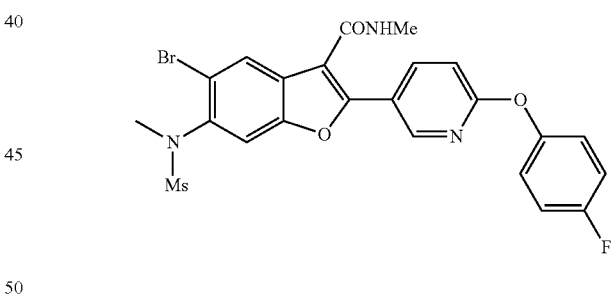

To a degassed solution of 5-bromo-2-(6-(4-fluorophenoxy)pyridin-3-yl)-N-methyl-6-(methylsulfonamido)benzofuran-3-carboxamide (100 mg, 0.187 mmol) and $K_2CO_3$ (53 mg, 0.374 mmol) in DMSO (2 mL) was added MeI (27 mg, 0.187 mmol) under $N_2$. The mixture was heated at 20° C. for 2 h. The reaction mixture was diluted with $H_2O$ and extracted with EtOAc. It was washed with $H_2O$, brine and dried over $Na_2SO_4$. After concentrated, the residue was purified by column chromatography (PE:EA=2:1) to give the product of 5-bromo-2-(6-(4-fluorophenoxy)pyridin-3-yl)-N-methyl-6-(N-methylmethylsulfonamido)benzofuran-3-carboxamide (20 mg, yield: 20%). $^1$H-NMR (CDCl$_3$, 400 MHz) δ 8.63 (d, J=2.8 Hz, 1H), 8.21~8.24 (m, 1H), 8.02 (s, 1H), 7.65 (s, 1H), 7.06~7.08 (m, 3H), 6.98 (d, J=8.8 Hz, 1H), 5.77 (d, J=8.8 Hz, 1H), 3.27 (s, 3H), 3.03 (s, 3H), 2.96 (d, J=4.8 Hz, 3H). MS (M+H)$^+$: 548/550.

Step 5 - Synthesis of 2-(6-(4-fluorophenoxy)pyridin-3-yl)-N-methyl-6-(N-methylmethylsulfonamido)-5-(4,4,5,5-tetramethyl-1,3,2-dioxaborolan-2-yl)benzofuran-3-carboxamide

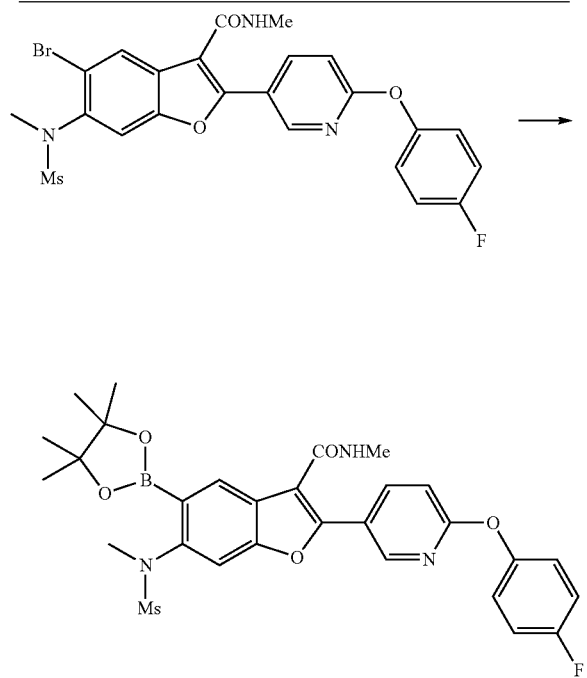

To a degassed solution of 5-bromo-2-(6-(4-fluorophenoxy)pyridin-3-yl)-N-methyl-6-(N-methylmethylsulfonamido)benzofuran-3-carboxamide (50 mg, 0.09 mmol) and 4,4,5,5-tetramethyl-2-(4,4,5,5,-tetramethyl-1,3,2-dioxaborolan-2-yl)-1,3,2-dioxaborolane (115 mg, 0.46 mmol) in 1,4-dioxane (1 mL) was added Pd(dppf)Cl₂ (10 mg) and KOAc (27 mg, 0.27 mmol) under N₂. The mixture was heated at a pre-heated oil-bath at 100° C. for 3 h. The reaction mixture was concentrated in vacuo and it was extracted with EtOAc. The residue was washed with H₂O, brine and dried over Na₂SO₄. After being concentrated, the crude product was purified by prep-TLC (PE:EA=1:1) to give 2-(6-(4-fluorophenoxy)pyridin-3-yl)-N-methyl-6-(N-methylmethylsulfonamido)-5-(4,4,5,5-tetramethyl-1,3,2-dioxaborolan-2-yl)benzofuran-3-carboxamide (20 mg, yield: 37%). MS (M+H)⁺: 596.

Step 6 - Synthesis of 5-(11-fluoro-6H-pyrido[2',3':5,6][1,3]oxazino[3,4-a]indol-2-yl)-2-(6-(4-fluorophenoxy)pyridin-3-yl)-N-methyl-6-(N-methylmethylsulfonamido)benzofuran-3-carboxamide (Compound 27)

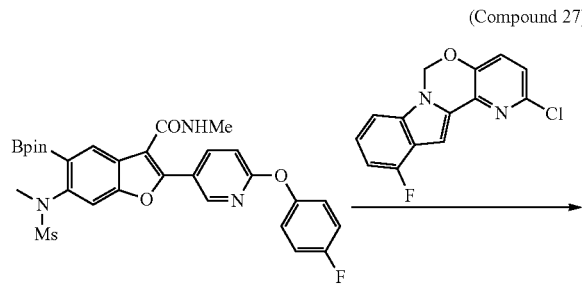

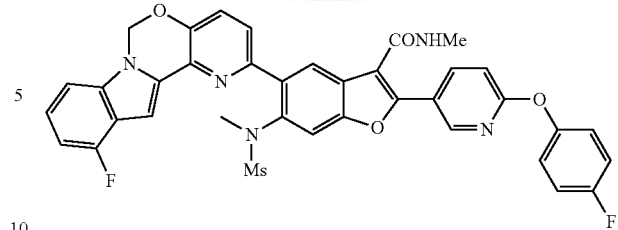

To a stirring mixture of 2-(6-(4-fluorophenoxy)pyridin-3-yl)-N-methyl-6-(N-methylmethylsulfonamido)-5-(4,4,5,5-tetramethyl-1,3,2-dioxaborolan-2-yl)benzofuran-3-carboxamide (50 mg, 0.09 mmol), 2-chloro-11-fluoro-6H-pyrido[2',3':5,6][1,3]oxazino[3,4-a]indole (28 mg, 0.10 mmol) and Na₂CO₃ (18 mg, 0.17 mmol) in dioxane (0.8 mL) was added X-Phos (5 mg) and Pd₂(dba)₃ (5 mg) under N₂ protection. The mixture was stirred at a pre-heated oil-bath 100° C. for 3 h. The mixture was concentrated and the residue was extracted with EA. The residue was washed with H₂O, brine and dried over Na₂SO₄. After concentrated, the crude product was purified by prep-HPLC to give the product of 5-(11-fluoro-6H-pyrido[2',3':5,6][1,3]oxazino[3,4-a]indol-2-yl)-2-(6-(4-fluorophenoxy)pyridin-3-yl)-N-methyl-6-(N-methylmethylsulfonamido)benzofuran-3-carboxamide (20 mg, yield: 30%). ¹H-NMR (CDCl₃, 400 MHz) δ 8.70 (d, J=2.0 Hz, 1H), 8.31~8.34 (m, 1H), 7.91 (s, 1H), 7.62 (s, 1H), 7.44 (s, 2H), 7.15 (s, 2H), 7.04~7.10 (m, 5H), 6.98 (d, J=8.8 Hz, 1H), 6.76~6.81 (m, 1H), 5.94 (s, 2H), 5.90 (d, J=8.8 Hz, 1H), 3.30 (s, 3H), 2.96 (d, J=4.8 Hz, 3H), 2.70 (s, 3H). MS (M+H)⁺: 708.

Example 28

2-(4-(difluoromethyl)phenyl)-5-(11-fluoro-6H-pyrido[2',3':5,6][1,3]oxazino[3,4-a]indol-2-yl)-N-methyl-6-(N-methylmethylsulfonamido)benzofuran-3-carboxamide

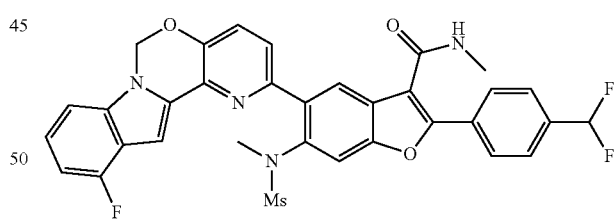

Step 1 - Synthesis of 5-bromo-2-(4-formylphenyl)-N-methyl-6-(N-methylmethylsulfonamido)benzofuran-3-carboxamide

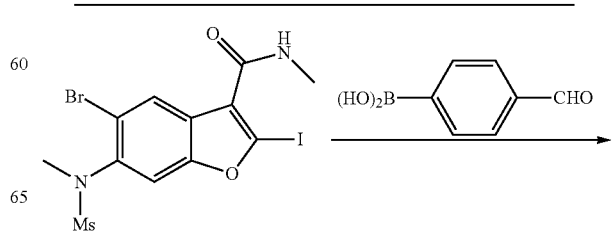

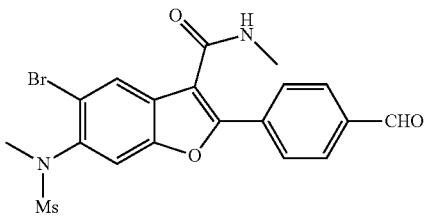

To a degassed solution of compound 5-bromo-2-iodo-N-methyl-6-(N-methylmethylsulfonamido)benzofuran-3-carboxamide (400 mg, 0.82 mmol), (4-formylphenyl)boronic acid (110 mg, 0.74 mmol) and Na$_2$CO$_3$ (174 mg, 1.6 mmol) in DMF (4 mL) was added Pd(dppf)Cl$_2$ (20 mg) under N$_2$, and the mixture was stirred at 100° C. for 2 h. After the solvent was removed, the residue was purified by column chromatography (DCM:EtOAc=10:1) to give the product of compound 5-bromo-2-(4-formylphenyl)-N-methyl-6-(N-methylmethylsulfonamido)benzofuran-3-carboxamide (200 mg, yield: 52%). $^1$H-NMR (CDCl$_3$, 400 MHz) 10.09 (s, 1H), 8.09~8.15 (m, 3H), 8.02 (s, 2H), 7.75 (s, 1H), 5.90 (s, 1H), 3.36 (s, 3H), 3.11 (s, 3H), 3.05 (d, J=4.8 Hz, 3H). MS (M+H)$^+$: 465/467.

Step 2 - Synthesis of 5-bromo-2-(4-(difluoromethyl)phenyl)-N-methyl-6-(N-methylmethylsulfonamido)benzofuran-3-carboxamide

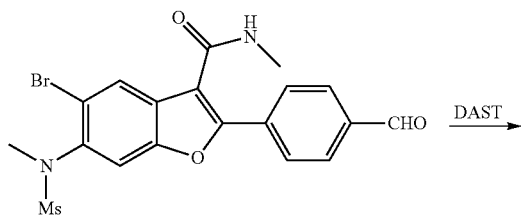

To a solution of 5-bromo-2-(4-formylphenyl)-N-methyl-6-(N-methylmethylsulfonamido)benzofuran-3-carboxamide (50 mg, 0.1 mmol) in DCM (1 mL) was added dropwise DAST (0.2 mL) at −78° C. Then the mixture was stirred at 25° C. for 5 hours. Then MeOH (3 ml) was added, and the mixture was adjusted to pH=7, extracted with DCM (10 ml). The organic phase was dried over Na$_2$SO$_4$. After concentrated in vacuo, the residue was purified by prep-TLC (DCM:EtOAc=10:1) to give the product of compound 5-bromo-2-(4-(difluoromethyl)phenyl)-N-methyl-6-(N-methylmethylsulfonamido)benzofuran-3-carboxamide (26 mg, yield: 50%). $^1$H-NMR (CDCl$_3$, 400 MHz) δ 8.16 (s, 1H), 7.99 (d, J=8.0 Hz, 2H), 7.73 (s, 1H), 7.66 (d, J=8.0 Hz, 2H), 6.56~6.88 (m, 1H), 5.85 (s, 1H), 3.35 (s, 3H), 3.10 (s, 3H), 3.02 (d, J=5.2 Hz, 3H). MS (M+H)$^+$: 487/489.

Step 3 - Synthesis of 2-(4-(difluoromethyl)phenyl)-N-methyl-6-(N-methylmethylsulfonamido)-5-(4,4,5,5-tetramethyl-1,3,2-dioxaborolan-2-yl)benzofuran-3-carboxamide

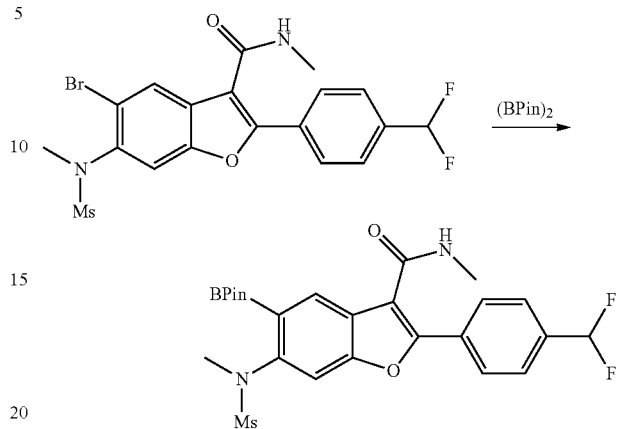

To a degassed solution of 5-bromo-2-(4-(difluoromethyl)phenyl)-N-methyl-6-(N-methylmethylsulfonamido)benzofuran-3-carboxamide (50 mg, 0.1 mmol), KOAc (30 mg, 0.3 mmol) and dis(pinacolato)diboron (130 mg, 0.5 mmol) in 1,4-dioxane (2 mL) and H$_2$O (0.1 mL) was added Pd(dppf)Cl$_2$ (5 mg) under N$_2$, and the mixture was stirred at 130° C. for 3 hours. After the solvent was removed, the residue was purified by column chromatography (DCM:EtOAc=10:1) to give the product of 2-(4-(difluoromethyl)phenyl)-N-methyl-6-(N-methylmethylsulfonamido)-5-(4,4,5,5-tetramethyl-1,3,2-dioxaborolan-2-yl)benzofuran-3-carboxamide (30 mg, yield: 55%). $^1$H-NMR (CDCl$_3$, 400 MHz) δ 8.16 (s, 1H), 7.99 (d, J=8.0 Hz, 2H), 7.73 (s, 1H), 7.66 (d, J=80 Hz, 2H), 6.56~6.88 (m, 1H), 5.85 (br s., 1H), 3.35 (s, 3H), 3.10 (s, 3H), 3.02 (d, J=5.2 Hz, 3H), 1.33 (s, 12H). MS (M+H)$^+$: 535.

Step 4 - Synthesis of 2-(4-(difluoromethyl)phenyl)-5-(11-fluoro-6H-pyrido[2',3':5,6][1,3]oxazino[3,4-a]indol-2-yl)-N-methyl-6-(N-methylmethylsulfonamido)benzofuran-3-carboxamide

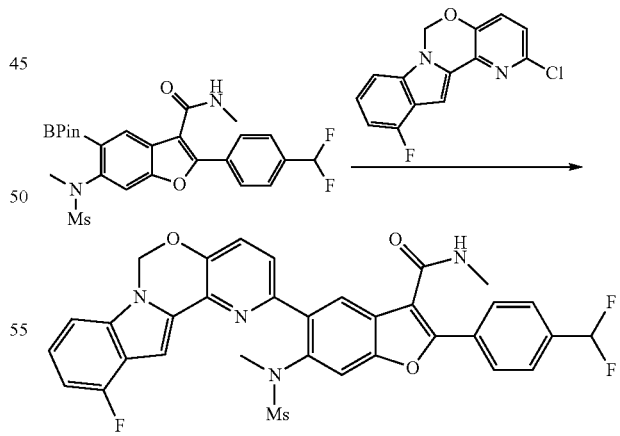

To a degassed solution of 2-(4-(difluoromethyl)phenyl)-N-methyl-6-(N-methylmethylsulfonamido)-5-(4,4,5,5-tetramethyl-1,3,2-dioxaborolan-2-yl)benzofuran-3-carboxamide (100 mg, 0.18 mmol), 2-chloro-11-fluoro-6H-pyrido[2',3':5,6][1,3]oxazino[3,4-a]indole (50 mg, 0.20 mmol), Na$_2$CO$_3$ (39 mg, 0.37 mmol), in 1,4-dioxane (3 mL) and H$_2$O (0.1 mL) were added Pd$_2$(dba)$_3$ (5 mg) and X-Phos (5 mg) under N$_2$.

Then the mixture was stirred at 100° C. for 2 hours. The reaction mixture was cooled to RT and filtered. The filtrate was washed with H₂O and dried over Na₂SO₄. After being concentrated, the residue was purified by prep-HPLC to give the product of 2-(4-(difluoromethyl)phenyl)-5-(11-fluoro-6H-pyrido[2',3':5,6][1,3]oxazino[3,4-a]indol-2-yl)-N-methyl-6-(N-methylmethylsulfonamido)benzofuran-3-carboxamide (50 mg, yield: 41%). $^1$H-NMR (CDCl$_3$, 400 MHz) δ 8.08 (d, J=7.6 Hz, 2H), 8.05 (s, 1H), 7.73 (s, 1H), 7.69 (d, J=8.0 Hz, 2H), 7.53 (s, 2H), 7.30 (s, 1H), 7.25 (d, J=2.8 Hz, 1H), 7.16 (d, J=8.0 Hz, 1H), 6.88~6.93 (m, 1H), 6.75 (s, 1H), 6.09 (d, J=4.4 Hz, 1H), 6.04 (s, 2H), 3.41 (s, 3H), 3.04 (d, J=4.8 Hz, 3H), 2.79 (s, 3H). MS (M+H)$^+$: 647.

Example 29

2-(4-cyanophenyl)-5-(11-fluoro-6H-pyrido[2',3':5,6][1,3]oxazino[3,4-a]indol-2-yl)-N-methyl-6-(N-methylmethylsulfonamido)benzofuran-3-carboxamide

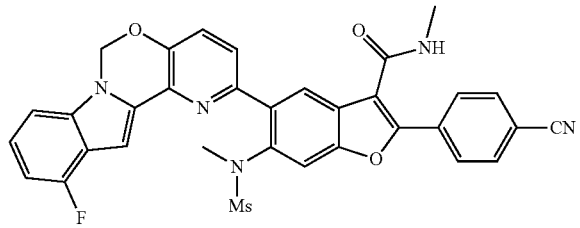 [SMILES: CNC(=O)c1c(-c2ccc(C#N)cc2)oc2cc(N(C)S(C)(=O)=O)c(-c3ccc4c(n3)-c3cc5c(F)cccc5n3CO4)cc12]

Step 1 - Synthesis of 6-amino-5-bromo-2-(4-cyanophenyl)-N-methylbenzofuran-3-carboxamide

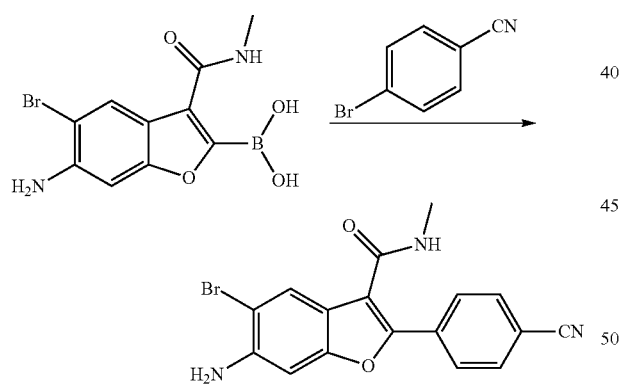

A solution of (6-amino-5-bromo-3-(methylcarbamoyl)benzofuran-2-yl)boronic acid (1 g, 3.19 mmol), 4-bromobenzonitrile (1.17 g, 6.39 mmol), K₃PO₄·3H₂O (1.7 g, 6.39 mmol) and Pd(dppf)Cl₂ (40 mg) in dioxane/H₂O (10 mL/2 mL) was stirred at 80° C. for 4 h. The mixture was filtered to remove the solid and then the mixture was diluted with water and extracted with EA. The organic layer was washed with brine, dried with Na₂SO₄ and concentrated. The residue was purified by column chromatography (PE:EA=5:1) to give 6-amino-5-bromo-2-(4-cyanophenyl)-N-methylbenzofuran-3-carboxamide (300 mg, yield: 26%). $^1$H-NMR (CDCl$_3$, 400 MHz) δ 8.09 (d, J=8.0 Hz, 2H), 7.72 (s, 1H), 7.65 (d, J=8.4 Hz, 2H), 6.84 (s, 1H), 5.84 (s, 1H), 4.28 (s, 2H), 3.00 (d, J=4.4 Hz, 3H). MS (M+H)$^+$: 370/372.

Step 2 - Synthesis of 5-bromo-2-(4-cyanophenyl)-N-methyl-6-(methylsulfonamido)benzofuran-3-carboxamide

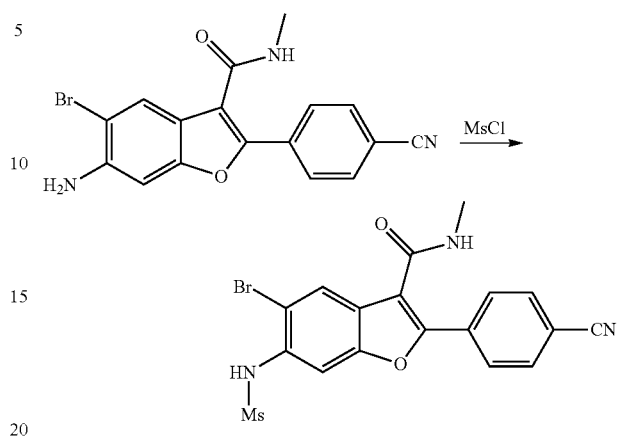

A mixture of 6-amino-5-bromo-2-(4-cyanophenyl)-N-methylbenzofuran-3-carboxamide (300 mg, 0.80 mmol) in DCM (2 mL) and pyridine (2 mL) was stirred at room temperature and MsCl (278 mg, 2.4 mmol) was added dropwise. The reaction was stirred at room temperature for 8 h. The reaction was washed with 1N HCl and extracted with DCM, dried with Na₂SO₄ and concentrated to give 5-bromo-2-(4-cyanophenyl)-N-methyl-6-(methylsulfonamido)benzofuran-3-carboxamide (260 mg, yield: 72%). MS (M+H)$^+$: 448/450.

Step 3 - Synthesis of 5-bromo-2-(4-cyanophenyl)-N-methyl-6-(N-methylmethylsulfonamido)-benzofuran-3-carboxamide

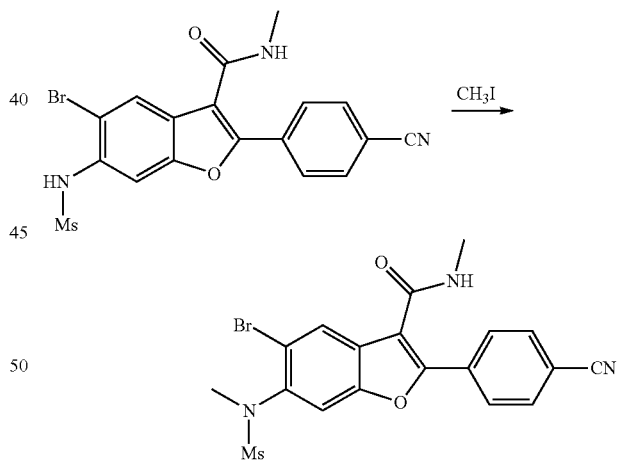

A solution of 5-bromo-2-(4-cyanophenyl)-N-methyl-6-(methylsulfonamido)benzofuran-3-carboxamide (200 mg, 0.44 mmol), K₂CO₃ (124 mg, 1.89 mmol) in DMF (5 mL) was stirred at RT and CH₃I (182 mg, 1.32 mmol) was added dropwise. The reaction was stirred at RT for 3 h. The reaction was concentrated, washed with H₂O and filtered to give 5-bromo-2-(4-cyanophenyl)-N-methyl-6-(N-methylmethylsulfonamido)benzofuran-3-carboxamide (150 mg, yield: 73%). $^1$H-NMR (CDCl$_3$, 400 MHz) δ 8.09 (s, 1H), 8.07 (d, J=8.0 Hz, 2H), 7.78 (s, 1H), 7.76 (s, 1H), 7.74 (s, 1H), 5.88 (s, 1H), 3.34 (s, 3H), 3.10 (s, 3H), 3.05 (d, J=5.2 Hz, 3H). MS (M+H)$^+$: 462/464.

Step 4 - Synthesis of 2-(4-cyanophenyl)-N-methyl-6-(N-methylmethylsulfonamido)-5-(4,4,5,5-tetramethyl-1,3,2-dioxaborolan-2-yl)benzofuran-3-carboxamide Step 5 - Synthesis of 2-(4-cyanophenyl)-5-(11-fluoro-6H-pyrido[2',3':5,6][1,3]oxazino[3,4-a]indol-2-yl)-N-methyl-6-(N-methylmethylsulfonamido)benzofuran-3-carboxamide

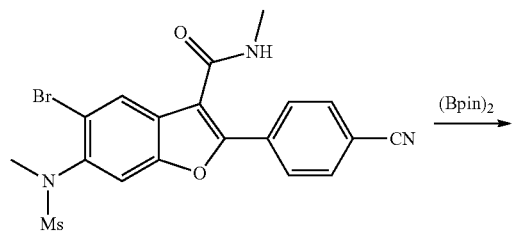

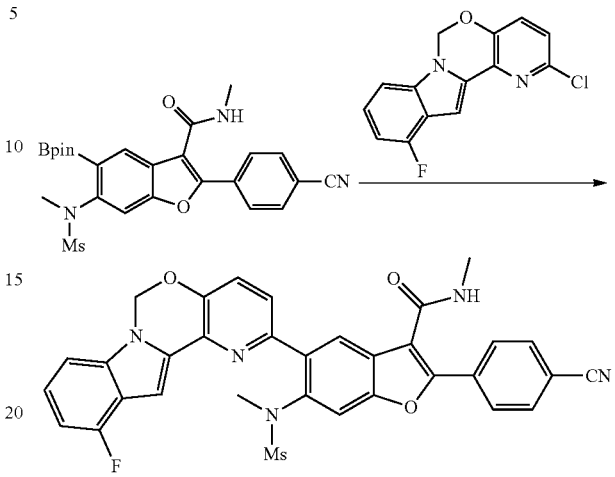

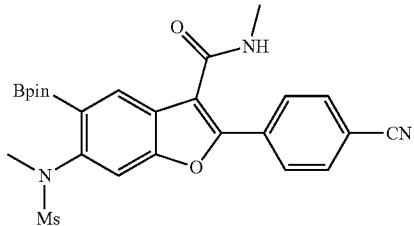

A solution of 5-bromo-2-(4-cyanophenyl)-N-methyl-6-(N-methylmethylsulfonamido)benzofuran-3-carboxamide (200 mg, 0.32 mmol), 4,4,5,5-tetramethyl-2-(4,4,5,5,-tetramethyl-1,3,2-dioxaborolan-2-yl)-1,3,2-dioxaborolane (549 mg, 2.16 mmol), KOAc (84 mg, 0.87 mmol) and Pd(dppf)Cl₂ (25 mg) in dioxane/H₂O (5 mL/1 mL) was stirred at 130° C. for 3 h. The reaction was filtered to remove the solid and then the mixture was diluted with water and extracted with EA. The organic layer was washed with brine, dried over Na₂SO₄ and concentrated. The residue was purified by prep-HPLC to give 2-(4-cyanophenyl)-N-methyl-6-(N-methylmethylsulfonamido)-5-(4,4,5,5-tetramethyl-1,3,2-dioxaborolan-2-yl)benzofuran-3-carboxamide (115 mg, yield: 52%). MS (M+H)⁺: 510.

To a solution of 2-(4-cyanophenyl)-N-methyl-6-(N-methylmethylsulfonamido)-5-(4,4,5,5-tetramethyl-1,3,2-dioxaborolan-2-yl)benzofuran-3-carboxamide (115 mg, 0.22 mmol), 2-chloro-11-fluoro-6H-pyrido[2',3':5,6][1,3]oxazino[3,4-a]indole (75 mg, 0.27 mmol) K₂CO₃ (60 mg, 0.44 mmol), Pd₂(dba)₃ (30 mg) and X-Phos (30 mg) in dioxane/H₂O (3 mL/0.6 mL) was stirred at 100° C. for 3 h. The reaction was filtered to remove the solid and then the mixture was diluted with water and extracted with EA. The organic layer was washed with brine, dried over Na₂SO₄ and concentrated. The residue was purified by prep-HPLC to get the product of 2-(4-cyanophenyl)-5-(11-fluoro-6H-pyrido[2',3':5,6][1,3]oxazino[3,4-a]indol-2-yl)-N-methyl-6-(N-methylmethylsulfonamido)benzofuran-3-carboxamide (30 mg, yield: 21%). ¹H-NMR (CDCl₃, 400 MHz) δ 8.16 (d, J=8.4 Hz, 2H), 7.96 (s, 1H), 7.78 (d, J=8.4 Hz, 2H), 7.70 (s, 1H), 7.23~7.19 (m, 3H), 7.13 (d, J=8.4 Hz, 2H), 6.87 (m, 1H), 6.14 (d, J=4.4 Hz, 1H), 6.00 (s, 2H), 3.35 (s, 3H), 3.05 (d, J=5.2 Hz, 3H), 2.77 (s, 3H). MS (M+H)⁺: 622.

Examples 30-31

Examples 30-31, depicted in the table below, were prepared in accordance with the method described in Example 29.

| Example | Structure | NMR | MS (M + H)⁺ |
|---|---|---|---|
| 30 | 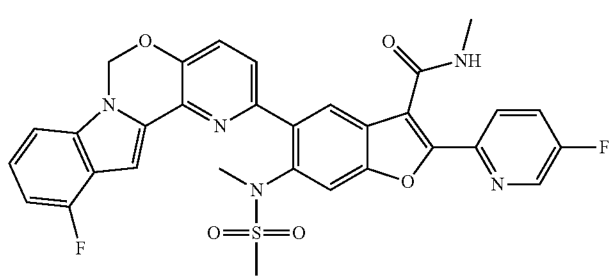 [SMILES: CNC(=O)c1c(-c2ccc(F)cn2)oc2cc(N(C)S(C)(=O)=O)c(-c3ccc4c(n3)-c3cc5c(F)cccc5n3CO4)cc12] | ¹H-NMR (CDCl₃, 400 MHz) δ 10.96 (d, J = 4.0 Hz, 3H), 8.73 (s, 1H), 8.51 (d, J = 2.8 Hz, 1H), 8.18~8.21 (m, 1H), 7.63~7.67 (m, 2H), 7.46 (d, J = 8.4 Hz, 1H), 7.41 (d, J = 8.4 Hz, 1H), 7.12~7.16 (m, 2H), 7.05 (d, J = 8.4 Hz, 1H), 6.78~6.81 (m, 1H), 5.94 (s, 1H), 3.37 (s, 3H), 2.99 (d, J = 4.80 Hz, 3H), 2.60 (s, 3H). | 616 |

| Example | Structure | NMR | MS (M + H)+ |
|---|---|---|---|
| 31 | 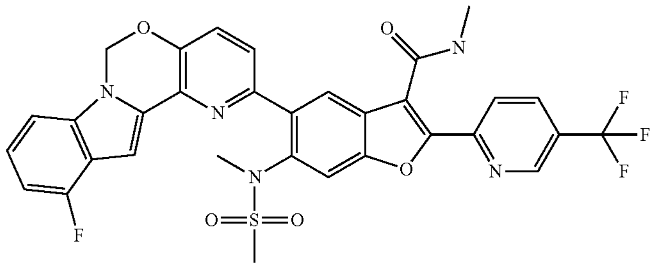 [SMILES: CNC(=O)c1c(-c2ccc(C(F)(F)F)cn2)oc2cc(N(C)S(C)(=O)=O)c(-c3ccc4c(n3)-c3cc5c(F)cccc5n3CO4)cc12] | 1H-NMR (CDCl3, 500 MHz) δ 11.01 (s, 1H), 8.99 (s, 1H), 8.83 (s, 1H), 8.38~8.22 (m, 2H), 7.77 (s, 1H), 7.54-7.48 (m, 2H), 7.21~7.11 (m, 2H), 7.2 (s, 1H), 6.85~6.81 (m, 1H), 6.01 (s, 2H), 3.42 (s, 3H), 3.08 (d, J = 4.8 Hz, 3H), 2.67 (s, 3H). | 666 |

Example 32

2-(3,6-dihydro-2H-thiopyran-4-yl)-5-(11-fluoro-6H-pyrido[2',3':5,6][1,3]oxazino[3,4-a]indol-2-yl)-N-methyl-6-(N-methylmethylsulfonamido)benzofuran-3-carboxamide

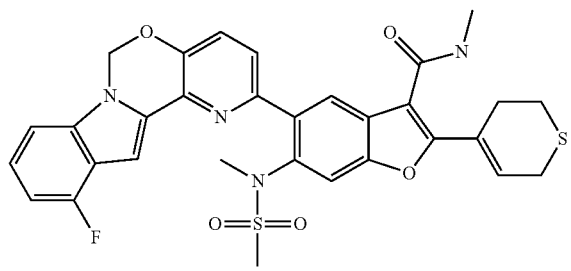 [SMILES: CNC(=O)c1c(C2=CCSCC2)oc2cc(N(C)S(C)(=O)=O)c(-c3ccc4c(n3)-c3cc5c(F)cccc5n3CO4)cc12]

Step 1 - 5-bromo-2-(3,6-dihydro-2H-thiopyran-4-yl)N-methyl-6-(N-methylmethylsulfonamido)benzofuran-3-carboxamide

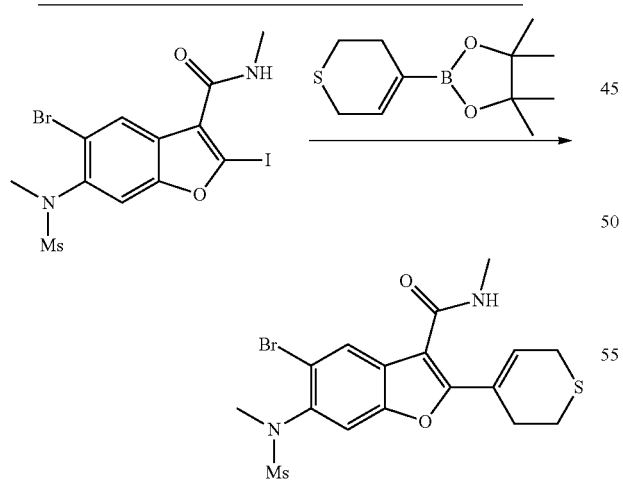

To a solution of 5-bromo-2-iodo-N-methyl-6-(N-methylmethylsulfonamido)benzofuran-3-carboxamide (800 mg, 1.6 mmol), 2-(3,6-dihydro-2H-thiopyran-4-yl)-4,4,5,5-tetramethyl-1,3,2-dioxaborolane (371 mg, 1.6 mmol) and Cs₂CO₃ (1.07 g, 3.28 mmol) in 1,4-dioxane (20 mL) was added Pd(dppf)Cl₂ (50 mg) and tri-o-tolylphosphine (50 mg) under nitrogen. The reaction mixture was heated at 100° C. for 4 h, concentrated in vacuo to remove 1,4-dioxane and purified by column chromatography (PE:EA=3:1) to give the compound 5-bromo-2-(3,6-dihydro-2H-thiopyran-4-yl)-N-methyl-6-(N-methylmethylsulfonamido)benzofuran-3-carboxamide (250 mg, yield: 33%). $^1$H-NMR (CDCl$_3$, 400 MHz) δ 8.09 (s, 1H), 7.59 (s, 1H), 6.73 (s, 1H), 6.06 (brs, 1H), 3.38 (t, J=2.0 Hz, 2H), 3.30 (s, 3H), 3.05 (s, 3H), 3.00 (d, J=4.8 Hz, 3H), 2.87 (t, J=5.6 Hz, 2H), 2.70~2.76 (m, 2H). MS (M+H)⁺: 459/461.

Step 2 - Synthesis of 11-fluoro-2-(trimethylstannyl)-6H-pyrido[2',3':5,6][1,3]oxazino[3,4-a]indole

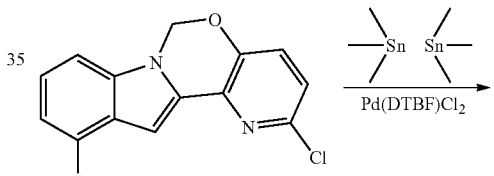

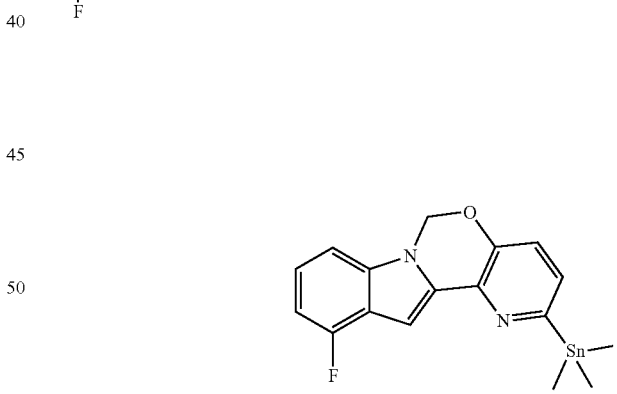

To a degassed solution of 2-chloro-11-fluoro-6H-pyrido[2',3':5,6][1,3]oxazino[3,4-a]indole (3.0 g, 10.92 mmol) in Toluene (80 mL), (Me₃Sn)₂ (5.4 g, 16.40 mmol) and Pd(DTBPF)Cl₂ (250 mg, 0.41 mmol) were added. The reaction mixture was stirred at 100° C. for 3.5 hours. The reaction mixture was filtered through a Celite pad. The filtrate was concentrated in vacuo and purified by aluminum oxide column chromatography (PE:EtOAc=30:1) to give 11-fluoro-2-(trimethylstannyl)-6H-pyrido[2',3':5,6][1,3]oxazino[3,4-a]indole (3.7 g, yield 84%). $^1$H-NMR (CDCl$_3$, 400 MHz) δ 7.3~57.31 (m, 2H), 7.26~7.16 (m, 2H), 7.08 (d, J=8.4 Hz, 1H), 6.84 (dd, J=8.4 Hz, 1H), 5.91 (s, 2H), 0.45~0.31 (m, 9H).

Step 3 - Synthesis of 2-(3,6-dihydro-2H-thiopyran-4-yl)-5-(11-fluoro-6H-pyrido[2',3':5,6][1,3]oxazino[3,4-a]indol-2-yl)-N-methyl-6-(N-methylmethylsulfonamido)benzofuran-3-carboxamide

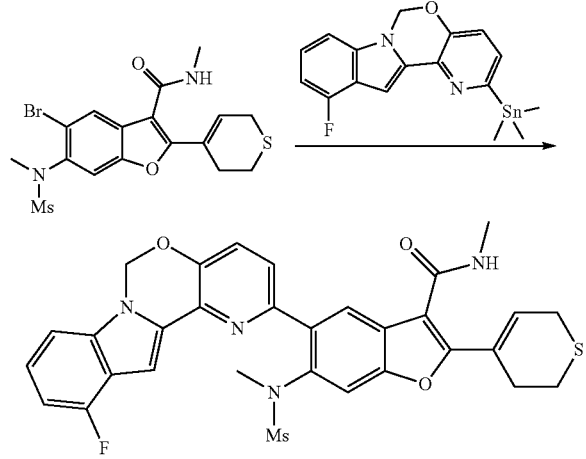

To a solution of 5-bromo-2-(3,6-dihydro-2H-thiopyran-4-yl)-N-methyl-6-(N-methylmethylsulfonamido)benzofuran-3-carboxamide (100 mg, 0.2 mmol), 11-fluoro-2-(trimethylstannyl)-6H-pyrido[2',3':5,6][1,3]oxazino[3,4-a]indole (105 mg, 0.26 mmol) in 1,4-dioxane (5 mL) was added Pd(PPh$_3$)$_4$ (10 mg) under nitrogen. The reaction mixture was heated at 100° C. overnight, concentrated in vacuo to remove 1,4-dioxane and purified by prep-TLC (PE:EA=1:1) to give 2-(3,6-dihydro-2H-thiopyran-4-yl)-5-(11-fluoro-6H-pyrido[2',3':5,6][1,3]oxazino[3,4-a]indol-2-yl)-N-methyl-6-(N-methylmethylsulfonamido)benzofuran-3-carboxamide (15 mg, yield: 11%). $^1$H-NMR (CDCl$_3$, 400 MHz) δ 7.97 (s, 1H), 7.58 (s, 1H), 7.47 (s, 2H), 7.18~7.23 (m, 2H), 7.11 (d, J=8.4 Hz, 1H), 6.80~6.86 (m, 2H), 6.05 (d, J=4.8 Hz, 1H), 5.99 (s, 2H), 3.41 (t, J=2.0 Hz, 2H), 3.35 (s, 3H), 3.00 (d, J=4.8 Hz, 3H), 2.90 (t, J=5.6 Hz, 2H), 2.80 (d, J=3.2 Hz, 2H), 2.71 (s, 3H). MS (M+H)$^+$: 619.

Examples 33-35

Examples 33~35 depicted in the table below, were prepared in accordance with the method described in Example 35.

| Example | Structure | NMR | MS (M + H)$^+$ |
|---|---|---|---|
| 33 | 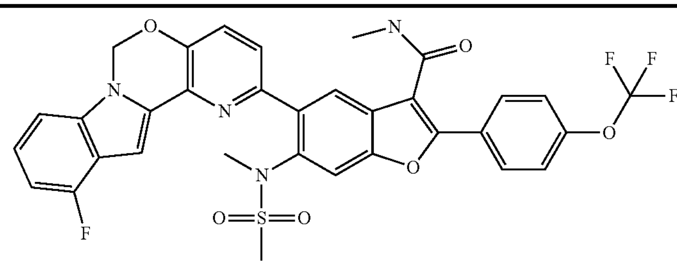 | $^1$H-NMR (CDCl$_3$, 400 MHz) δ 8.03 (d, J = 8.8 Hz, 2H), 7.98 (s, 1H), 7.67 (s, 1H), 7.49 (s, 2H), 7.35 (d, J = 8.0 Hz, 2H), 7.18~7.24 (m, 2H), 7.11 (d, J = 8.0 Hz, 1H), 6.85 (t, J = 9.2 Hz, 1H), 6.08 (br s., 1H), 6.00 (s, 2H), 3.36 (s, 3H), 3.01 (d, J = 4.8 Hz, 3H), 2.75 (s, 3H). | 681 |
| 34 | 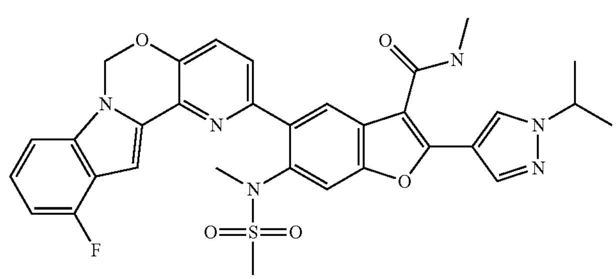 [SMILES: CNC(=O)c1c(-c2cnn(C(C)C)c2)oc2cc(N(C)S(C)(=O)=O)c(-c3ccc4c(n3)-c3cc5c(F)cccc5n3CO4)cc12] | $^1$H-NMR (CDCl$_3$, 400 MHz) δ 8.50 (s, 1H), 8.14 (s, 1H), 7.90 (s, 1H), 7.62 (s, 1H), 7.48~7.54 (m, 2H), 7.17~7.26 (m, 2H), 7.12 (d, J = 8.4 Hz, 1H), 6.80~6.91 (m, 1H), 6.18 (br s., 1H), 6.00 (s, 2H), 4.55~4.62 (m, 1H), 3.35 (s, 3H), 3.05 (d, J = 4.8 Hz, 3H), 2.80 (s, 3H), 1.59 (d, J = 6.4 Hz, 6H). | 629 |
| 35 | 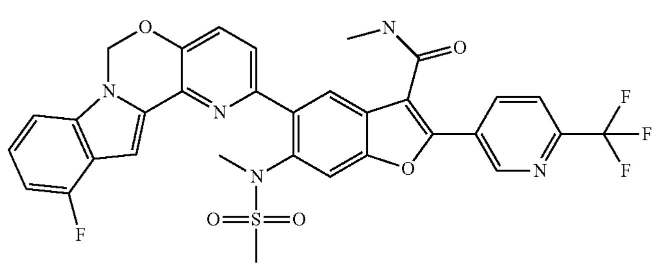 [SMILES: CNC(=O)c1c(-c2ccc(C(F)(F)F)nc2)oc2cc(N(C)S(C)(=O)=O)c(-c3ccc4c(n3)-c3cc5c(F)cccc5n3CO4)cc12] | $^1$H-NMR (CDCl$_3$, 400 MHz) δ 9.32 (s, 1H), 8.66 (d, J = 8.4 Hz, 1H), 7.97 (s, 1H), 7.80 (d, J = 8.4 Hz, 1H), 7.75 (s, 1H), 7.51 (s, 2H), 7.20~7.24 (m, 2H), 7.12 (d, J = 8.0 Hz, 1H), 6.85 (t, J = 8.4 Hz, 1H), 6.11 (d, J = 4.8 Hz, 1H), 6.01 (s, 2H), 3.35 (s, 3H), 3.06 (d, J = 4.8 Hz, 3H), 2.80 (s, 3H). | 666 |

Example 36

5-(11-fluoro-6H-pyrido[2',3':5,6][1,3]oxazino[3,4-a]indol-2-yl)-2-(1H-imidazol-1-yl)-N-methyl-6-(N-methylmethylsulfonamido)benzofuran-3-carboxamide

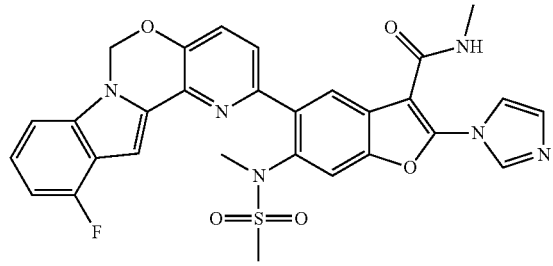 [SMILES: CNC(=O)c1c(-n2ccnc2)oc2cc(N(C)S(C)(=O)=O)c(-c3ccc4c(n3)-c3cc5c(F)cccc5n3CO4)cc12]

Step 1 - 5-bromo-2-(1H-imidazol-1-yl)-N-methyl-6-(N-methylmethylsulfonamido)benzofuran-3-carboxamide

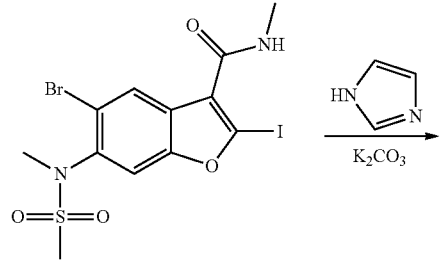

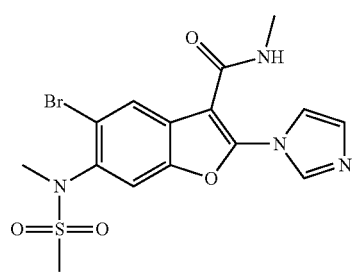

To a degassed solution of 5-bromo-2-iodo-N-methyl-6-(N-methylmethylsulfonamido)benzofuran-3-carboxamide (100 mg, 0.21 mmol) and $K_2CO_3$ (43 mg, 0.31 mmol) in DMF (1 mL) was added 1H-imidazole (14 mg, 0.21 mmol) under $N_2$ at 0° C. The mixture was heated at 60° C. for 10 hours. The reaction mixture was concentrated and it was extracted with EtOAc. The residue was washed with $H_2O$, brine, dried over $Na_2SO_4$. After being concentrated, the crude product was purified by column (PE:EA=1:1) to give of 5-bromo-2-(1H-imidazol-1-yl)-N-methyl-6-(N-methylmethylsulfonamido)benzofuran-3-carboxamide (72 mg, yield: 83%). $^1$H-NMR (DMSO-$d_6$, 400 MHz) δ 8.40 (d, J=4.4 Hz, 1H), 8.36 (s, 1H), 8.10 (s, 2H), 7.80 (s, 1H), 7.19 (s, 1H), 3.21 (s, 3H), 3.20 (s, 3H), 2.81 (d, J=4.4 Hz, 3H). MS (M+H)$^+$: 427/429.

Step 2 - 2-(1H-imidazol-1-yl)-N-methyl-6-(N-methylmethylsulfonamido)-5-(4,4,5,5-tetramethyl-1,3,2-dioxaborolan-2-yl)benzofuran-3-carboxamide

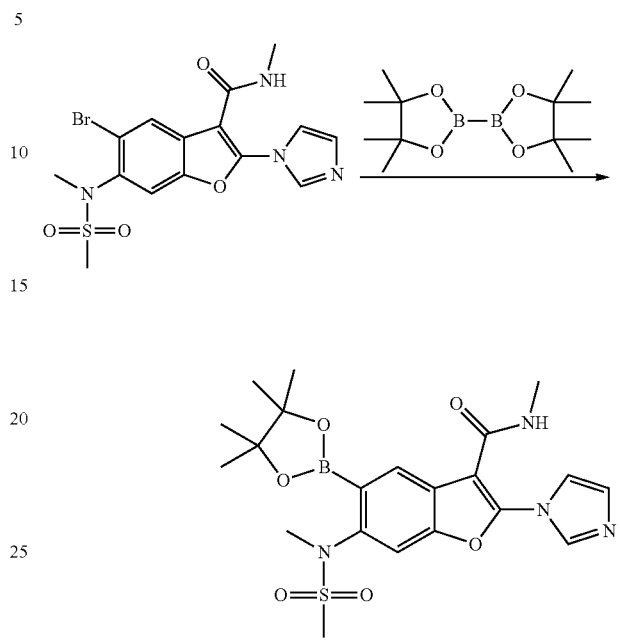

To a degassed solution of 5-bromo-2-(1H-imidazol-1-yl)-N-methyl-6-(N-methylmethylsulfonamido)benzofuran-3-carboxamide (60 mg, 0.12 mmol) and 4,4,5,5-tetramethyl-2-(4,4,5,5,-tetramethyl-1,3,2-dioxaborolan-2-yl)-1,3,2-dioxaborolane (220 mg, 0.60 mmol) in 1,4-dioxane (2 mL) were added Pd(dppf)Cl$_2$ (10 mg) and KOAc (40 mg, 0.35 mmol) under $N_2$. The mixture was heated at a pre-heated oil-bath at 130° C. for 3 h. The reaction mixture was concentrated in vacuo and it was extracted with EtOAc. The residue was washed with $H_2O$, brine, dried over $Na_2SO_4$. After concentrated, the crude product was purified by prep-TLC (PE:EA=1:1) to give of 2-(1H-imidazol-1-yl)-N-methyl-6-(N-methylmethylsulfonamido)-5-(4,4,5,5-tetramethyl-1,3,2-dioxaborolan-2-yl)benzofuran-3-carboxamide (30 mg, yield: 53%). $^1$H-NMR (DMSO-$d_6$, 400 MHz) δ 8.18 (s, 1H), 7.69 (s, 1H), 7.46 (d, J=6.4 Hz, 2H), 7.21 (s, 1H), 5.92 (s, 1H), 3.36 (s, 3H), 3.04 (d, J=4.48 Hz, 3H), 2.95 (s, 3H), 1.37 (s, 12H). MS (M+H)$^+$: 475.

Step 3 - Synthesis of 5-(11-fluoro-6H-pyrido[2',3':5,6][1,3]oxazino[3,4-a]indol-2-yl)-2-(1H-imidazol-1-yl)-N-methyl-6-(N-methylmethylsulfonamido)benzofuran-3-carboxamide

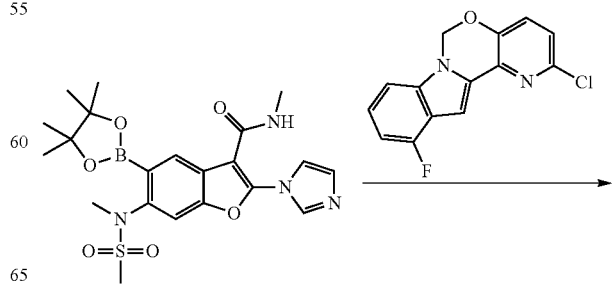

-continued

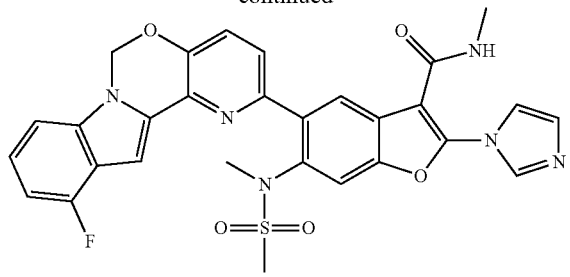

To a solution of 2-(1H-imidazol-1-yl)-N-methyl-6-(N-methylmethylsulfonamido)-5-(4,4,5,5-tetramethyl-1,3,2-dioxaborolan-2-yl)benzofuran-3-carboxamide (60 mg, 0.13 mmol), 2-chloro-11-fluoro-6H-pyrido[2',3':5,6][1,3]oxazino[3,4-a]indole (42 mg, 0.15 mmol) and K₂CO₃ (26 mg, 0.19 mmol) in 1,4-dioxane (1 mL) and water (0.01 mL) were added X-Phos (10 mg) and Pd₂(dba)₃ (10 mg) under nitrogen.

The mixture was heated at 110° C. for 3 hours and filtered through the celite pad. The filtrate was extracted with EtOAc and the combined organic phase was washed with brine, dried over Na₂SO₄ and concentrated in vacuo. The crude product was purified by prep-HPLC to give 5-(11-fluoro-6H-pyrido[2',3':5,6][1,3]oxazino[3,4-a]indol-2-yl)-2-(1H-imidazol-1-yl)-N-methyl-6-(N-methylmethylsulfonamido)benzofuran-3-carboxamide (30 mg, yield: 40%). ¹H-NMR (400 MHz, CDCl₃) δ 8.36 (s, 1H), 8.03 (s, 1H), 7.73 (s, 1H), 7.68 (s, 1H), 7.52 (s, 2H), 7.20~7.25 (m, 3H), 7.12 (d, J=8.4 Hz, 1H), 6.84~6.88 (m, 1H), 6.02 (s, 2H), 5.93 (d, J=4.8 Hz, 1H), 3.35 (s, 3H), 3.02 (d, J=4.8 Hz, 3H), 2.78 (s, 3H). MS (M+H)⁺: 587.

Examples 37-41

Examples 37~41, depicted in the table below, were prepared in accordance with the method described in Example 39.

| Example | Structure | NMR | MS (M + H)⁺ |
|---|---|---|---|
| 37 | 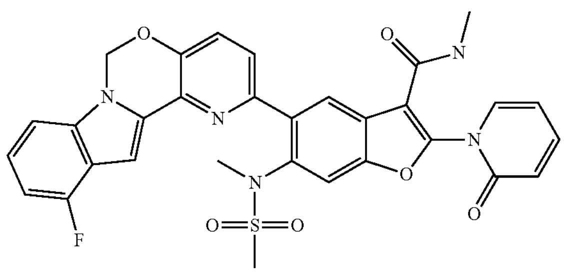 [SMILES: CNC(=O)c1c(-n2ccccc2=O)oc2cc(N(C)S(C)(=O)=O)c(-c3ccc4c(n3)-c3cc5c(F)cccc5n3CO4)cc12] | ¹H-NMR (CDCl₃, 400 MHz) δ 8.17 (s, 1H), 7.71 (d, J = 4.8 Hz, 1H), 7.66 (s, 1H), 7.48~7.58 (m, 3H), 7.39~7.41 (m, 1H), 7.21~7.25 (m, 2H), 7.11 (d, J = 8.0 Hz, 1H), 6.82~6.86 (m, 1H), 6.75 (d, J = 8.8 Hz, 1H), 6.45 (t, J = 6.4 Hz, 1H), 6.00 (s, 2H), 3.38 (s, 3H), 2.90 (d, J = 4.8 Hz, 3H), 2.68 (s, 3H). | 614 |
| 38 | 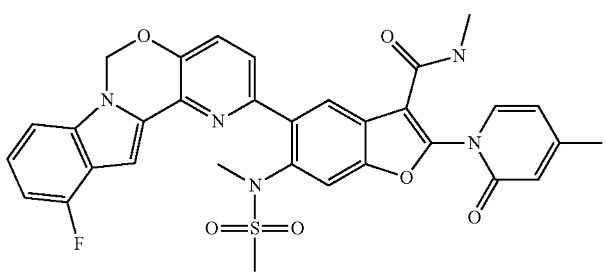 [SMILES: CNC(=O)c1c(-n2ccc(C)cc2=O)oc2cc(N(C)S(C)(=O)=O)c(-c3ccc4c(n3)-c3cc5c(F)cccc5n3CO4)cc12] | ¹H-NMR (CDCl₃, 400 MHz) δ 8.18 (s, 1H), 7.82 (d, J = 4.8 Hz, 1H), 7.66 (s, 1H), 7.48 (s, 2H), 7.28 (d, J = 6.8 Hz, 1H), 7.19~7.22 (m, 2H), 7.11 (d, J = 8.4 Hz, 1H), 6.82~6.87 (m, 1H), 6.54 (s, 1H), 6.29 (d, J = 7.2 Hz, 1H), 6.00 (s, 2H), 3.38 (s, 3H), 2.90 (d, J = 4.8 Hz, 3H), 2.67 (s, 3H), 2.32 (s, 3H). | 628 |
| 39 | 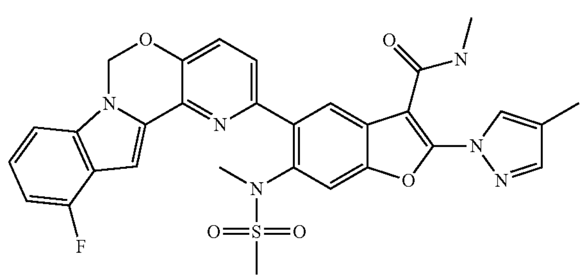 [SMILES: CNC(=O)c1c(-n2cc(C)cn2)oc2cc(N(C)S(C)(=O)=O)c(-c3ccc4c(n3)-c3cc5c(F)cccc5n3CO4)cc12] | ¹H-NMR (CDCl₃, 400 MHz) δ 8.69 (s, 1H), 8.03 (s, 1H), 7.72 (s, 1H), 7.65 (s, 1H), 7.47~7.54 (m, 2H), 7.23 (s, 1H), 7.12 (d, J = 8.8 Hz, 1H), 6.86 (t, J = 4.4 Hz,1H), 6.01 (s, 2H), 3.43 (s, 3H), 3.01 (d, J = 4.0 Hz, 3H), 2.66 (s, 3H), 2.26 (s, 3H). | 601 |
| 40 | 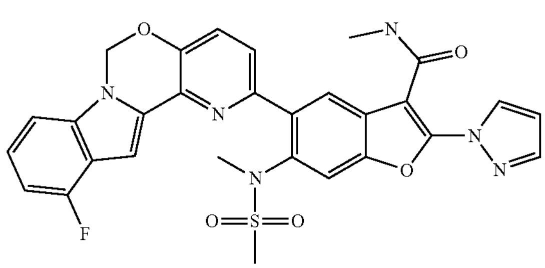 [SMILES: CNC(=O)c1c(-n2cccn2)oc2cc(N(C)S(C)(=O)=O)c(-c3ccc4c(n3)-c3cc5c(F)cccc5n3CO4)cc12] | ¹H-NMR (CDCl₃, 400 MHz) δ 8.69 (s, 1H), 8.27 (s, 1H), 7.92 (s, 1H), 7.67 (s, 1H), 7.54~7.46 (m, 2H), 7.22 (s, 2H), 7.13 (d, J = 8.4 Hz, 1H), 6.88 (t, J = 9.6, 8.4 Hz, 1H), 6.66 (s, 1H), 6.01 (s, 2H), 3.43 (s, 3H), 3.02 (d, J = 4.8 Hz, 3H), 2.66 (s, 1H). | 587 |

| Example | Structure | NMR | MS (M + H)+ |
|---|---|---|---|
| 41 | 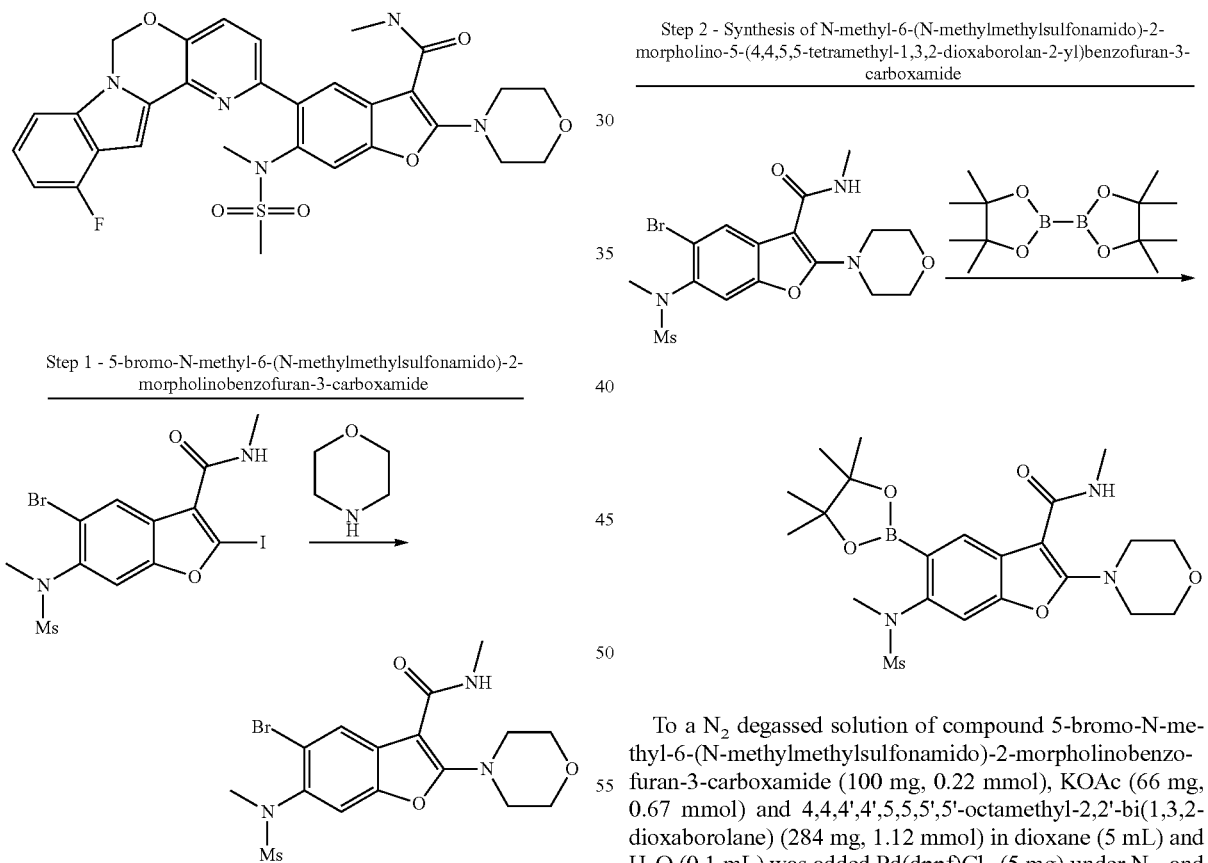 | ¹H-NMR (CDCl₃, 400 MHz) δ 9.36 (d, J = 4.0 Hz, 1H), 8.75 (s, 1H), 8.57 (s, 1H), 7.62 (s, 1H), 7.44 (m, 2H), 7.15 (d, J = 5.2 Hz, 2H), 7.05 (d, J = 8.4 Hz, 1H), 6.78 (m, 1H), 5.94 (s, 1H), 3.34 (s, 3H), 2.96 (d, J = 4.4 Hz, 3H), 2.61 (s, 3H), 2.53 (s, 3H). | 602 |

Example 42

5-(11-fluoro-6H-pyrido[2',3':5,6][1,3]oxazino[3,4-a]indol-2-yl)-N-methyl-6-(N-methylmethylsulfonamido)-2-morpholinobenzofuran-3-carboxamide

Step 1 - 5-bromo-N-methyl-6-(N-methylmethylsulfonamido)-2-morpholinobenzofuran-3-carboxamide To a suspension of compound 5-bromo-2-iodo-N-methyl-6-(N-methylmethylsulfonamido)benzofuran-3-carboxamide (50 mg, 0.1 mmol) in pyridine (3 mL) was added morpholine (18 mg, 0.2 mol) under N₂, and then the mixture was stirred at 60° C. for 3 hours. After concentration in vacuo, DCM was added and the resulting residue was washed with 10% HCl (a.q., 3 mL) and dried over Na₂SO₄. After concentration, the residue was purified by prep-TLC (DCM:MeOH=20:1) to give the product of 5-bromo-N-methyl-6-(N-methylmethylsulfonamido)-2-morpholinobenzofuran-3-carboxamide (20 mg, yield: 44%). ¹H-NMR (CDCl₃, 400 MHz) δ 8.05 (s, 1H), 7.47 (s, 1H), 6.48 (s, 1H), 3.86 (t, J=4.4 Hz, 4H), 3.46 (t, J=6.4 Hz, 4H), 3.28 (s, 3H), 3.04 (s, 3H), 2.99 (d, J=4.8 Hz, 3H). MS (M+H)⁺: 446/448.

Step 2 - Synthesis of N-methyl-6-(N-methylmethylsulfonamido)-2-morpholino-5-(4,4,5,5-tetramethyl-1,3,2-dioxaborolan-2-yl)benzofuran-3-carboxamide To a N₂ degassed solution of compound 5-bromo-N-methyl-6-(N-methylmethylsulfonamido)-2-morpholinobenzofuran-3-carboxamide (100 mg, 0.22 mmol), KOAc (66 mg, 0.67 mmol) and 4,4,4',4',5,5,5',5'-octamethyl-2,2'-bi(1,3,2-dioxaborolane) (284 mg, 1.12 mmol) in dioxane (5 mL) and H₂O (0.1 mL) was added Pd(dppf)Cl₂ (5 mg) under N₂, and the mixture was stirred at 130° C. for 3 hours. After concentration, the residue was purified by prep-TLC (DCM:MeOH=20:1) to give the product of compound N-methyl-6-(N-methylmethylsulfonamido)-2-morpholino-5-(4,4,5,5-tetramethyl-1,3,2-dioxaborolan-2-yl)benzofuran-3-carboxamide (50 mg, yield: 45%). ¹H-NMR (CDCl₃, 400 MHz) δ 8.05 (s, 1H), 7.47 (s, 1H), 6.48 (s, 1H), 3.86 (t, J=4.4 Hz, 4H), 3.46 (t, J=6.4 Hz, 4H), 3.28 (s, 3H), 3.04 (s, 3H), 2.99 (d, J=4.8 Hz, 3H), 1.34 (s, 12H). MS (M+H)⁺: 494.

Step 3 - Synthesis of 5-(11-fluoro-6H-pyrido[2',3':5,6][1,3]oxazino[3,4-a]indol-2-yl)-N-methyl-6-(N-methylmethylsulfonamido)-2-morpholinobenzofuran-3-carboxamide

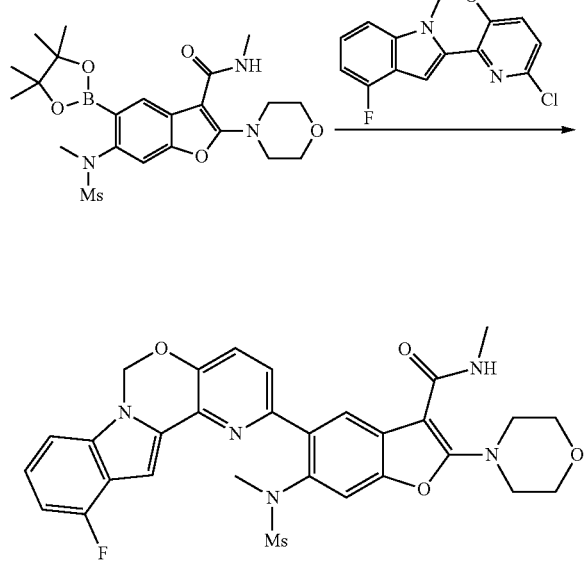

To a degassed solution of N-methyl-6-(N-methylmethylsulfonamido)-2-morpholino-5-(4,4,5,5-tetramethyl-1,3,2-dioxaborolan-2-yl)benzofuran-3-carboxamide (80 mg, 0.16 mmol), 2-chloro-11-fluoro-6H-pyrido[2',3':5,6][1,3]oxazino[3,4-a]indole (47 mg, 0.17 mmol), Na$_2$CO$_3$ (34 mg, 0.32 mmol) in dioxane (1.5 mL) and H$_2$O (0.1 mL) was added Pd(dppf)Cl$_2$ (3 mg) under N$_2$. Then the mixture was stirred at 100° C. for 2 hours. The reaction mixture was cooled to RT and filtered. The filtrate was washed with H$_2$O and dried over Na$_2$SO$_4$. After concentration, the residue was purified by prep-HPLC to give the product of 5-(11-fluoro-6H-pyrido[2',3':5,6][1,3]oxazino[3,4-a]indol-2-yl)-N-methyl-6-(N-methylmethylsulfonamido)-2-morpholinobenzofuran-3-carboxamide (10 mg, yield: 10%). $^1$H-NMR (CDCl$_3$, 400 MHz) δ 8.01 (s, 1H), 7.45~7.47 (m, 3H), 7.18~7.21 (m, 2H), 7.12 (d, J=8.0 Hz, 1H), 6.82~6.87 (m, 1H), 6.64 (s, 1H), 5.99 (s, 2H), 3.89 (t, J=4.4 Hz, 4H), 3.51 (t, J=6.4 Hz, 4H), 3.36 (s, 3H), 3.01 (d, J=4.8 Hz, 3H), 2.68 (s, 3H). MS (M+H)$^+$: 606.

Example 43

Example 43 depicted in the table below, was prepared in accordance with the method described in Example 42.

Example 44

2-(cyclopent-1-en-1-yl)-N-methyl-6-(N-methylmethylsulfonamido)-5-(6H-pyrido[2',3':5,6][1,3]oxazino[3,4-a]indol-2-yl)benzofuran-3-carboxamide

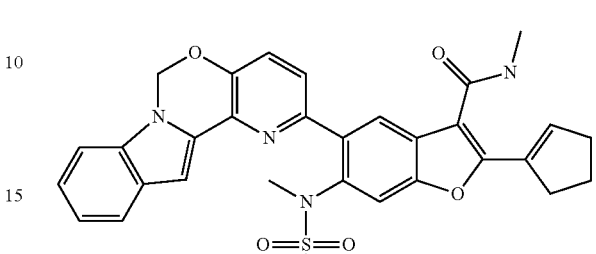

Step 1 - Synthesis of ethyl 6-amino-5-bromo-2-(1-hydroxycyclopentyl)benzofuran-3-carboxylate

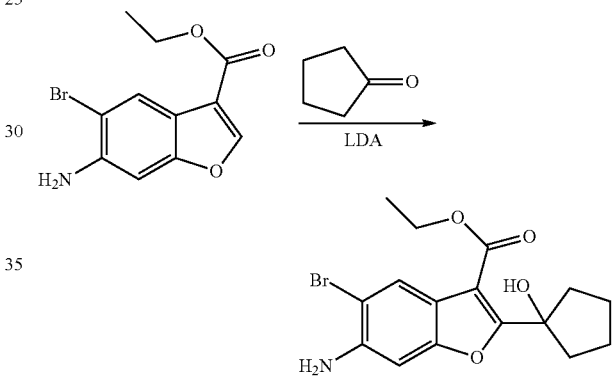

To a solution of LDA (6.32 g, 59.0 mmol) in THF (60 mL) was added dropwise ethyl 6-amino-5-bromobenzofuran-3-carboxylate (5 g, 17.6 mmol) at −78° C. under N$_2$. After the mixture was stirred for 1 hour, cyclopentanone (4.44 g, 52.8 mmol) in THF (40 mL) was added dropwise at −78° C. After the mixture was stirred for 1 h, NH$_4$Cl (a.q.) was added, then the mixture was extracted with EtOAc (100 mL*3) and dried over Na$_2$SO$_4$ After concentration, the residue was purified by column chromatography (PE:EtOAc=10:1) to give the product of ethyl 6-amino-5-bromo-2-(1-hydroxycyclopentyl)

| Compound ID | Structure | NMR | MS (M + H)$^+$ |
|---|---|---|---|
| 43 | | $^1$H-NMR (CDCl$_3$, 400 MHz) δ 8.11 (s, 1H), 7.62 (s, 1H), 7.49 (s, 2H), 7.44 (d, J = 4.4 Hz, 1H), 7.20~7.25 (m, 2H), 7.13 (d, J = 8.0 Hz, 1H), 6.86 (dd, J = 8.0, 9.6 Hz, 1H), 6.01 (s, 2H), 4.70 (t, J = 8.0 Hz, 2H), 4.28 (t, J = 8.0 Hz, 2H), 3.39 (s, 3H), 2.98 (d, J = 4.8 Hz, 3H), 2.69 (s, 3H). | 606 | benzofuran-3-carboxylate (2.9 g, yield: 44%). $^1$H-NMR (CDCl$_3$, 400 MHz) δ 7.94 (s, 1H), 6.86 (s, 1H), 6.07 (s, 1H), 4.46 (q, J=7.2 Hz, 2H), 4.20 (s, 1H), 2.12~2.17 (m, 4H), 1.99 (t, J=5.6 Hz, 2H), 1.79 (t, J=3.2 Hz, 2H), 1.50 (t, J=7.2 Hz, 3H). MS (M+H)$^+$: 368/370.

Step 2 - Synthesis of ethyl 6-amino-5-bromo-2-(cyclopent-1-en-1-yl))benzofuran-3-carboxylate

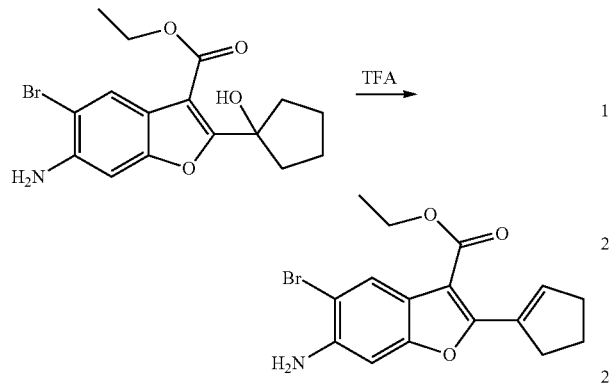

TFA (1.5 mL) was added into a solution of ethyl 6-amino-5-bromo-2-(1-hydroxycyclopentyl)benzofuran-3-carboxylate (2.9 g, 7.89 mmol) in DCM (30 mL), then the mixture was stirred at 25° C. for 12 hours. The reaction mixture was poured into ice water, adjusted to pH=7 with NaHCO$_3$ (a.q.), then the residue was extracted with DCM (50 mL*3), dried over Na$_2$SO$_4$, and concentrated to give the product of ethyl 6-amino-5-bromo-2-(cyclopent-1-en-1-yl)benzofuran-3-carboxylate (2.6 g, yield: 94%). $^1$H-NMR (CDCl$_3$, 400 MHz) δ 7.99 (s, 1H), 7.11 (t, J=7.2 Hz, 1H), 6.83 (s, 1H), 4.43 (q, J=7.2 Hz, 2H), 2.86~2.91 (m, 2H), 2.59~2.63 (m, 2H), 2.01 (t, J=8.0 Hz, 2H), 1.46 (t, J=3.2 Hz, 3H). MS (M+H)$^+$: 350/352.

Step 3 - Synthesis of ethyl 5-bromo-2-(cyclopent-1-en-1-yl)-6-methylsulfonamido)benzofuran-3-carboxylate

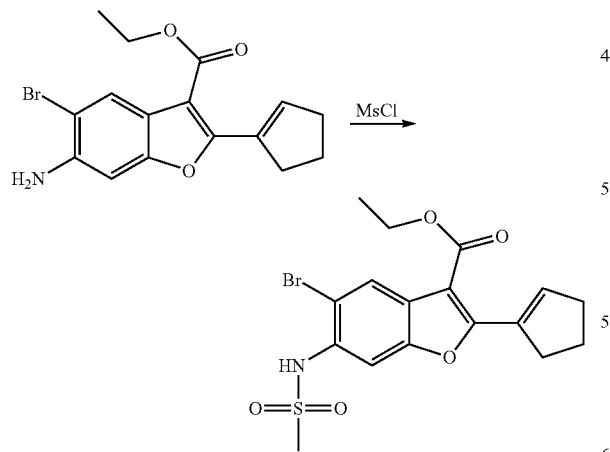

To a solution of ethyl 6-amino-5-bromo-2-(cyclopent-1-en-1-yl)benzofuran-3-carboxylate (3.63 g, 10.37 mmol) and pyridine (2.46 g, 31.1 mmol) in DCM (30 mL) was added dropwise methanesulfonyl chloride (2.37 g, 20.7 mmol) at 0° C., then the mixture stirred at 25° C. overnight. 10% HCl(a.q.) was added, then the mixture was extracted with DCM (50 mL*3), dried over Na$_2$SO$_4$, and concentrated to give the product of ethyl 5-bromo-2-(cyclopent-1-en-1-yl)-6-(methylsulfonamido)benzofuran-3-carboxylate (4.3 g, yield: 96%). $^1$H-NMR (CDCl$_3$, 400 MHz) δ 8.19 (s, 1H), 7.80 (s, 1H), 7.22 (t, J=2.0 Hz, 1H), 6.84 (s, 1H), 4.45 (q, J=7.2 Hz, 2H), 2.99 (s, 3H), 2.89~2.94 (m, 2H), 2.62~2.67 (m, 2H), 2.06 (t, J=7.6 Hz, 2H), 1.47 (t, J=7.2 Hz, 3H). MS (M+H)$^+$: 428/430.

Step 4 - Synthesis of ethyl 5-bromo-2-(cyclopent-1-en-1-yl)-6-(N-methylmethylsulfonamido)benzofuran-3-carboxylate

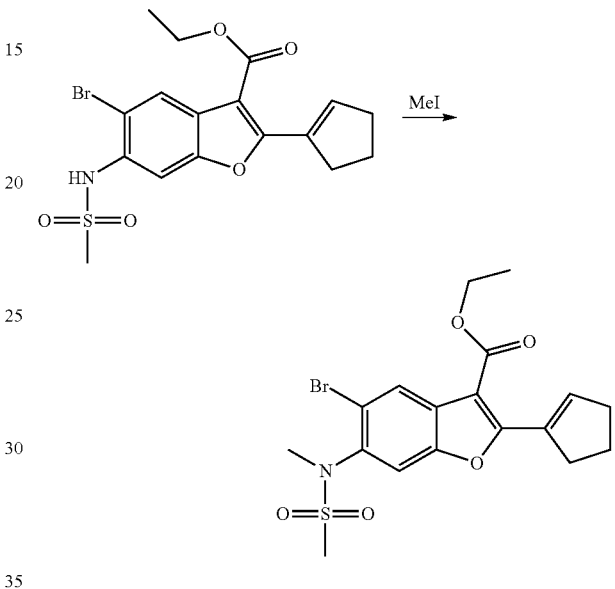

To a solution of ethyl 5-bromo-2-(cyclopent-1-en-1-yl)-6-(methylsulfonamido)benzofuran-3-carboxylate (5.3 g, 12.37 mmol), K$_2$CO$_3$ (5.13 g, 37.12 mmol) in DMF (50 mL) was added MeI (30 g, 23.5 mmol), then the mixture was stirred at 80° C. After 3 hours, the solvent was removed by vacuum, the mixture was washed with H$_2$O (100 mL) and extracted with DCM (100 mL*3), dried over Na$_2$SO$_4$ and concentrated to give the desired product of ethyl 5-bromo-2-(cyclopent-1-en-1-yl)-6-(N-methylmethylsulfonamido)benzofuran-3-carboxylate (5 g, yield: 91%). $^1$H-NMR (CDCl$_3$, 400 MHz) δ 8.22 (s, 1H), 7.61 (s, 1H), 7.23 (t, J=2.0 Hz, 1H), 4.42 (q, J=7.2 Hz, 2H), 3.31 (s, 3H), 3.06 (s, 3H), 2.63~2.64 (m, 2H), 1.99~2.03 (m, 2H), 2.01 (t, J=7.6 Hz, 2H), 1.46 (t, J=7.2 Hz, 3H). MS (M+H)$^+$: 442/444.

Step 5 - 5-bromo-2-(cyclopent-1-en-1-yl)-6-(N-methylmethylsulfonamido)benzofuran-3-carboxylic acid

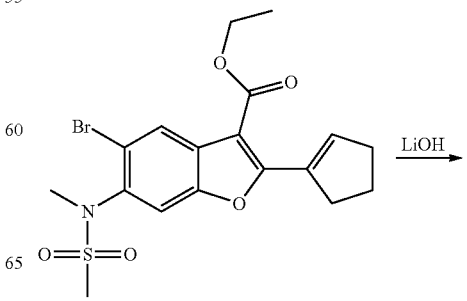

-continued

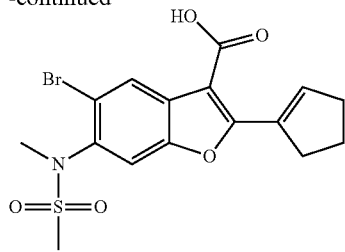

To a solution of ethyl 5-bromo-2-(cyclopent-1-en-1-yl)-6-(N-methylmethylsulfonamido)benzofuran-3-carboxylate (4.4 g, 9.94 mmol) in 1,4-Dioxane (40 mL) and H$_2$O (4 mL) was added LiOH (1.2 g, 49.72 mmol), then the mixture was stirred at 110° C. After 3 hours, the solvent was removed by vacuum, 10% HCl (aq) was added, and the mixture was adjusted to pH=4-5. Then the residue was dissolved in EtOAc (200 mL), dried over Na$_2$SO$_4$ and concentrated to give the desired product of 5-bromo-2-(cyclopent-1-en-1-yl)-6-(N-methylmethylsulfonamido)benzofuran-3-carboxylic acid (3.5 g, yield: 84%). $^1$H-NMR (CDCl$_3$, 400 MHz) δ 8.35 (s, 1H), 7.66 (s, 1H), 7.32 (t, J=2.0 Hz, 1H), 3.36 (s, 3H), 3.09 (s, 3H), 2.9~02.95 (m, 2H), 2.67~2.71 (m, 2H), 2.08 (t, J=8.0 Hz, 2H). MS (M+H)$^+$: 414/416.

Step 6 - Synthesis of 5-bromo-2-(cyclopent-1-en-1-yl)-N-methyl-6-(N-methylmethylsulfonamido)benzofuran-3-carboxamide

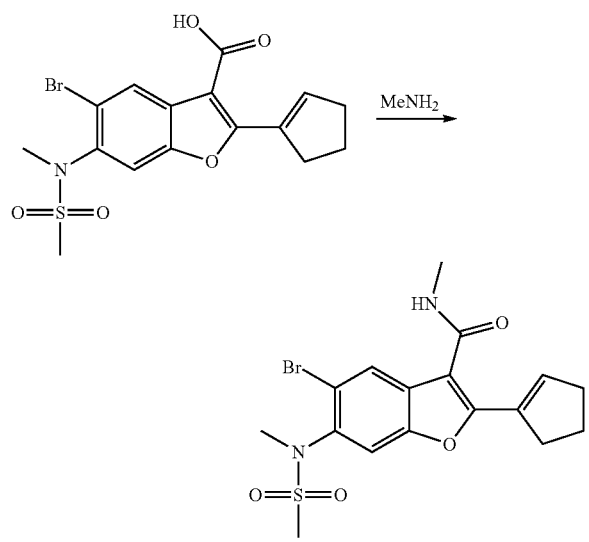

A solution of 5-bromo-2-(cyclopent-1-en-1-yl)-6-(N-methylmethylsulfonamido)benzofuran-3-carboxylic acid (3.5 g, 7.70 mmol), HOBT (1.6 g, 11.55 mmol) and EDCI (2.2 g, 11.55 mmol) in dry DMF (40 mL) was stirred at 25° C. After 2 hours, Et$_3$N (2.4 g, 23.11 mmol) and MeNH$_2$ (1.6 g, 23.11 mmol) were added to the mixture and then stirred overnight. The solvent was removed by vacuum, the mixture was washed with H$_2$O (50 mL) and extracted with EtOAc (50 mL*3), and dried over Na$_2$SO$_4$. After concentration, the residue was purified by column chromatography (DCM) to give the product of 5-bromo-2-(cyclopent-1-en-1-yl)-N-methyl-6-(N-methylmethylsulfonamido)benzofuran-3-carboxamide (2 g, yield: 56%). $^1$H-NMR (CDCl$_3$, 400 MHz) δ 8.00 (s, 1H), 7.59 (s, 1H), 6.70 (t, J=3.2 Hz, 1H), 5.95 (s, 1H), 3.31 (s, 3H), 3.30 (s, 3H), 3.06 (s, 3H), 2.76~2.81 (m, 2H), 2.58~2.62 (m, 2H), 2.07 (t, J=7.6 Hz, 2H). MS (M+H)$^+$: 427/429.

Step 7 - Synthesis of 2-(cyclopent-1-en-1-yl)-N-methyl-6-(N-methylmethylsulfonamido)-5-(4,4,5,5-tetramethyl-1,3,2-dioxaborolan-2-yl)benzofuran-3-carboxamide

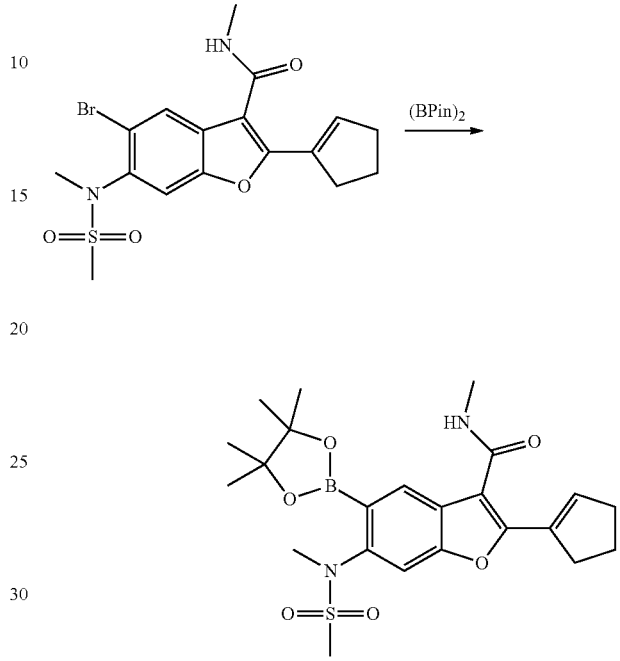

To a degassed solution of 5-bromo-2-(cyclopent-1-en-1-yl)-N-methyl-6-(N-methylmethylsulfonamido)benzofuran-3-carboxamide (1 g, 2.34 mmol), bis(pinacolato)diboron (3 g, 11.70 mmol), CH$_3$COOK (689 mg, 7.02 mmol) in 1,4-Dioxane (10 mL) and H$_2$O (1 mL) was added Pd(dppf)Cl$_2$ (10 mg), then the mixture was stirred at 130° C. After 3 hours, the solvent was removed by vacuum, and the mixture was washed with H$_2$O (60 mL), extracted with DCM (50 mL*3), and dried over Na$_2$SO$_4$. After concentration, the residue was purified by column chromatography (PE:EtOAc=2:1) to give the product of 2-(cyclopent-1-en-1-yl)-N-methyl-6-(N-methylmethylsulfonamido)-5-(4,4,5,5-tetramethyl-1,3,2-dioxaborolan-2-yl)benzofuran-3-carboxamide (400 mg, yield: 36%). $^1$H-NMR (CDCl$_3$, 400 MHz) δ 8.06 (s, 1H), 7.45 (s, 1H), 6.66 (s, 1H), 6.62 (s, 1H), 3.32 (s, 3H), 3.02 (s, 3H), 2.92 (s, 3H), 2.76~2.79 (m, 2H), 2.53~2.57 (m, 2H), 2.01 (t, J=7.6 Hz, 2H), 1.34 (s, 12H). MS (M+H)$^+$: 475.

Step 8 - Synthesis of 2-(cyclopent-1-en-1-yl)-N-methyl-6-(N-methylmethylsulfonamido)-5-(6H-pyrido[2′,3′:5,6][1,3]oxazino[3,4-a]indol-2-yl)benzofuran-3-carboxamide

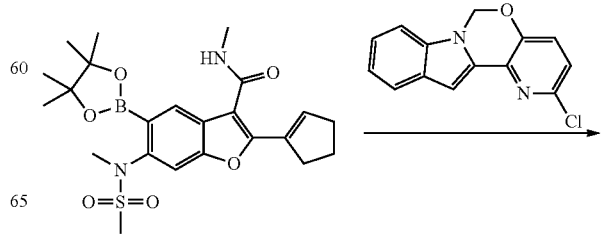

-continued

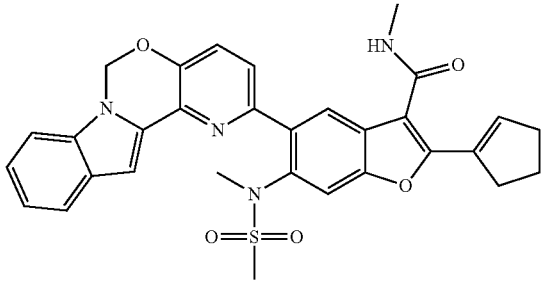

To a degassed solution of 2-(cyclopent-1-en-1-yl)-N-methyl-6-(N-methylmethylsulfonamido)-5-(4,4,5,5-tetramethyl-1,3,2-dioxaborolan-2-yl)benzofuran-3-carboxamide (110 mg, 0.23 mmol), 2-chloro-6H-pyrido[2',3':5,6][1,3]oxazino[3,4-a]indole (70 mg, 0.27 mmol), $K_3PO_4$ (123 mg, 0.46 mmol) in 1,4-Dioxane (5 mL) and $H_2O$ (0.5 ml) was added $Pd(dba)_3$ (5 mg) and X-Phos (5 mg) under $N_2$, then the mixture was stirred at 110° C. for 2 hours. The reaction mixture was cooled to RT and filtered. The filtrate was washed with $H_2O$, brine, extract with DCM, and dried over $Na_2SO_4$. After concentration, the residue was purified by prep-HPLC to give the product of 2-(cyclopent-1-en-1-yl)-N-methyl-6-(N-methylmethylsulfonamido)-5-(6H-pyrido[2',3':5,6][1,3]oxazino[3,4-a]indol-2-yl)benzofuran-3-carboxamide (30 mg, yield: 23%). $^1$H-NMR (CDCl$_3$, 400 MHz) δ 7.88 (s, 1H), 7.69 (d, J=7.6 Hz, 1H), 7.56 (s, 1H), 7.47 (s, 2H), 7.27~7.33 (m, 2H), 7.14~7.20 (m, 2H), 6.74 (s, 1H), 6.10 (s, 1H), 5.99 (s, 2H), 3.32 (s, 3H), 3.01 (d, J=4.8 Hz, 3H), 2.83 (d, J=6.8 Hz, 2H), 2.73 (s, 3H), 2.62 (t, J=6.8 Hz, 2H), 2.00~2.08 (m, 2H). MS (M+H)$^+$: 569.

Examples 45-47

Examples 45~47, depicted in the table below, were prepared in accordance with the method described in Example 47.

| Example | Structure | NMR | MS (M + H)$^+$ |
|---|---|---|---|
| 45 | 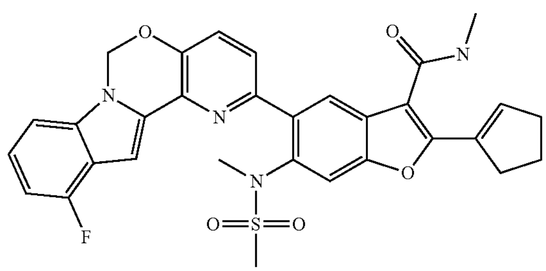 [SMILES: CNC(=O)c1c(C2=CCCC2)oc2cc(N(C)S(C)(=O)=O)c(-c3ccc4c(n3)-c3cc5c(F)cccc5n3CO4)cc12] | $^1$H-NMR (CDCl$_3$, 400 MHz) δ 7.91 (s, 1H), 7.58 (s, 1H), 7.50 (s, 2H), 7.19~7.24 (m, 1H), 7.12 (d, J = 8.0 Hz, 1H), 6.87 (t, J = 7.6 Hz, 1H), 6.76 (s, 1H), 6.10 (t, J = 3.6 Hz, 1H), 6.00 (s, 2H), 3.35 (s, 3H), 3.04 (d, J = 4.8 Hz, 3H), 2.83~2.88 (m, 2H), 2.76 (s, 3H), 2.60~2.64 (m, 2H), 2.02~2.10 (m, 2H). | 587 |
| 46 | 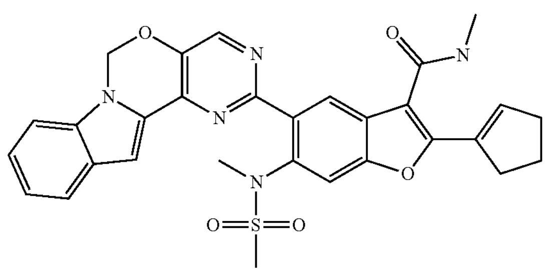 [SMILES: CNC(=O)c1c(C2=CCCC2)oc2cc(N(C)S(C)(=O)=O)c(-c3ncc4c(n3)-c3cc5ccccc5n3CO4)cc12] | $^1$H-NMR (CDCl$_3$, 400 MHz) δ 8.65 (s, 1H), 8.18 (s, 1H), 7.75 (d, J = 8.8 Hz, 1H), 7.61 (s, 1H), 7.37~7.42 (m, 2H), 7.33~7.36 (m, 2H), 6.80 (s, 1H), 6.18~6.21 (m, 1H), 6.07 (s, 2H), 3.48 (s, 3H), 3.03 (d, J = 4.8 Hz, 3H), 2.80~2.87 (m, 2H), 2.64 (s, 3H), 2.58 (t, J = 4.8 Hz, 2H), 1.98~2.01 (m, 2H). | 570 |
| 47 | 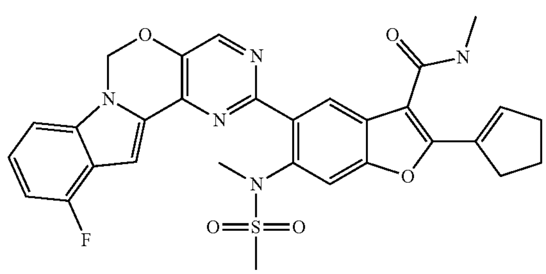 [SMILES: CNC(=O)c1c(C2=CCCC2)oc2cc(N(C)S(C)(=O)=O)c(-c3ncc4c(n3)-c3cc5c(F)cccc5n3CO4)cc12] | $^1$H-NMR (CDCl$_3$, 400 MHz) δ 8.62 (s, 1H), 8.14 (s, 1H), 7.79 (d, J = 8.8 Hz, 1H), 7.32~7.45 (m, 2H), 7.30~7.35 (m, 2H), 6.75 (s, 1H), 6.15~6.19 (m, 1H), 6.06 (s, 2H), 3.49 (s, 3H), 3.06 (d, J = 4.8 Hz, 3H), 2.82~2.88 (m, 2H), 2.66 (s, 3H), 2.60 (t, J = 4.8 Hz, 2H), 1.99~2.06 (m, 2H) | 588 |

Example 48

2-(bicyclo[3.1.0]hexan-1-yl)-5-(11-fluoro-6H-pyrido[2',3':5,6][1,3]oxazino[3,4-a]indol-2-yl)-N-methyl-6-(N-methylmethylsulfonamido)benzofuran-3-carboxamide

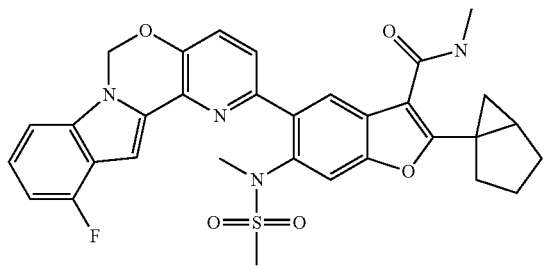 [SMILES: CNC(=O)c1c(C23CCCC2C3)oc2cc(N(C)S(C)(=O)=O)c(-c3ccc4c(n3)-c3cc5c(F)cccc5n3CO4)cc12]

Step 1 - 2-(bicyclo[3.1.0]hexan-1-yl)-5-bromo-N-methyl-6-(N-methylmethylsulfonamido)benzofuran-3-carboxamide

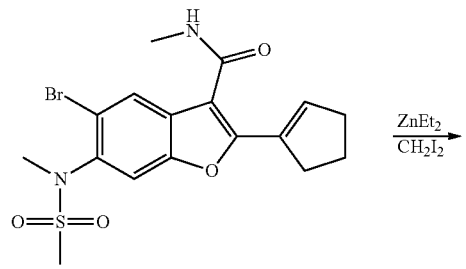

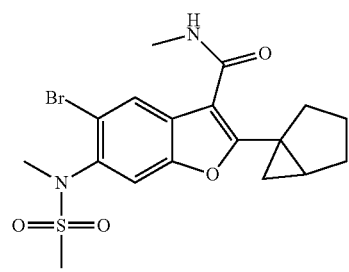

To a solution of 5-bromo-2-(cyclopent-1-en-1-yl)-N-methyl-6-(N-methylmethylsulfonamido)benzofuran-3-carboxamide (600 mg, 1.40 mmol) and $ZnEt_2$ (15 mL, 14.04 mmol) in DCM (10 mL) was added dropwise $CH_2I_2$ (1.2 mL, 14.04 mmol) at 0° C., and then the mixture was stirred at 25° C. After 3 hours, 10 mL $NH_4Cl$ (a.q.) was added, and the mixture was extracted with DCM (30 mL*3), and dried over $Na_2SO_4$. After concentration, the residue was purified by column chromatography (DCM:EtOAc=3:1) to give the product of 2-(bicyclo[3.1.0]hexan-1-yl)-5-bromo-N-methyl-6-(N-methylmethylsulfonamido)benzofuran-3-carboxamide (300 mg, yield: 48%). $^1$H-NMR (CDCl$_3$, 400 MHz) δ 8.30 (s, 1H), 7.60 (s, 1H), 6.16 (d, J=2.0 Hz, 1H), 3.34 (s, 3H), 3.12 (d, J=4.8 Hz, 3H), 3.07 (s, 3H), 2.10~2.21 (m, 2H), 2.01~2.09 (m, 2H), 1.86~1.99 (m, 2H), 1.38~1.46 (m, 1H), 1.37 (d, J=4.0 Hz, 2H). MS (M+H)$^+$: 441/443.

Step 2 - 2-(bicyclo[3.1.0]hexan-1-yl)-N-methyl-6-(N-methylmethylsulfonamido)-5-(4,4,5,5-tetramethyl-1,3,2-dioxaborolan-2-yl)benzofuran-3-carboxamide

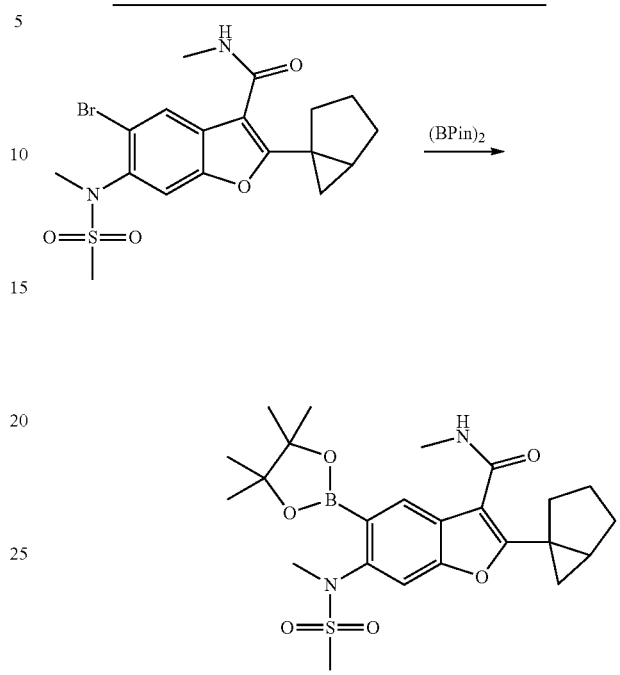

To a degassed solution of 2-(bicyclo[3.1.0]hexan-1-yl)-5-bromo-N-methyl-6-(N-methylmethylsulfonamido)benzofuran-3-carboxamide (220 mg, 0.50 mmol), bis(pinacolato)diboron (633 mg, 2.49 mmol), $CH_3COOK$ (147 mg, 1.50 mmol) in 1,4-Dioxane (8 mL) and $H_2O$ (1 mL) was added Pd(dppf)Cl$_2$ (10 mg), then the mixture was stirred at 130° C. After 3 hours, the solvent was removed by vacuum, and the mixture was washed with $H_2O$ (50 mL), extract with DCM (30 mL*3), and dried over $Na_2SO_4$. After concentrated, the residue was purified by prep-TLC (PE:EtOAc=1:1) to give the product of 2-(bicyclo[3.1.0]hexan-1-yl)-N-methyl-6-(N-methylmethylsulfonamido)-5-(4,4,5,5-tetramethyl-1,3,2-dioxaborolan-2-yl)benzofuran-3-carboxamide (121 mg, yield: 50%). $^1$H-NMR (CDCl$_3$, 400 MHz) 8.27 (s, 1H), 7.43 (s, 1H), 6.20 (d, J=4.0 Hz, 1H), 3.30 (s, 3H), 3.03 (d, J=4.8 Hz, 3H), 2.91 (s, 3H), 2.17~2.21 (m, 2H), 2.11~2.16 (m, 2H), 2.01~2.09 (m, 2H), 1.91~1.98 (m, 1H), 1.75 (d, J=4.0 Hz, 2H), 1.06 (s, 12H). MS (M+H)$^+$: 489.

Step 3 - Synthesis of 2-(bicyclo[3.1.0]hexan-1-yl)-5-(11-fluoro-6H-pyrido[2',3':5,6][1,3]oxazino[3,4-a]indol-2-yl)-N-methyl-6-(N-methylmethylsulfonamido)benzofuran-3-carboxamide

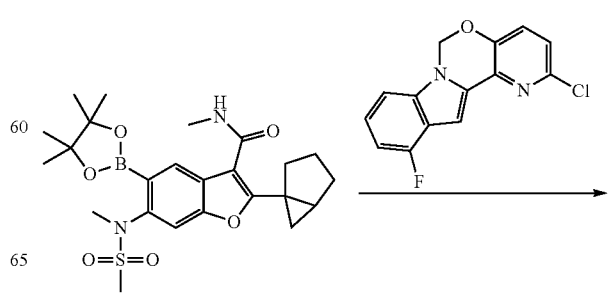

-continued

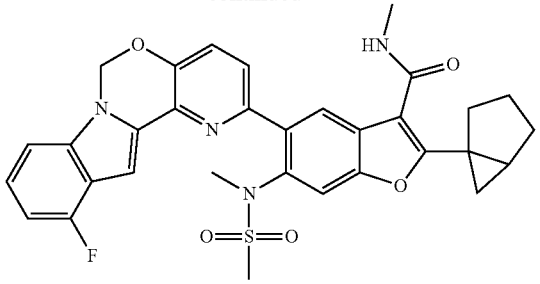

To a degassed solution of 2-(bicyclo[3.1.0]hexan-1-yl)-N-methyl-6-(N-methylmethylsulfonamido)-5-(4,4,5,5-tetramethyl-1,3,2-dioxaborolan-2-yl)benzofuran-3-carboxamide (100 mg, 0.20 mmol), 2-chloro-11-fluoro-6H-pyrido[2',3':5,6][1,3]oxazino[3,4-a]indole (67 mg, 0.24 mmol), $K_3PO_4$ (109 mg, 0.41 mmol) in 1,4-Dioxane (5 mL) and $H_2O$ (0.5 ml) was added $Pd(dba)_3$ (5 mg), X-Phos (5 mg) under $N_2$, then the mixture was stirred at 110° C. for 2 hours. The reaction mixture was cooled to RT and filtered. The filtrate was washed with $H_2O$, brine, extracted with DCM, and dried over $Na_2SO_4$. After concentration, the residue was purified by prep-HPLC to give the product of 2-(bicyclo[3.1.0]hexan-1-yl)-5-(11-fluoro-6H-pyrido[2',3':5,6][1,3]oxazino[3,4-a]indol-2-yl)-N-methyl-6-(N-methylmethylsulfonamido)benzofuran-3-carboxamide (20 mg, yield: 16%). $^1$H-NMR ($CDCl_3$, 400 MHz) δ 8.12 (s, 1H), 7.55 (s, 1H), 7.46 (s, 2H), 7.21 (s, 2H), 7.12 (d, J=8.0 Hz, 1H), 6.86 (q, J=8.0 Hz, 1H), 6.17 (d, J=4.0 Hz, 1H), 5.60 (s, 2H), 3.38 (s, 3H), 3.05 (d, J=4.8 Hz, 3H), 2.67 (s, 3H), 2.14~2.22 (m, 2H), 2.11~2.16 (m, 2H), 2.01~2.09 (m, 2H), 1.91~1.98 (m, 1H), 1.84 (d, J=4.0 Hz, 2H). MS (M+H)$^+$: 601.

Example 49

Example 49, depicted in the table below, was prepared in accordance with the method described in Example 48.

| Example | Structure | NMR | MS (M + H)$^+$ |
|---|---|---|---|
| 49 | 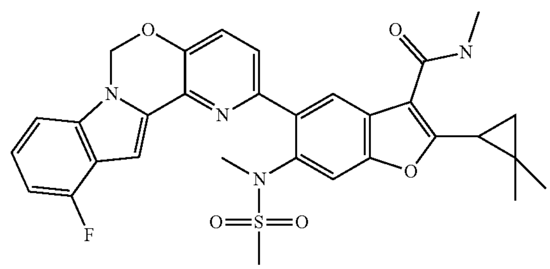 [SMILES: CNC(=O)c1c(C2CC2(C)C)oc2cc(N(C)S(C)(=O)=O)c(-c3ccc4c(n3)-c3cc5c(F)cccc5n3CO4)cc12] | $^1$H-NMR (CDCl$_3$, 400 MHz) δ 8.06 (s, 1H), 7.55 (s, 1H), 7.44~7.52 (m, 2H), 7.15~7.24 (m, 2H), 7.11 (d, J = 8.0 Hz, 1H), 6.84 (dd, J = 9.6, 8.0 Hz, 1H), 6.10 (d, J = 4.4 Hz, 1H), 5.99 (s, 2H), 3.35 (s, 3H), 3.04 (d, J = 4.8 Hz, 3H), 2.71 (s, 3H), 2.35 (dd, J = 8.0, 6.0 Hz, 1H), 1.42 (t, J = 5.2 Hz, 1H), 1.35 (s, 3H), 1.16 (dd, J = 8.4, 4.8 Hz, 1H), 1.07 (s, 3H). | 589 |

Example 50

2-(2,2-difluorocyclopropyl)-5-(11-fluoro-6H-pyrido[2',3':5,6][1,3]oxazino[3,4-a]indol-2-yl)-N-methyl-6-(N-methylmethylsulfonamido)benzofuran-3-carboxamide

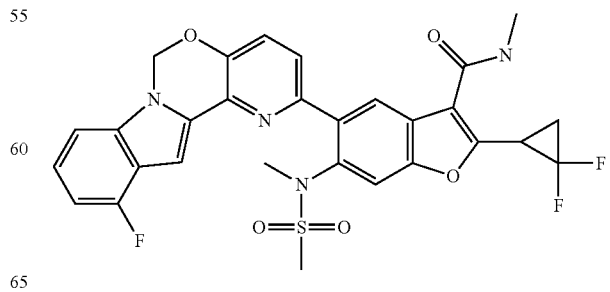

Step 1 - 5-bromo-2-(2,2-difluorocyclopropyl)-N-methyl-6-(N-methylmethylsulfonamido)benzofuran-3-carboxamide

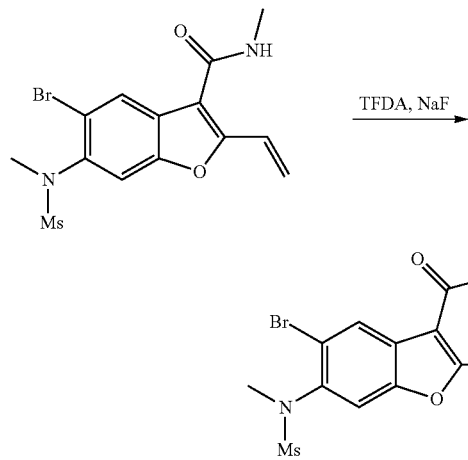

A solution of trimethylsilyl 2-fluorosulfonyl-2,2-difluoroacetate (31 mg, 0.12 mmol) in toluene (0.5 mL) was added dropwise to a solution of 5-bromo-N-methyl-6-(N-methylmethylsulfonamido)-2-vinylbenzofuran-3-carboxamide (30 mg, 0.07 mmol) and NaF (1 mg, 0.02 mmol) in diglyme (1 mL) at 120° C. over 15 min. The mixture was then stirred at 120° C. for 2 h. The mixture was concentrated in vacuum and the residue was purified by prep-TLC (PE:EA=1:1) to give the product of 5-bromo-2-(2,2-difluorocyclopropyl)-N-methyl-6-(N-methylmethylsulfonamido)benzofuran-3-carboxamide (7 mg, yield: 22%). $^1$H-NMR (DMSO-d$_6$, 400 MHz) δ 8.13 (s, 1H), 8.02 (s, 1H), 3.74~3.66 (m, 1H), 3.19 (s, 3H), 3.18 (s, 3H), 2.84 (s, 3H), 2.38~2.39 (m, 1H), 2.21~2.17 (m, 1H). MS (M+H)$^+$: 437/439.

Step 2 - 2-(2,2-difluorocyclopropyl)-N-methyl-6-(N-methylmethylsulfonamido)-5-(4,4,5,5-tetramethyl-1,3,2-dioxaborolan-2-yl)benzofuran-3-carboxamide

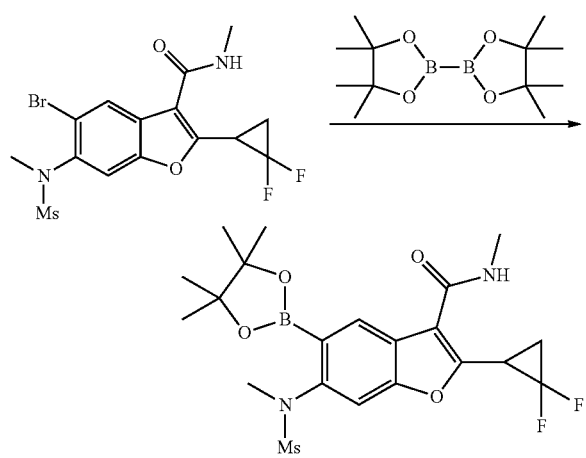

A mixture of 5-bromo-2-(2,2-difluorocyclopropyl)-N-methyl-6-(N-methylmethylsulfonamido)benzofuran-3-carboxamide (30 mg, 0.07 mmol), bis(pinacolato)diboron (87 mg, 0.34 mmol), Pd(dppf)Cl$_2$ (10 mg, 0.01 mmol) and KOAc (60 mg, 0.2 mmol) in DMF (2 mL) was stirred at 110° C. for 6 h. Water was added and the mixture was extracted with EtOAc. After concentrated, the residue was purified by prep-TLC (PE:EA=1:1) to give the crude product of 2-(2,2-difluorocyclopropyl)-N-methyl-6-(N-methylmethylsulfonamido)-5-(4,4,5,5-tetramethyl-1,3,2-dioxaborolan-2-yl)benzofuran-3-carboxamide (7 mg, yield: 20%). MS (M+H)$^+$: 485.

Step 3 - Synthesis of 2-(2,2-difluorocyclopropyl)-5-(11-fluoro-6H-pyrido[2',3':5,6][1,3]oxazino[3,4-a]indol-2-yl)-N-methyl-6-(N-methylmethylsulfonamido)benzofuran-3-carboxamide

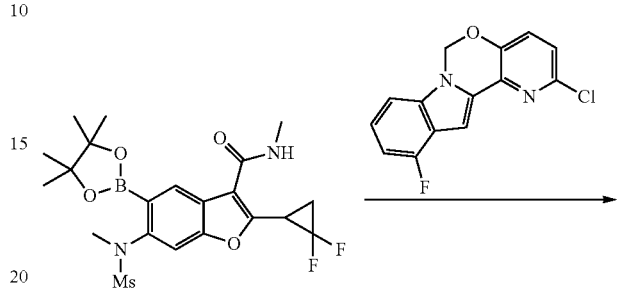

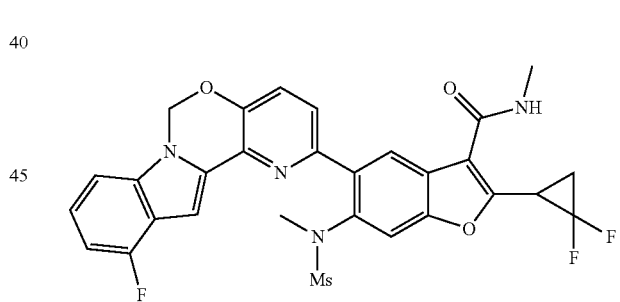

A mixture of 2-(2,2-difluorocyclopropyl)-N-methyl-6-(N-methylmethylsulfonamido)-5-(4,4,5,5-tetramethyl-1,3,2-dioxaborolan-2-yl)benzofuran-3-carboxamide (20 mg, 0.04 mmol), 2-chloro-11-fluoro-6H-pyrido[2',3':5,6][1,3]oxazino[3,4-a]indole (11 mg, 0.04 mmol), Pd$_2$(dba)$_3$ (10 mg, 0.01 mmol), X-Phos (10 mg, 0.02 mmol) and K$_3$PO$_4$ (60 mg, 0.12 mmol) in DMF (2 mL) was stirred at 100° C. for 6 h. Water was added and the mixture was extracted with EtOAc. After concentration, the residue was purified by prep-TLC (PE:EA=1:3) to give the product of 2-(2,2-difluorocyclopropyl)-5-(11-fluoro-6H-pyrido[2',3':5,6][1,3]oxazino[3,4-a]indol-2-yl)-N-methyl-6-(N-methylmethylsulfonamido)benzofuran-3-carboxamide (2 mg, yield: 8%). $^1$H-NMR (MeOD, 400 MHz) δ 8.00 (s, 1H), 7.83 (s, 1H), 7.60 (s, 2H), 7.32 (d, J=8.4 Hz, 1H), 7.26~7.20 (m, 2H), 6.93 (dd, J=8.0, 10.4 Hz, 1H), 6.11 (s, 2H), 3.64~3.56 (m, 1H), 3.34 (s, 3H), 2.99 (s, 3H), 2.98 (s, 3H), 2.26~2.17 (m, 2H). MS (M+H)+: 597.

Example 51

(R or S)-2-cyclopropyl-5-(11-fluoro-6-(hydroxymethyl)-6H-pyrido[2',3':5,6][1,3]oxazino[3,4-a]indol-2-yl)-N-methyl-6-(N-methylmethylsulfonamido)benzofuran-3-carboxamide

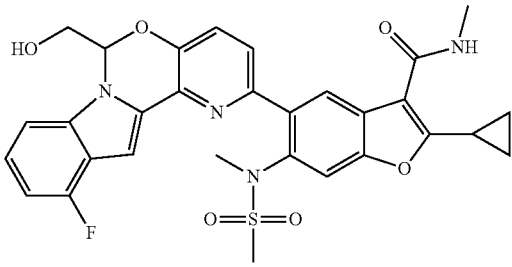 [SMILES: CNC(=O)c1c(C2CC2)oc2cc(N(C)S(C)(=O)=O)c(-c3ccc4c(n3)-c3cc5c(F)cccc5n3C(CO)O4)cc12]

Step 1 - Synthesis of ethyl 5-bromo-2-cyclopropylbenzofuran-3-carboxylate

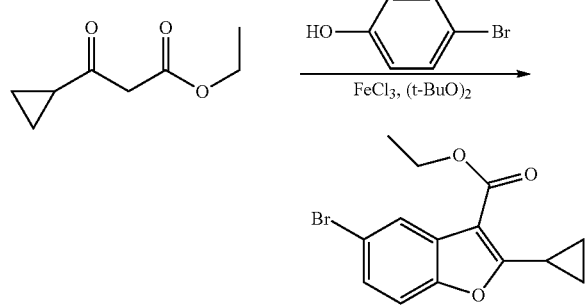

(t-BuO)$_2$ (94 g, 640 mol) was added to a solution of ethyl 3-cyclopropyl-3-oxopropanoate (50 g, 320 mmol), 4-bromophenol (166 g, 9.6 mol) and FeCl$_3$.6H$_2$O (5.8 g, 32 mmol) in Di-chlorine Ethane (316 g, 3.2 mol) under N$_2$ gas at 25° C. The mixture was stirred at 80° C. for 6 hours. The solvent was removed and the residue was purified by column chromatography (eluted with PE:EA from 20:1 to 10:1) to furnish the pure product of ethyl 5-bromo-2-cyclopropylbenzofuran-3-carboxylate (20.0 g, yield: 21%). $^1$H-NMR (400 MHz, CDCl$_3$) δ 8.02 (s, 1H), 7.30 (d, J=7.2 Hz, 1H), 7.18 (d, J=7.2 Hz, 1H), 4.42 (q, J=7.2 Hz, 2H), 3.01~3.05 (m, 1H), 1.44 (t, J=7.2 Hz, 3H), 1.24~1.26 (m, 2H), 1.16~1.19 (m, 2H). MS (M+H)+: 309/311.

Step 2 - Synthesis of ethyl 5-bromo-2-cyclopropyl-6-nitrobenzofuran-3-carboxylate

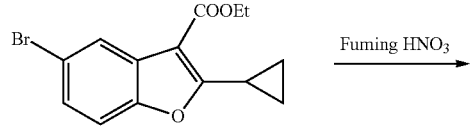

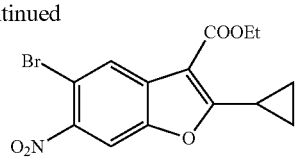

To a solution of compound ethyl 5-bromo-2-cyclopropylbenzofuran-3-carboxylate (10 g, 34 mmol) in CHCl$_3$ (60 mL), fuming HNO$_3$ (12 mL, 95%) was added dropwise at −20° C. over 90 min and the mixture was stirred at 0° C. for 1 hour. The reaction mixture was added to ice water and extracted with CH$_2$Cl$_2$. The organic layer was washed with NaHCO$_3$ (aq.) and brine. The solvent was removed by distillation to provide the crude product of ethyl 5-bromo-2-cyclopropyl-6-nitrobenzofuran-3-carboxylate (4.5 g, yield: 40%). $^1$H-NMR (400 MHz, CDCl$_3$) δ 8.26 (s, 1H), 7.95 (s, 1H), 4.46 (q, J=7.2 Hz, 2H), 3.06~3.10 (m, 1H), 1.46 (t, J=7.2 Hz, 3H), 1.34~1.36 (m, 2H), 1.28~1.32 (m, 2H). MS (M+H)+: 354/356.

Step 3 - Synthesis of ethyl 6-amino-5-bromo-2-cyclopropylbenzofuran-3-carboxylate

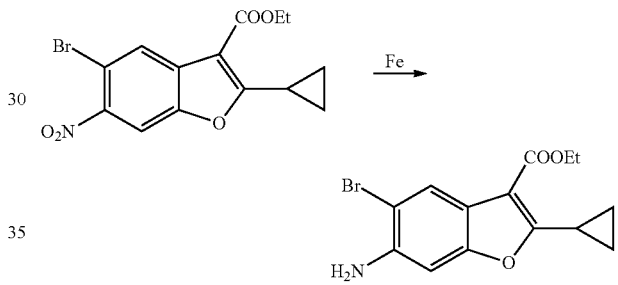

A mixture of crude compound ethyl 5-bromo-2-cyclopropyl-6-nitrobenzofuran-3-carboxylate (8.5 g, 25 mmol), iron filings (4.1 g, 75 mmol) and NH$_4$Cl (8 g, 150 mmol) in MeOH-THF—H$_2$O (2:2:1, 100 mL) were stirred at reflux for 3 hours. After being filtered and concentrated in vacuum, the residue was purified by column chromatography (eluted with PE:EA from 20:1 to 10:1) to furnish the pure product of ethyl 6-amino-5-bromo-2-cyclopropylbenzofuran-3-carboxylate (7.00 g, yield: 91%). $^1$H-NMR (400 MHz, CDCl$_3$) δ 7.93 (s, 1H), 6.75 (s, 1H), 4.40 (q, J=7.2 Hz, 2H), 4.11 (s, 2H), 2.94~2.99 (m, 1H), 1.43 (t, J=7.2 Hz, 3H), 1.19~1.21 (m, 2H), 1.12~1.15 (m, 2H). MS (M+H)+: 324/326.

Step 4 - Synthesis of 6-amino-5-bromo-2-cyclopropylbenzofuran-3-carboxylic acid

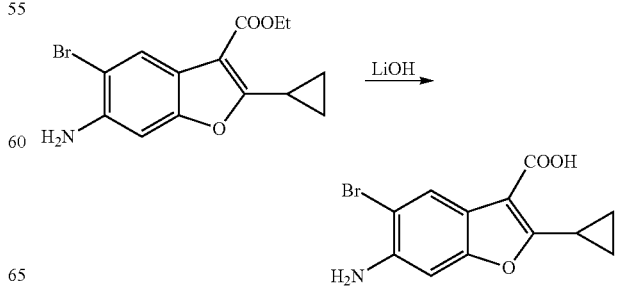

To a solution of ethyl 6-amino-5-bromo-2-cyclopropylbenzofuran-3-carboxylate (7 g, 22.5 mmol) in 1,4-dioxane and H$_2$O (50 mL and 50 mL) was added LiOH.H$_2$O (4.6 g, 112 mmol). The reaction mixture was refluxed for 2 hours, and then 400 mL H$_2$O was added to the reaction mixture. After acidifying to pH 4~5 with HCl, the resulting solid were filtered to give the product of 6-amino-5-bromo-2-cyclopropylbenzofuran-3-carboxylic acid (6.5 g, yield: 97%). $^1$H-NMR (400 MHz, MeOD) δ 7.86 (s, 1H), 6.85 (s, 1H), 4.31 (s, 2H), 2.93~3.00 (m, 1H), 1.19~1.22 (m, 2H), 1.13~1.16 (m, 2H). MS (M+H)$^+$: 296/298.

Step 5 - Synthesis of 6-amino-5-bromo-2-cyclopropyl-N-methylbenzofuran-3-carboxamide

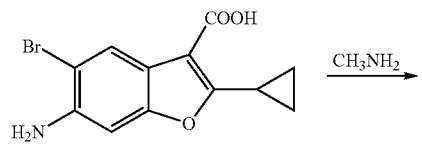

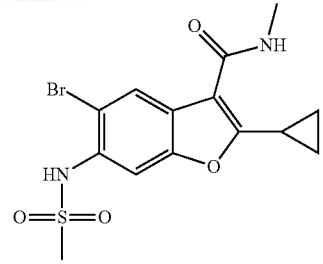

To a solution of 6-amino-5-bromo-2-cyclopropylbenzofuran-3-carboxylic acid (6.5 g, 22 mmol) in dry DMF (500 mL) were added EDCI (2.98 g, 2.4 mmol) and HOBT (6.33 g, 3.6 mmol). The reaction mixture was stirred at room temperature for 2 h, and then Et$_3$N (20 mL) and MeNH$_2$.HCl (7.3 g, 110 mmol) were added to the reaction mixture. After stirring for another 2 hours, the reaction mixture was concentrated in vacuum and Na$_2$CO$_3$ (a.q., 300 mL) was added to the mixture. The resulting solid was filtered to give the crude product, which was purified by column chromatography (DCM:MeOH=30:1) to give the product of 6-amino-5-bromo-2-cyclopropyl-N-methylbenzofuran-3-carboxamide (5.3 g, yield: 78%). $^1$H-NMR (400 MHz, CDCl$_3$) δ 7.69 (s, 1H), 6.77 (s, 1H), 5.88 (s, 1H), 4.11 (s, 2H), 3.04 (d, J=4.8 Hz, 3H), 2.69~2.73 (m, 1H), 1.10~1.16 (m, 2H), 1.07~1.09 (m, 2H). MS (M+H)$^+$: 309/311.

Step 6 - Synthesis of 5-bromo-2-cyclopropyl-N-methyl-6-(methylsulfonamido)benzofuran-3-carboxamide

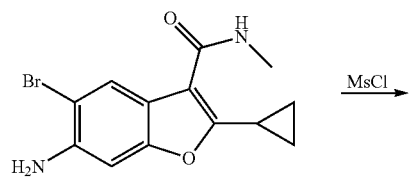

To a degassed solution of 6-amino-5-bromo-2-cyclopropyl-N-methylbenzofuran-3-carboxamide (4.0 g, 13 mmol) in DCM/Pyridine (80 mL/10 mL) was added MsCl (4.5 g, 39 mmol) under N$_2$ at 0° C. over a period of 30 min. The reaction mixture was stirred at 25° C. for 8 hours. The reaction mixture was diluted with water and extracted with EtOAc. The organic phase was washed with brine and dried over Na$_2$SO$_4$. After concentration, the residue was purified by column chromatography (PE) to give crude product of 5-bromo-2-cyclopropyl-N-methyl-6-(methylsulfonamido)benzofuran-3-carboxamide (4.5 g, yield: 90%). $^1$H-NMR (400 MHz, CDCl$_3$) δ 7.98 (s, 1H), 7.71 (s, 1H), 6.79 (s, 1H), 5.93 (s, 1H), 3.06 (d, J=4.8 Hz, 3H), 2.96 (s, 3H), 2.59~2.61 (m, 1H), 1.13~1.14 (m, 2H), 1.16~1.20 (m, 2H). MS (M+H)$^+$: 387/389.

Step 7 - Synthesis of 5-bromo-2-cyclopropyl-N-methyl-6-(N-methylmethylsulfonamido)benzofuran-3-carboxamide

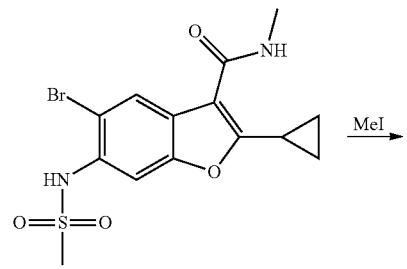

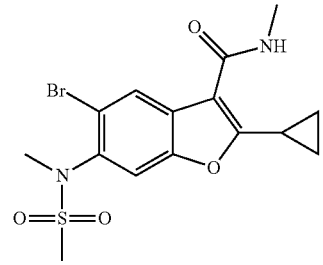

To a suspension of compound 5-bromo-2-cyclopropyl-N-methyl-6-(methylsulfonamido)benzofuran-3-carboxamide (1.5 g, 3.9 mmol) and K$_2$CO$_3$ (1.6 mg, 7.8 mmol) in DMF (15 mL) was added dropwise CH$_3$I (1.1 mg, 7.8 mmol) at 0° C. under N$_2$, and then the mixture was stirred at 80° C. for 2 hours. After concentration in vacuum, the residue was suspended in H$_2$O and extracted with DCM. The combined organic layer was washed with H$_2$O, brine and dried over Na$_2$SO$_4$. The mixture was filtered and concentrated to give the product of compound 5-bromo-2-cyclopropyl-N-methyl-6-(N-methylmethylsulfonamido)benzofuran-3-carboxamide (1 g, yield: 65%). $^1$H-NMR (400 MHz, CDCl$_3$) δ 7.70 (s, 1H), 6.98 (s, 1H), 5.63 (s, 1H), 3.05 (s, 3H), 2.79 (s, 6H), 2.39~2.43 (m, 1H), 0.95~0.97 (m, 2H), 0.89~0.91 (m, 2H). MS (M+H)$^+$: 401/403.

Step 8 - Synthesis of 2-cyclopropyl-N-methyl-6-(N-methylmethylsulfonamido)-5-(4,4,5,5-tetramethyl-1,3,2-dioxaborolan-2-yl)benzofuran-3-carboxamide

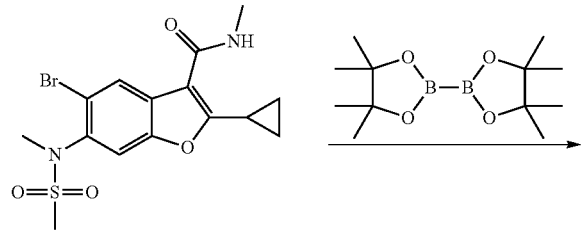

Step 9 - Synthesis of 2-cyclopropyl-5-(11-fluoro-6-(hydroxymethyl)-6H-pyrido[2',3':5,6][1,3]oxazino[3,4-a]indol-2-yl)-N-methyl-6-(N-methylmethylsulfonamido)benzofuran-3-carboxamide

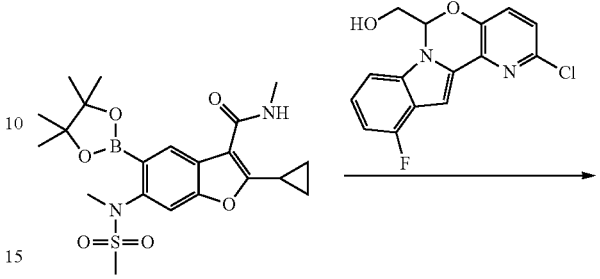

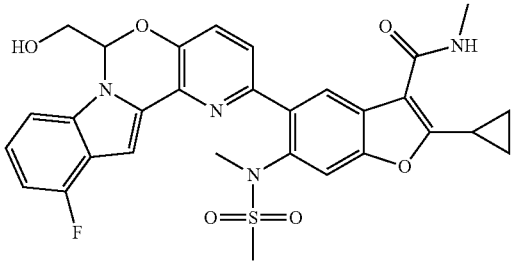

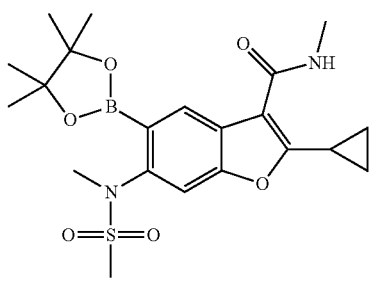

To a $N_2$ degassed solution of 5-bromo-2-cyclopropyl-N-methyl-6-(N-methylmethylsulfonamido)benzofuran-3-carboxamide (2.0 g, 5.0 mmol), KOAc (1.5 g, 15 mmol) and bis(pinacolato)diboron (6.3 g, 25 mmol) in dioxane (20 mL) was added Pd(dppf)Cl$_2$ (650 mg, 1.0 mmol). The reaction mixture was stirred at 100° C. for 3 hours, and then filtered through a celite pad. The filtrate was concentrated in vacuo, and the residue was purified by column chromatography (PE:EA=1:1) to give the product of compound 2-cyclopropyl-N-methyl-6-(N-methylmethylsulfonamido)-5-(4,4,5,5-tetramethyl-1,3,2-dioxaborolan-2-yl)benzofuran-3-carboxamide (800 mg, yield: 37%). $^1$H-NMR (400 MHz, CDCl$_3$) δ 8.02 (s, 1H), 7.41 (s, 1H), 6.14 (s, 1H), 3.32 (s, 3H), 3.06 (d, J=4.8 Hz, 3H), 2.93 (s, 3H), 2.81~2.87 (m, 1H), 1.20 (s, 12H) 1.13~1.16 (m, 2H), 1.10~1.13 (m, 2H). MS (M+H)$^+$: 449.

To a degassed solution of 2-cyclopropyl-5-(11-fluoro-6-(hydroxymethyl)-6H-pyrido[2',3':5,6][1,3]oxazino[3,4-a]indol-2-yl)-N-methyl-6-(N-methylmethylsulfonamido)benzofuran-3-carboxamide (74 mg, 0.16 mmol), (2-chloro-11-fluoro-6H-pyrido[2',3':5,6][1,3]oxazino[3,4-a]indol-6-yl)methanol (50 mg, 0.16 mmol) and K$_3$PO$_4$.3H$_2$O (131 mg, 0.49 mmol) in 1,4-dioxane (4 mL) was added Pd$_2$(dba)$_3$ (16 mg, 0.016 mmol) and X-Phos (16 mg, 0.03 mmol) under N$_2$ protection. The reaction mixture was heated to 100° C. and stirred for 3 hours, and then filtered through a celite pad. The filtrate was concentrated in vacuo, and the residue was purified by column chromatography (PE:EA=1:1) to give the product of 2-cyclopropyl-5-(11-fluoro-6-(hydroxymethyl)-6H-pyrido[2',3':5,6][1,3]oxazino[3,4-a]indol-2-yl)-N-methyl-6-(N-methylmethylsulfonamido)benzofuran-3-carboxamide (41 mg, yield: 43%). $^1$H-NMR (400 MHz, CDCl$_3$) δ 7.85 (s, 1H), 7.43~7.48 (m, 3H), 7.13~7.22 (m, 3H), 6.81~6.85 (m, 1H), 6.42~6.44 (m, 1H), 6.02~6.04 (m, 1H), 3.96~3.98 (m, 1H), 3.84~3.87 (m, 1H), 3.33 (s, 3H), 3.02 (d, J=4.8 Hz, 3H), 2.79~2.80 (m, 1H), 2.59 (s, 3H), 1.24~1.27 (m, 2H), 1.16~1.19 (m, 2H). MS (M+H)$^+$: 591.

Examples 52 and 53

Examples 52 & 53, depicted in the table below, were prepared in accordance with the method described in Example 54.

| Compound ID | Structure | NMR | MS (M + H)+ |
|---|---|---|---|
| 52 | R or S | ¹H-NMR (CDCl₃, 400 MHz) δ 8.34 (s, 1H), 7.90 (s, 1H), 7.87 (s, 1H), 7.39 (s, 1H), 7.20~7.39 (m, 1H), 7.17~7.19 (m, 1H), 7.06 (s, 1H), 6.80~6.84 (m, 1H), 6.41~6.47 (m, 2H), 3.80~3.85 (m, 1H), 3.57~3.59 (m, 1H), 3.16 (s, 3H), 2.93 (d, J = 4.8 Hz, 3H), 2.90~2.94 (m, 1H), 2.80 (s, 3H), 1.21~1.25 (m, 2H), 1.15~1.17 (m, 2H). | 591 |
| 53 | 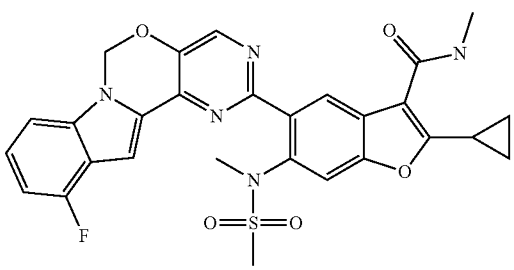 [SMILES: CNC(=O)c1c(C2CC2)oc2cc(N(C)S(C)(=O)=O)c(-c3ncc4c(n3)-c3cc5c(F)cccc5n3CO4)cc12] | ¹H-NMR (CDCl₃, 400 MHz) δ 8.63 (s, 1H), 8.18 (s, 1H), 7.55 (s, 1H), 7.46 (s, 1H), 7.28~7.32 (m, 1H), 7.13~7.15 (m, 1H), 6.86~6.91 (m, 1H), 6.12 (s, 1H), 6.06 (m, 2H), 3.45 (s, 3H), 3.07 (d, J = 4.8 Hz, 3H), 2.91~2.95 (m, 1H), 2.81 (s, 3H), 1.26~1.30 (m, 2H), 1.19~1.22 (m, 2H). | 562 |

Example 54

5-(11-fluoro-6H-pyrido[2',3':5,6][1,3]oxazino[3,4-a]indol-2-yl)-N2,N3-dimethyl-6-(N-methylmethylsulfonamido)benzofuran-2,3-dicarboxamide Step 1 - Synthesis of methyl 5-bromo-3-(methylcarbamoyl)-6-(N-methylmethylsulfonamido)benzofuran-2-carboxylate

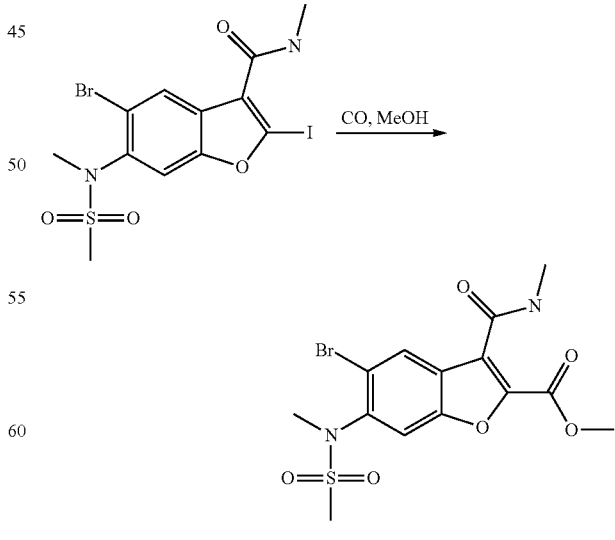

To a solution of 5-bromo-2-iodo-N-methyl-6-(N-methylmethylsulfonamido)benzofuran-3-carboxamide (4.0 g, 8.21 mmol) in MeOH (10 mL) and DMSO (35 mL) was added Pd(PPh$_3$)$_2$Cl$_2$ under Ar$_e$. The suspension was degassed under vacuum and purged with CO 4 times. The mixture was stirred under CO (50 Psi) at 50° C. for 16 h. Then 30 mL MeOH was added to the mixture. The resulting solid was filtered to give the product of compound methyl 5-bromo-3-(methylcarbamoyl)-6-(N-methylmethylsulfonamido)benzofuran-2-carboxylate (2.90 g, yield: 84%). $^1$H-NMR (CDCl$_3$, 400 MHz) δ 9.39 (br s, 1H), 8.94 (s, 1H), 7.74 (s, 1H), 4.08 (s, 3H), 3.34 (s, 3H), 3.08 (s, 3H), 3.04 (d, J=4.8 Hz, 3H). MS (M+H)$^+$: 419/421.

Step 2 - Synthesis of methyl 3-(methylcarbamoyl)-6-(N-methylmethylsulfonamido)-5-(4,4,5,5-tetramethyl-1,3,2-dioxaborolan-2-yl)benzofuran-2-carboxylate

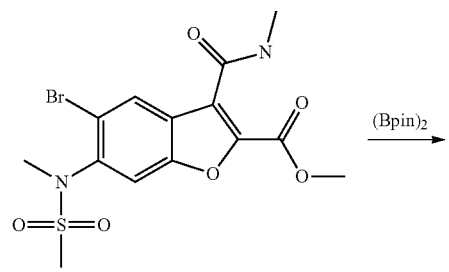

To a mixture of methyl 5-bromo-3-(methylcarbamoyl)-6-(N-methylmethylsulfonamido)benzofuran-2-carboxylate (1.0 g, 2.39 mmol), bis(pinacolato)diboron (908 mg, 3.58 mmol), CH$_3$COOK (702 mg, 7.16 mmol) in 1,4-dioxane was added Pd(dtbpf)Cl$_2$ under N$_2$. The mixture was stirred at 90 for 1.5 h. Then it was concentrated in vacuo and the residue was purified by column chromatography (PE:EA=5:1-DCM:MeOH=100:1) to give the product of compound methyl 3-(methylcarbamoyl)-6-(N-methylmethylsulfonamido)-5-(4,4,5,5-tetramethyl-1,3,2-dioxaborolan-2-yl)benzofuran-2-carboxylate (700 mg, yield: 64%). $^1$H-NMR (CDCl$_3$, 400 MHz) δ 9.30 (br s, 1H), 9.06 (s, 1H), 7.62 (s, 1H), 4.07 (s, 3H), 3.35 (s, 3H), 3.05 (d, J=4.8 Hz, 3H), 2.96 (s, 3H), 1.35 (s, 12H). MS (M+H)$^+$: 467.

Step 3 - Synthesis of methyl 5-(11-fluoro-6H-pyrido[2',3':5,6][1,3]oxazino[3,4-a]indol-2-yl)-3-(methylcarbamoyl)-6-(N-methylmethylsulfonamido)benzofuran-2-carboxylate

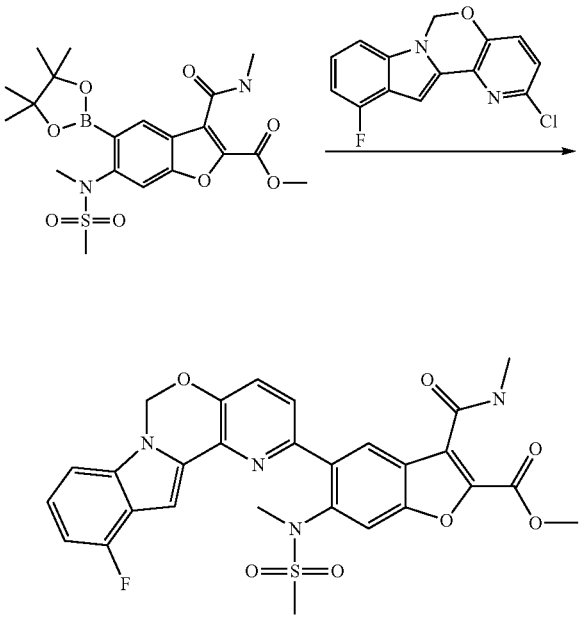

To a mixture of compound methyl 3-(methylcarbamoyl)-6-(N-methylmethylsulfonamido)-5-(4,4,5,5-tetramethyl-1,3,2-dioxaborolan-2-yl)benzofuran-2-carboxylate (700 mg, 1.50 mmol), 2-chloro-11-fluoro-6H-pyrido[2',3':5,6][1,3]oxazino[3,4-a]indole (536 mg, 1.95 mmol) and K$_3$PO$_4$.3H$_2$O (1.20 g, 4.50 mmol) in 1,4-dioxane (25 mL), Pd$_2$(dba)$_3$/XPhos (50 mg/50 mg) was added under N$_2$ protection. After stirring at 100° C. for 3 h, the reaction mixture was concentrated in vacuo, suspended in water and extracted with EtOAc. The organic layer was washed with brine, dried over Na$_2$SO$_4$ and concentrated. The residue was purified by prep-TLC (DCM:MeOH=200:1) to give the product of methyl 5-(11-fluoro-6H-pyrido[2',3':5,6][1,3]oxazino[3,4-a]indol-2-yl)-3-(methylcarbamoyl)-6-(N-methylmethylsulfonamido)benzofuran-2-carboxylate (700 mg, yield: 80%). $^1$H-NMR (CDCl$_3$, 400 MHz) δ 9.41 (br s, 1H), 8.79 (s, 1H), 7.74 (s, 1H), 7.55~7.45 (m, 2H), 7.24~7.17 (m, 2H), 7.12 (d, J=8.0 Hz, 1H), 6.88~6.81 (m, 1H), 6.01 (s, 2H), 4.10 (s, 3H), 3.40 (s, 3H), 3.05 (d, J=4.4 Hz, 3H), 2.69 (s, 3H). MS (M+H)$^+$: 579.

Step 4 - Synthesis of 5-(11-fluoro-6H-pyrido[2',3':5,6][1,3]oxazino[3,4-a]indol-2-yl)-3-(methylcarbamoyl)-6-(N-methylmethylsulfonamido)benzofuran-2-carboxylic acid

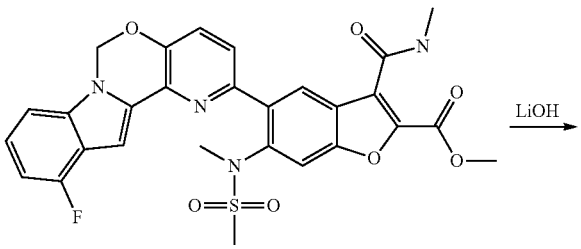

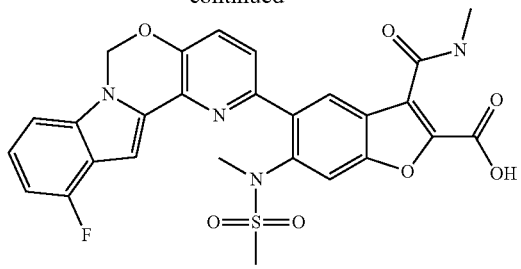

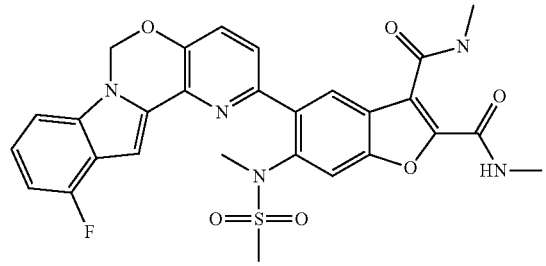 [SMILES: CNC(=O)c1oc2cc(N(C)S(C)(=O)=O)c(-c3ccc4c(n3)-c3cc5c(F)cccc5n3CO4)cc2c1C(=O)NC]

To a suspension of compound methyl 5-(11-fluoro-6H-pyrido[2',3':5,6][1,3]oxazino[3,4-a]indol-2-yl)-3-(methylcarbamoyl)-6-(N-methylmethylsulfonamido)benzofuran-2-carboxylate (540 mg, 0.93 mmol) in 1,4-dioxane/H₂O (6 mL/1 mL) was added LiOH.H₂O (196 mg, 4.67 mmol). The mixture was stirred at RT overnight. Then it was concentrated in vacuo, diluted with water, acidized with HCl(aq. 2 M) and extracted with EtOAc. The organic layer was washed with brine, dried over Na₂SO₄ and concentrated give the product of compound 5-(11-fluoro-6H-pyrido[2',3':5,6][1,3]oxazino[3,4-a]indol-2-yl)-3-(methylcarbamoyl)-6-(N-methylmethylsulfonamido)benzofuran-2-carboxylic acid (500 mg, yield: 95%). It was used for the next step without further purification. ¹H-NMR (DMSO-d₆, 400 MHz) δ 9.21 (br s, 1H), 8.17 (s, 1H), 8.11 (s, 1H), 7.69 (d, J=8.4 Hz, 1H), 7.54~7.58 (m, 1H), 7.49 (d, J=8.4 Hz, 1H), 7.28~7.11 (m, 2H), 7.07 (s, 1H), 6.95~6.88 (m, 1H), 6.25 (s, 2H), 3.28 (s., 3H), 2.95 (s, 3H), 2.83 (d, J=4.4 Hz, 3H). MS (M+H)⁺: 565.

Step 5 - Synthesis of 5-(11-fluoro-6H-pyrido[2',3':5,6][1,3]oxazino[3,4-a]indol-2-yl)-N2,N3-dimethyl-6-(N-methylmethylsulfonamido)benzofuran-2,3-dicarboxamide

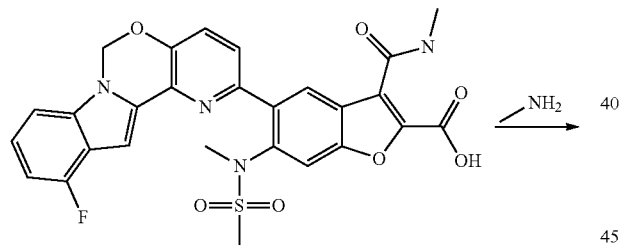

A mixture of compound 5-(11-fluoro-6H-pyrido[2',3':5,6][1,3]oxazino[3,4-a]indol-2-yl)-3-(methylcarbamoyl)-6-(N-methylmethylsulfonamido)benzofuran-2-carboxylic acid (50 mg, 0.09 mmol), HOBT (24 mg, 0.17 mmol), EDCI (102 mg, 0.53 mmol), methanamine hydrochloride (42 mg, 0.62 mmol) and Et₃N (72 mg, 0.71 mmol) in DMF (2 mL) was stirred overnight at room temperature. The reaction mixture was concentrated in vacuo, the residue was purified by prep-TLC (DCM:MeOH=200:1) to give the product 5-(11-fluoro-6H-pyrido[2',3':5,6][1,3]oxazino[3,4-a]indol-2-yl)-N2,N3-dimethyl-6-(N-methylmethylsulfonamido)benzofuran-2,3-dicarboxamide (20 mg, yield: 39%). ¹H NMR (CDCl₃, 400 MHz) δ 10.49 (br s, 1H), 8.81 (s, 1H), 7.68 (s, 1H), 7.49 (s, 2H), 7.24~7.17 (m, 3H), 7.12 (d, J=8.2 Hz, 1H), 6.88~6.81 (m, 1H), 6.01 (s, 2H), 3.39 (s, 3H), 3.12 (d, J=5.2 Hz, 3H), 3.02 (d, J=4.8 Hz, 3H), 2.65 (s, 3H). MS (M+H)⁺: 578.

Examples 55-57

Examples 55-57, depicted in the table below, were prepared in accordance with the method described in Example 57.

| Example | Structure | NMR | MS (M + H)⁺ |
|---|---|---|---|
| 55 | 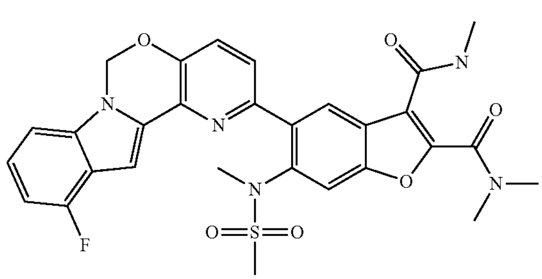 [SMILES: CNC(=O)c1c(C(=O)N(C)C)oc2cc(N(C)S(C)(=O)=O)c(-c3ccc4c(n3)-c3cc5c(F)cccc5n3CO4)cc12] | ¹H-NMR (CDCl₃, 400 MHz) δ 9.00 (br s, 1H), 8.55 (s, 1H), 7.71 (s, 1H), 7.53~7.45 (m, 2H), 7.24-7.16 (m, 2H), 7.11 (d, J = 8.2 Hz, 1H), 6.88~6.81 (m, 1H), 6.00 (s, 2H), 3.40 (s, 3H), 3.21 (s, 6H), 2.98 (d, J = 4.8 Hz, 3H), 2.66 (s, 3H). | 592 |

| Example | Structure | NMR | MS (M + H)+ |
|---|---|---|---|
| 56 | 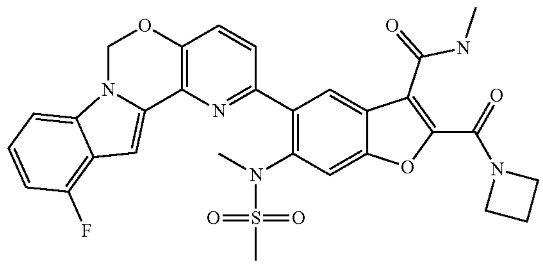 [SMILES: CNC(=O)c1c(C(=O)N2CCC2)oc2cc(N(C)S(C)(=O)=O)c(-c3ccc4c(n3)-c3cc5c(F)cccc5n3CO4)cc12] | ¹H-NMR (CDCl₃, 400 MHz) δ 10.55 (br s, 1H), 8.81 (s, 1H), 7.69 (s, 1H), 7.55~7.40 (m, 2H), 7.25-7.14 (m, 2H), 7.10 (d, J = 8.4 Hz, 1H), 6.84 (m, 1H), 5.99 (s, 2H), 4.78 (t, J = 7.6 Hz, 2H), 4.30 (t, J = 7.6 Hz, 2H), 3.39 (s, 3H), 2.98 (d, J = 4.8 Hz, 3H), 2.69~2.60 (m, 3H), 2.48 (m, 2H). | 604 |
| 57 | 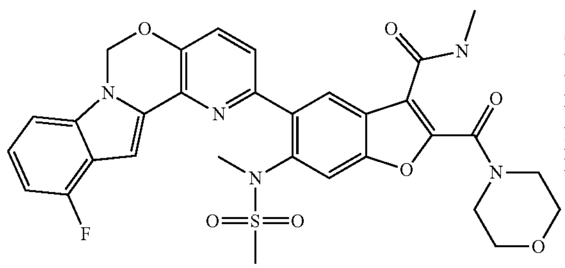 [SMILES: CNC(=O)c1c(C(=O)N2CCOCC2)oc2cc(N(C)S(C)(=O)=O)c(-c3ccc4c(n3)-c3cc5c(F)cccc5n3CO4)cc12] | ¹H-NMR (CDCl₃, 400 MHz) δ 8.86 (d, J = 4.8 Hz, 1H), 8.53 (s, 1H), 7.70 (s, 1H), 7.54~7.43 (m, 2H), 7.25~7.16 (m, 2H), 7.11 (d, J = 8.2 Hz, 1H), 6.85 (m, 1H), 6.00 (s, 2H), 3.85 (s, 4H), 3.78 (m, 2H), 3.68 (m, 2H), 3.39 (s, 3H), 2.99 (d, J = 4.8 Hz, 3H), 2.66 (s, 3H). | 634 |

Example 58

5-(11-fluoro-6H-pyrido[2',3':5,6][1,3]oxazino[3,4-a]indol-2-yl)-N-methyl-2-(5-methyl-1,3,4-oxadiazol-2-yl)-6-(N-methylmethylsulfonamido)benzofuran-3-carboxamide

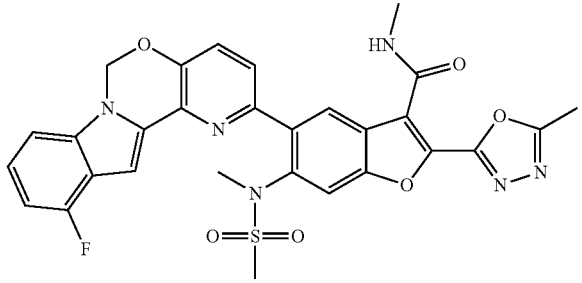 [SMILES: CNC(=O)c1c(-c2nnc(C)o2)oc2cc(N(C)S(C)(=O)=O)c(-c3ccc4c(n3)-c3cc5c(F)cccc5n3CO4)cc12]

To a suspension of compound methyl 5-bromo-3-(methylcarbamoyl)-6-(N-methylmethylsulfonamido)benzofuran-2-carboxylate in EtOH was added hydrazine hydrate (421 mg, 7.16 mmol). The mixture was refluxed overnight. Then it was concentrated in vacuo and the resulting solid was washed with MeCN to give the compound 5-bromo-2-(hydrazinecarbonyl)-N-methyl-6-(N-methylmethylsulfonamido)benzofuran-3-carboxamide (600 mg, yield: 100%). It was used for the next step without further purification. ¹H-NMR (DMSO-d₆, 400 MHz) δ 10.33 (br s, 1H), 8.60 (s, 1H), 7.96 (s, 1H), 5.03 (br s, 3H), 3.22 (s, 3H), 3.20 (s, 3H), 2.87 (d, J=4.8 Hz, 3H). MS (M+H)⁺: 419/421.

Step 1 - Synthesis of 5-bromo-2-(hydrazinecarbonyl)-N-methyl-6-(N-methylmethylsulfonamido)benzofuran-3-carboxamide

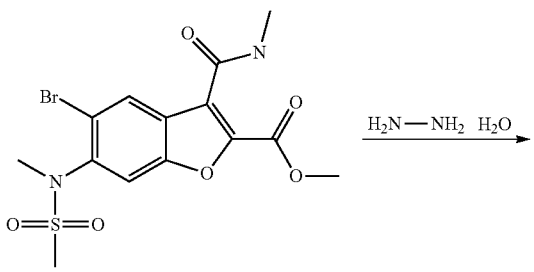

Step 2 - Synthesis of 2-(2-acetylhydrazinecarbonyl)-5-bromo-N-methyl-6-(N-methylmethylsulfonamido)benzofuran-3-carboxamide

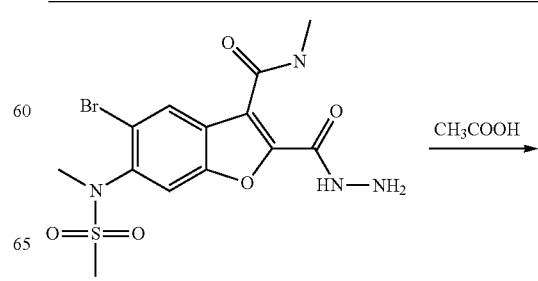

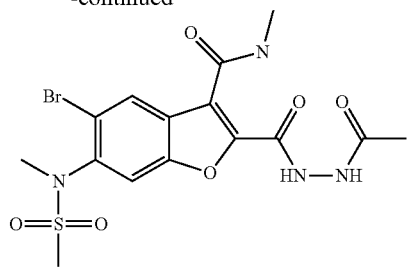

A mixture of compound 5-bromo-2-(hydrazinecarbonyl)-N-methyl-6-(N-methylmethylsulfonamido)benzofuran-3-carboxamide (210 mg, 0.50 mmol), EDCI (384 mg, 2.0 mmol) and acetic acid (60 mg, 1.0 mmol) in DMF (5 mL) was stirred overnight at room temperature. The reaction mixture was concentrated in vacuo, the residue diluted with water, and the resulting solid was filtered to give the product 2-(2-acetyl-hydrazinecarbonyl)-5-bromo-N-methyl-6-(N-methylmethylsulfonamido)benzofuran-3-carboxamide (146 mg, yield: 63%). $^1$H-NMR (DMSO-$d_6$, 400 MHz) δ 11.25 (br s, 1H), 10.22 (s, 1H), 9.68 (br s, 1H), 8.52 (s, 1H), 8.02 (s, 1H), 3.20 (s, 3H), 3.17 (s, 3H), 2.83 (d, J=4.4 Hz, 3H), 1.92 (s, 2H). MS (M+H)$^+$: 461/463.

Step 3 - Synthesis of 5-bromo-N-methyl-2-(5-methyl-1,3,4-oxadiazol-2-yl)-6-(N-methylmethylsulfonamido)benzofuran-3-carboxamide

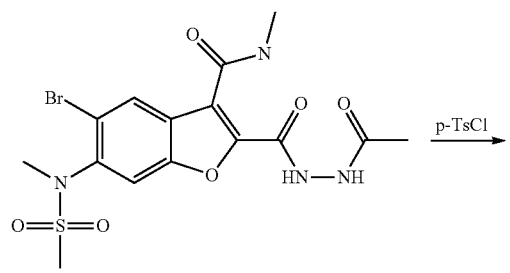

A mixture of compound 2-(2-acetylhydrazinecarbonyl)-5-bromo-N-methyl-6-(N-methylmethylsulfonamido)benzofuran-3-carboxamide (150 mg, 0.33 mmol), p-TsCl (124 mg, 0.66 mmol) and Et$_3$N (108 mg, 0.98 mmol) in CH$_2$Cl$_2$ (6 mL) was refluxed for 5 h. After concentration in vacuo, the residue was purified with prep-TLC (DCM:MeOH=100:1) to give the product 5-bromo-N-methyl-2-(5-methyl-1,3,4-oxadiazol-2-yl)-6-(N-methylmethylsulfonamido)benzofuran-3-carboxamide (146 mg, yield: 63%). $^1$H-NMR (CDCl$_3$, 400 MHz) δ 9.80 (br s, 1H), 8.96 (s, 1H), 7.77 (s, 1H), 3.36 (s, 3H), 3.13~3.06 (m, 6H), 2.75 (s, 3H). MS (M+H)$^+$: 443/445.

Step 4 - Synthesis of 5-(11-fluoro-6H-pyrido[2',3':5,6][1,3]oxazino[3,4-a]indol-2-yl)-N-methyl-2-(5-methyl-1,3,4-oxadiazol-2-yl)-6-(N-methylmethylsulfonamido)benzofuran-3-carboxamide

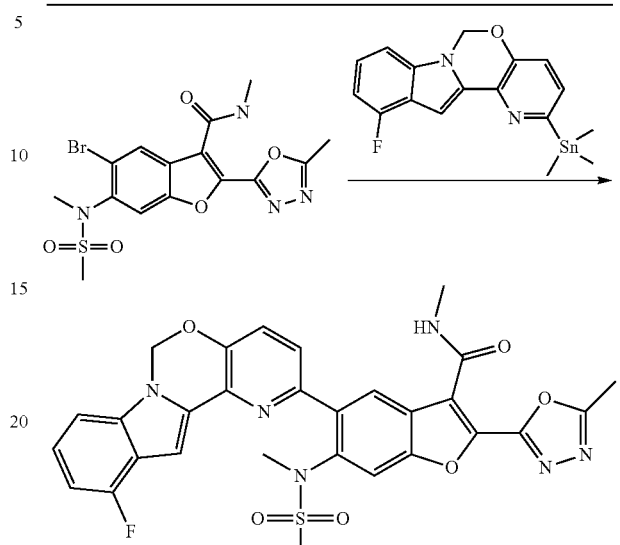

To a mixture of compound 5-bromo-N-methyl-2-(5-methyl-1,3,4-oxadiazol-2-yl)-6-(N-methylmethylsulfonamido)benzofuran-3-carboxamide (70 mg, 0.16 mmol), 11-fluoro-2-(trimethylstannyl)-6H-pyrido[2',3':5,6][1,3]oxazino[3,4-a]indole (95 mg, 0.24 mmol) and LiCl (20 mg, 0.47 mmol) in IPA (2 mL), chloro[(tricyclohexylphosphine)-2-(2'-aminobiphenyl)]palladium(II) (50 mg) was added under N$_2$ protection. After stirring at 100° C. overnight, the reaction mixture was concentrated in vacuo. The residue was purified by prep-TLC (DCM:MeOH=100:1) to give the product of 5-(11-fluoro-6H-pyrido[2',3':5,6][1,3]oxazino[3,4-a]indol-2-yl)-N-methyl-2-(5-methyl-1,3,4-oxadiazol-2-yl)-6-(N-methylmethylsulfonamido)benzofuran-3-carboxamide (20 mg, yield: 21%). $^1$H-NMR (CDCl$_3$, 400 MHz) δ 9.81 (br s, 1H), 8.81 (s, 1H), 7.77 (s, 1H), 7.55~7.46 (m, 2H), 7.25~7.18 (m, 2H), 7.13 (s, 1H), 6.89~6.80 (m, 1H), 6.01 (s, 2H), 3.41 (s, 3H), 3.09 (d, J=4.4 Hz, 3H), 2.76 (s, 3H), 2.68 (s, 3H). MS (M+H)$^+$: 603.

Example 59

5-(11-fluoro-6H-pyrido[2',3':5,6][1,3]oxazino[3,4-a]indol-2-yl)-2-(1-(methoxyimino)ethyl)-N-methyl-6-(N-methylmethylsulfonamido)benzofuran-3-carboxamide

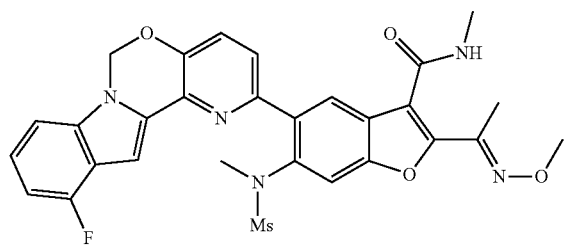 [SMILES: CNC(=O)c1c(/C(C)=N/OC)oc2cc(N(C)S(C)(=O)=O)c(-c3ccc4c(n3)-c3cc5c(F)cccc5n3CO4)cc12]

Step 1 - Synthesis of 2-acetyl-6-amino-5-bromo-N-methylbenzofuran-3-carboxamide

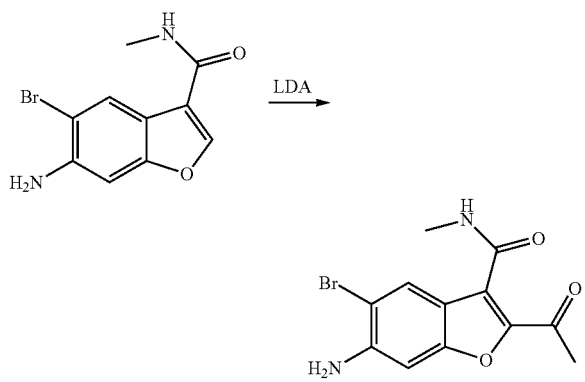

To a solution of diisopropylamine (3.76 g, 37.1 mmol) in THF (25 mL) was slowly added a solution of n-BuLi (2.5 mol/L in hexane) (16.5 mL, 40.5 mmol) under $N_2$ at −78° C. and the resulting solution was stirred at −78° C. for 30 minutes. A solution of compound 6-amino-5-bromo-N-methylbenzofuran-3-carboxamide (2 g, 7.43 mmol) in THF (50 mL) was slowly added to the fresh lithium diisopropylamide at −78° C. and stirred for another one hour. To the resulting mixture was added N-methoxy-N-methylacetamide (3.83 g, 37.16 mmol) at −78° C. and stirred for another one hour. The reaction was quenched with saturated $NH_4Cl$ at −78° C. and the mixture was slowly warmed to room temperature. Water was added and the mixture extracted with EtOAc. The organic layers were washed with brine, dried over $Na_2SO_4$ and concentrated in vacuo to give the crude product. The crude product was purified by column chromatography to give compound 2-acetyl-6-amino-5-bromo-N-methylbenzofuran-3-carboxamide (700 mg, yield: 30%). $^1$H-NMR (CDCl$_3$, 400 MHz) δ 10.00 (s, 1H), 8.76 (s, 1H), 6.86 (s, 1H), 4.54 (s, 2H), 3.00 (d, J=4.8 Hz, 3H), 2.70 (s, 3H). MS (M+H)$^+$: 311/313.

Step 2 - Synthesis of 2-acetyl-5-bromo-N-methyl-6-(methylsulfonamido)benzofuran-3-carboxamide

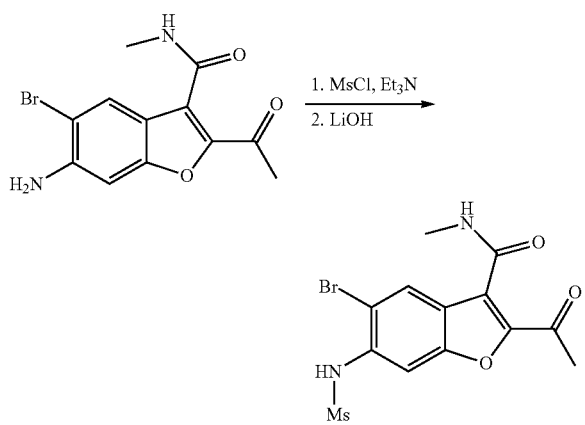

To a mixture of 2-acetyl-6-amino-5-bromo-N-methylbenzofuran-3-carboxamide (500 mg, 1.61 mmol) and triethylamine (650 mg, 6.43 mmol) in THF (20 mL) was added MsCl (406 mg, 3.54 mmol) dropwise at 0° C. under $N_2$. The mixture was stirred at room temperature for 1 hour. The mixture was quenched with $H_2O$ and extracted with EtOAc, and then the combined organic layers were washed with brine, dried over $Na_2SO_4$, and concentrated in vacuo to give the crude product. The crude product was dissolved in THF (20 mL) and then a solution of LiOH/$H_2O$ (200 mg/6 mL) was added. The mixture was stirred at room temperature for 1 hour, then water was added to the mixture and extracted with EtOAc. The combined organic layers were washed with brine, dried over $Na_2SO_4$, and concentrated in vacuo to give the crude product. The crude product was purified by column chromatography to give compound 2-acetyl-5-bromo-N-methyl-6-(methylsulfonamido)benzofuran-3-carboxamide (280 mg, yield: 44.8%). $^1$H-NMR (CDCl$_3$, 400 MHz) δ 9.83 (s, 1H), 8.97 (s, 1H).7.91 (s, 1H), 7.07 (s, 1H), 3.06 (s, 3H), 3.02 (d, J=4.8 Hz, 3H), 2.77 (s, 3H). MS (M+H)$^+$: 389/391.

Step 3 - Synthesis of 2-acetyl-5-bromo-N-methyl-6-(N-methylmethylsulfonamido)benzofuran-3-carboxamide

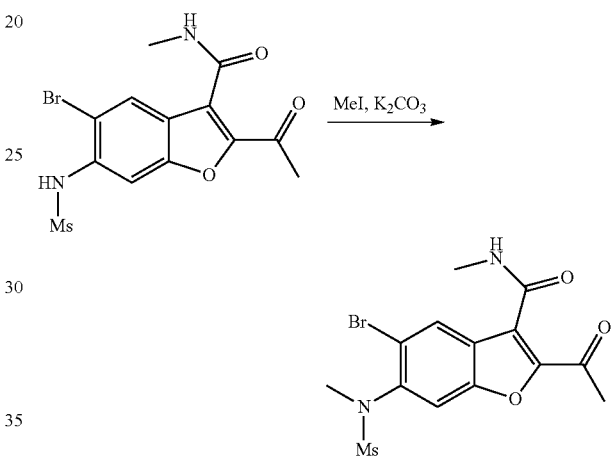

To a solution of 2-acetyl-5-bromo-N-methyl-6-(methylsulfonamido)benzofuran-3-carboxamide (150 mg, 0.38 mmol) in DMF (3 mL) was added $K_2CO_3$ (160 mg, 1.16 mmol) and MeI (164 mg, 1.16 mmol). The mixture was heated at 60° C. for 1 hour, concentrated in vacuo to remove DMF and extracted with EtOAc. The combined organic layers were washed with brine, dried over $Na_2SO_4$, and concentrated to give crude product. The crude product was purified by column chromatography to give 2-acetyl-5-bromo-N-methyl-6-(N-methylmethylsulfonamido)benzofuran-3-carboxamide (70 mg, yield: 45%). $^1$H-NMR (CDCl$_3$, 400 MHz) δ 9.73 (s, 1H), 9.01 (s, 1H), 7.78 (s, 1H), 3.35 (s, 3H), 3.09 (s, 3H), 3.02 (d, J=4.8 Hz, 3H), 2.77 (s, 3H). MS (M+H)$^+$: 403/405.

Step 4 - Synthesis of 2-acetyl-N-methyl-6-(N-methylmethylsulfonamido)-5-(4,4,5,5-tetramethyl-1,3,2-dioxaborolan-2-yl)benzofuran-3-carboxamide

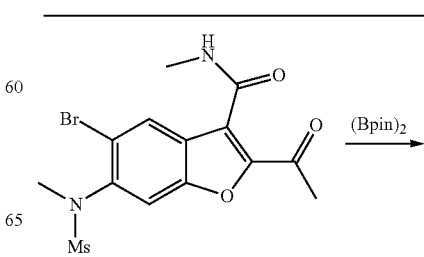

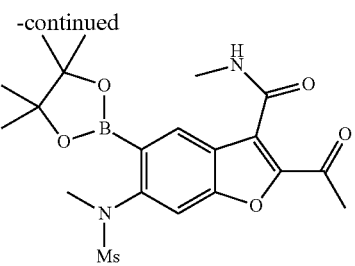

To a degassed solution of 2-acetyl-5-bromo-N-methyl-6-(N-methylmethylsulfonamido)benzofuran-3-carboxamide (420 mg, 1.04 mmol), KOAc (306 mg, 3.12 mmol) and 4,4,4',4',5,5,5',5'-octamethyl-2,2'-bi(1,3,2-dioxaborolane) (1.06 g, 4.17 mmol) in 1,4-dioxane (10 mL) was added Pd(dppf)Cl$_2$ (50 mg) under N$_2$ protection. The mixture was stirred at 90° C. for 4 hours. The mixture was filtered through a celite pad, and the residue was concentrated to give crude product. The residue was purified by column chromatography (PE: EA=3:1) to give 2-acetyl-N-methyl-6-(N-methylmethylsulfonamido)-5-(4,4,5,5-tetramethyl-1,3,2-dioxaborolan-2-yl)benzofuran-3-carboxamide (220 mg, yield: 47%). $^1$H-NMR (CDCl$_3$, 400 MHz) δ 9.74 (s, 1H), 9.15 (s, 1H), 7.66 (s, 1H), 3.36 (s, 3H), 3.03 (d, J=4.8 Hz, 3H), 2.98 (s, 3H), 2.77 (s, 3H), 1.36 (s, 12H). MS (M+H)$^+$: 451.

Step 5 - Synthesis of 2-acetyl-5-(11-fluoro-6H-pyrido[2',3':5,6][1,3]oxazino[3,4-a]indol-2-yl)-N-methyl-6-(N-methylmethylsulfonamido)benzofuran-3-carboxamide

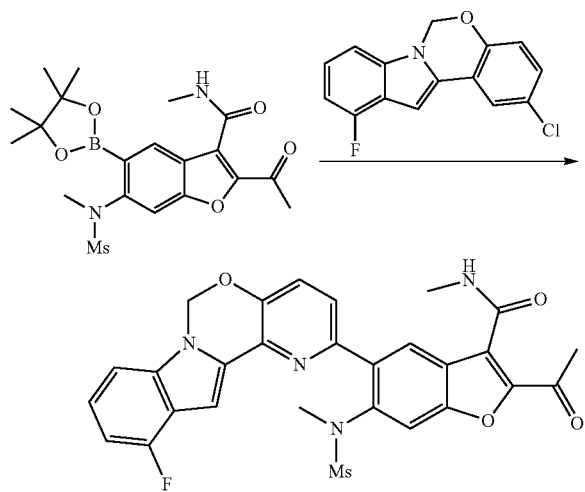

To a solution of compound 2-acetyl-N-methyl-6-(N-methylmethylsulfonamido)-5-(4,4,5,5-tetramethyl-1,3,2-dioxaborolan-2-yl)benzofuran-3-carboxamide (150 mg, 0.33 mmol), 2-chloro-11-fluoro-6H-benzo[5,6][1,3]oxazino[3,4-a]indole (91 mg, 0.33 mmol) and Cs$_2$CO$_3$ (215 mg, 0.66 mmol) in 1,4-dioxane (3 mL) and water (0.01 mL) was added Pd(dtbpf)Cl$_2$(20 mg) under nitrogen. The mixture was heated at 90° C. for 3 hours and filtered through the celite pad. The filtrate was extracted with EtOAc, then the combined organic phase was washed with brine, dried over Na$_2$SO$_4$ and concentrated in vacuo to give the compound 2-acetyl-5-(11-fluoro-6H-pyrido[2',3':5,6][1,3]oxazino[3,4-a]indol-2-yl)-N-methyl-6-(N-methylmethylsulfonamido)benzofuran-3-carboxamide (50 mg, yield: 27%) by the prep-TLC (PE: EtOAc=1:1). MS (M+H)$^+$: 563.

Step 6 - Synthesis of 5-(11-fluoro-6H-pyrido[2',3':5,6][1,3]oxazino[3,4-a]indol-2-yl)-2-(1-(methoxyimino)ethyl)-N-methyl-6-(N-methylmethylsulfonamido)benzofuran-3-carboxamide

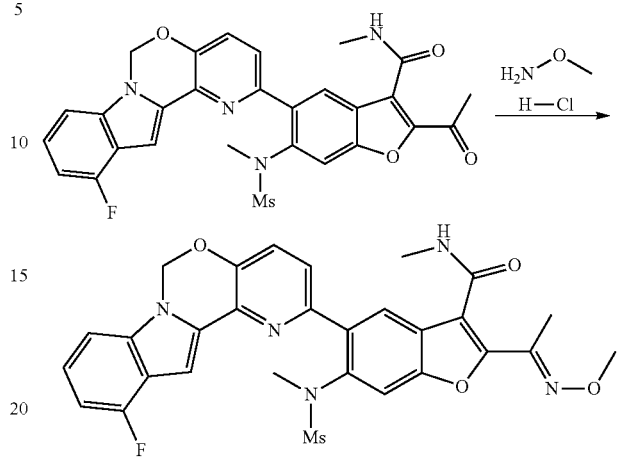

To a solution compound 2-acetyl-5-(11-fluoro-6H-pyrido[2',3':5,6][1,3]oxazino[3,4-a]indol-2-yl)-N-methyl-6-(N-methylmethylsulfonamido)benzofuran-3-carboxamide (50 mg, 0.088 mmol) in ethanol (1.5 mL) was added O-methylhydroxylamine hydrochloride (25 mg, 0.26 mmol) and 2 drops pyridine. The resulting mixture was stirred at 70° C. for 2 hours. The solvent was removed under reduced pressure and the residue was purified by prep-HPLC to give the product of (E)-5-(11-fluoro-6H-pyrido[2',3':5,6][1,3]oxazino[3,4-a]indol-2-yl)-2-(1-(methoxyimino)ethyl)-N-methyl-6-(N-methylmethylsulfonamido)benzofuran-3-carboxamide (20 mg, yield: 40%). $^1$H-NMR (CDCl$_3$, 400 MHz) δ 9.56 (s, 1H), 8.65 (s, 1H), 7.67 (s, 1H), 7.48 (dd, J=10 Hz, 2H), 7.18~7.23 (m, 2H), 7.10 (d, J=8.0 Hz, 1H), 6.84 (t, J=8.0 Hz, 1H), 5.99 (s, 2H), 4.12 (s, 3H), 3.41 (s, 3H), 2.99 (d, J=4.8 Hz, 3H), 2.66 (s, 3H), 2.41 (s, 3H). MS (M+H)$^+$: 592.

Example 60

Measuring Compound Inhibitory Potency

Measurement of inhibition by compounds was performed using the HCV replicon system. Several different replicons encoding different HCV genotypes or mutations were used. In addition, potency measurements were made using different formats of the replicon assay, including different ways of measurements and different plating formats. See Jan M. Vrolijk et al., *A replicons-based bioassay for the measurement of interferons in patients with chronic hepatitis C*, 110 J. VIROLOGICAL METHODS 201 (2003); Steven S. Carroll et al., *Inhibition of Hepatitis C Virus RNA Replication by 2'-Modified Nucleoside Analogs*, 278(14) J. BIOLOGICAL CHEMISTRY 11979 (2003). However, the underlying principles are common to all of these determinations, and are outlined below.

Stable neomycin phosphotransferase encoding replicons-harboring cell lines were used, so all cell lines were maintained under G418 selection prior to the assay. Potency was determined using a cell ELISA assay with an antibody to the replicons encoded NS3/4a protease. See Caterina Trozzi et al., *In Vitro Selection and Characterization of Hepatitis C Virus Serine Protease Variants Resistant to an Active-Site Peptide Inhibitor*, 77(6) J. Virol. 3669 (2003). To initiate an assay, replicon cells were plated in the presence of a dilution series of test compound in the absence of G418. Typically, the assays were performed in a 96-well plate formate for manual operation, or a 384-well plate format for automated assay. Replicon cells and compound were incubated for 96 hours. At the end of the assay, cells were washed free of media and compound, and the cells were then lysed. RNA was quantified indirectly through detection of replicon-encoded NS3/4A protein levels, through an ELISA-based assay with an antibody specific for NS3/4A. $IC_{50}$ determinations were calculated as a percentage of a DMSO control by fitting the data to a four-parameter fit function and the data obtained is provided in the table below.

Data for selected compounds of the present invention was obtained for genotypes 1a and 1b using this method and is provided in the table below:

| Compound# | 1a $IC_{50}$ (nM) | 1b $IC_{50}$ (nM) |
|---|---|---|
| 1 | 11 | 14 |
| 2 | 13 | 12 |
| 3 | 3.6 | 5.8 |
| 4 | 3.0 | 6.1 |
| 5 | 4.4 | 7.5 |
| 6 | 17 | 12 |
| 7 | 8.5 | 13 |
| 8 | 6.3 | 4.5 |
| 9 | 2.5 | 3.4 |
| 10 | 15 | 13 |
| 11 | 7.2 | 8.4 |
| 12 | 2.7 | 1.8 |
| 13 | 16 | 9.4 |
| 14 | 9.1 | 18 |
| 15 | 23 | 34 |
| 16 | 26 | 8.5 |
| 17 | 324 | 393 |
| 18 | 57 | 29 |
| 19 | 35 | 13 |
| 20 | 3.7 | 2.5 |
| 21 | 2.4 | 2.8 |
| 22 | 3.5 | 2.5 |
| 23 | 2.8 | 2.9 |
| 24 | 1.7 | 1.4 |
| 25 | 3.0 | 5.0 |
| 26 | 118 | 108 |
| 27 | 23 | 34 |
| 28 | 9.0 | 6.9 |
| 29 | 13 | 25 |
| 30 | 11 | 25 |
| 31 | 5.9 | 3.9 |
| 32 | 36 | 14 |
| 33 | 50 | 2.5 |
| 34 | 15 | 14 |
| 35 | 2.8 | 3.1 |
| 36 | 14 | 20 |
| 37 | 2.2 | 3.0 |
| 38 | 3.5 | 2.7 |
| 39 | 48 | 67 |
| 40 | 16 | 22 |
| 41 | 82 | 22 |
| 42 | 85 | 35 |
| 43 | 21 | 50 |
| 44 | 6.2 | 8.3 |
| 45 | 6.1 | 6.4 |
| 46 | 15 | 13 |
| 47 | 5.9 | 8.8 |
| 48 | 28 | 34 |
| 49 | 27 | 22 |
| 50 | 22 | 38 |
| 51 | 8.3 | 15 |
| 52 | 52 | 23 |
| 53 | 33 | 30 |
| 54 | 4.3 | 7.1 |
| 55 | 4.0 | 6.4 |
| 56 | 5.0 | 11 |
| 57 | 232 | 135 |
| 58 | 8.1 | 7.9 |
| 59 | 34 | 13 |

It will be appreciated that various of the above-discussed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

What is claimed is:

1. A compound having the formula:

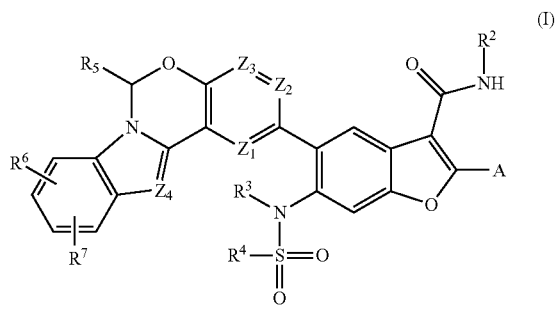

(I)

or a pharmaceutically acceptable salt thereof,
wherein:
$Z_1$, $Z_2$ and $Z_3$ are independently CH or N;
$Z_4$ is CH or N;
A is $C_3$-$C_6$ cycloalkyl, $C_2$-$C_4$ alkenyl, $C_3$-$C_6$ cycloalkenyl, 4- to 6-membered monocyclic heterocycloalkyl, 4- to 6-membered monocyclic heterocycloalkenyl, —C(=O)NR$^a$R$^b$, —C(=O)— (4- to 6-membered monocyclic heterocycloalkyl), —C(R$^c$)=NOR$^d$, or HetA, wherein cycloalkyl is optionally substituted by 1 or 2 substituents selected from $C_1$-$C_6$ alkyl and halo, wherein HetA is optionally substituted by 1 or 2 ring substituents R', and wherein the 4- to 6-membered monocyclic heterocycloalkyl is optionally substituted with oxo;
HetA is a 5- or 6-membered aromatic monocyclic ring with 1, 2 or 3 heteroatom ring atoms independently selected from N, O and S;
R$^a$, R$^b$, R$^c$, R$^d$ are independently selected from H and $C_1$-$C_6$ alkyl;
each occurrence of R$^1$ is independently selected from halo, —OH, $C_1$-$C_6$ alkyl, $C_1$-$C_6$ alkoxy, $C_1$-$C_6$ haloalkyl, —O—($C_1$-$C_6$ alkyl), —O—($C_1$-$C_6$ haloalkyl), oxo, cyano, and —O— phenyl-F;
$R^2$ is hydrogen, $C_1$-$C_6$ alkyl or —O($C_1$-$C_6$ alkyl);
$R^3$ is hydrogen or $C_1$-$C_6$ alkyl;
$R^4$ is $C_1$-$C_6$ alkyl or —O($C_1$-$C_6$ alkyl);
$R^5$ is hydrogen or $C_1$-$C_6$ hydroxyalkyl;
$R^6$ and $R^7$ are independently hydrogen, halo, cyano or $C_1$-$C_4$ alkyl.

2. The compound of claim 1, wherein $R^2$ and $R^4$ are independently $C_1$-$C_6$ alkyl.

3. The compound of claim 2, wherein $R^2$, $R^3$ and $R^4$ are methyl.

4. The compound of claim 3, wherein no more than one of $R^6$ and $R^7$ are halo.

5. The compound of claim 4, wherein each halo is F.

6. The compound of claim 5, wherein $R^5$ is hydrogen or —CH$_2$OH.

7. The compound of claim 1, or a pharmaceutically acceptable salt thereof, having the formula:

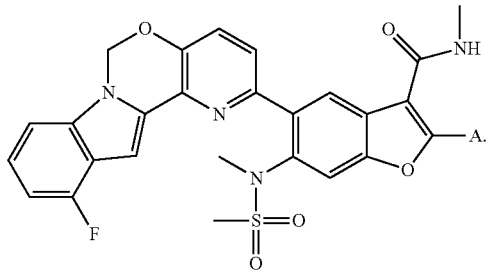

(Ia)

8. The compound of claim 3, wherein A is
C₃-C₆ cycloalkyl; C₂-C₄ alkenyl; C₃-C₆ cycloalkenyl; 4- to 6-membered monocyclic heterocycloalkyl; 4- to 6-membered monocyclic heterocycloalkenyl optionally substituted with 1 or 2 substituents independently selected from C₁-C₆ alkyl, C₁-C₆ alkoxy, C₁-C₆ haloalkyl, oxo, halo, and —O—C₁-C₆ haloalkyl; or a 5-6 membered aromatic monocyclic ring with 1, 2 or 3 heteroatom ring atoms selected from N, O, and S wherein the 5-6 membered aromatic monocyclic ring is optionally substituted with 1 or 2 substituents independently selected from C₁-C₆ alkyl, C₁-C₆ alkoxy, C₁-C₆ haloalkyl, oxo, halo, —O-4-F-phenyl, and —O—C₁-C₆ haloalkyl.

9. The compound of claim 8, wherein A is cyclopropyl,

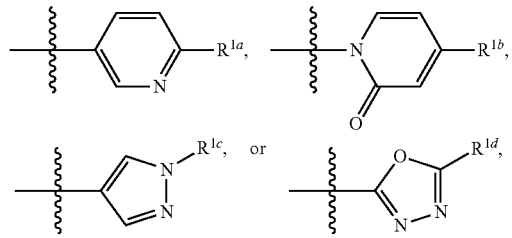

wherein R¹ᵃ is F, methyl, ethyl, methoxy, ethoxy, —O-isopropyl, —OCHF₂, —OCH₂CF₃, —CHF₂, or —CF₃, R¹ᵇ is hydrogen or methyl, R¹ᶜ is methyl, ethyl, or isopropyl, and R¹ᵈ is methyl or ethyl.

10. The compound of claim 9, wherein A is cyclopropyl,

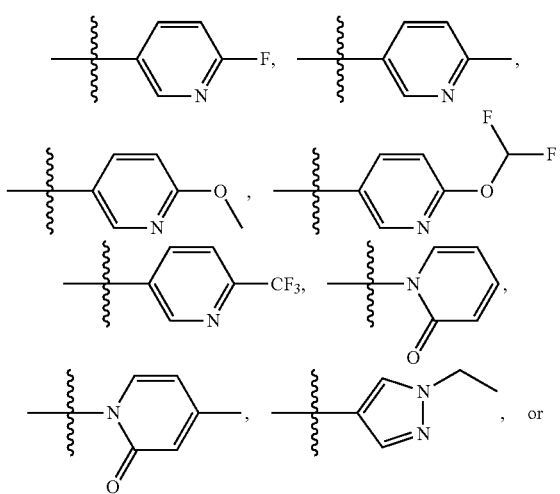

-continued

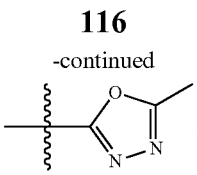

11. The compound of claim 1 which is any one of

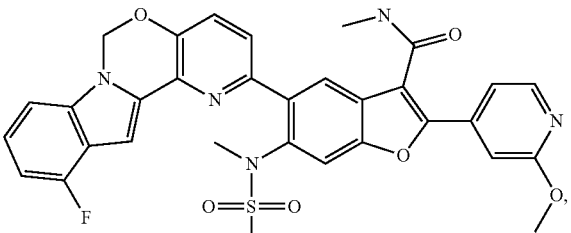

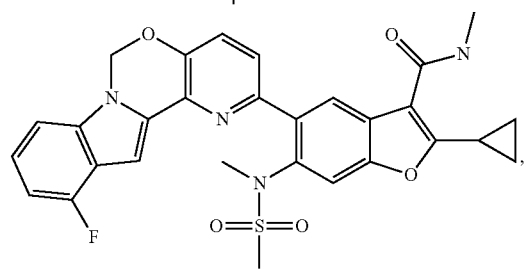

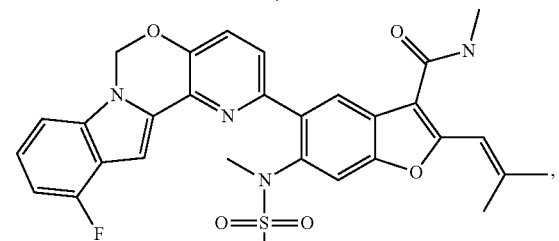

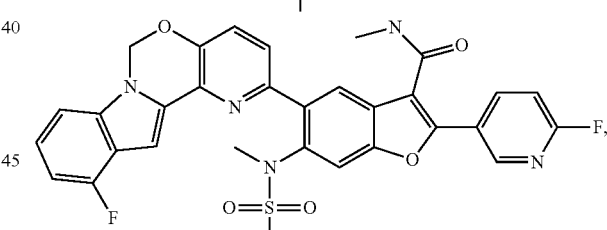

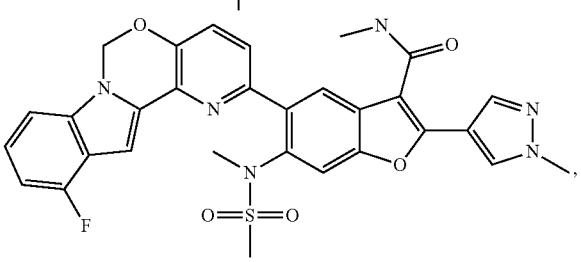

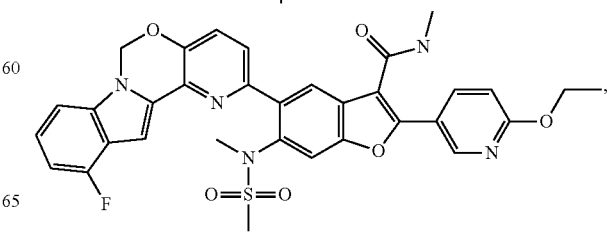

117
-continued
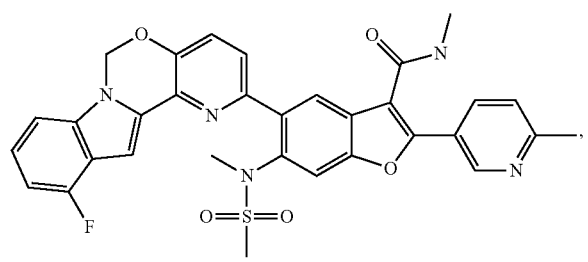
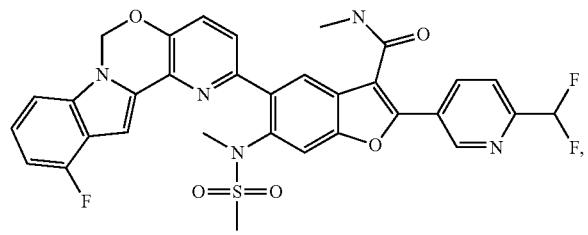
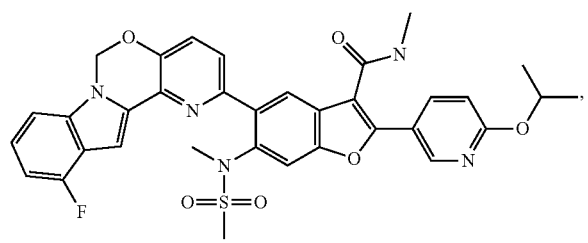
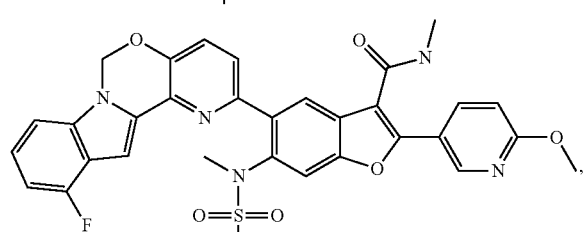
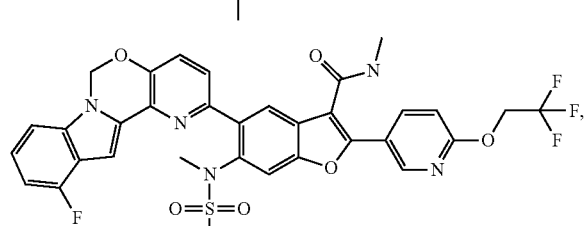
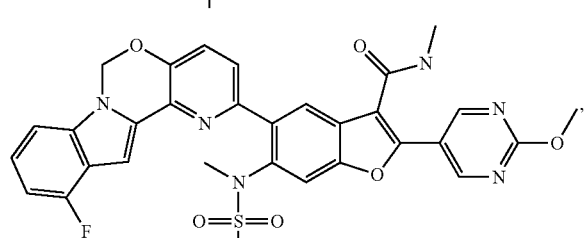
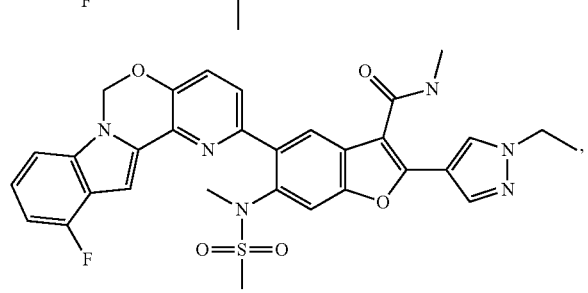
118
-continued
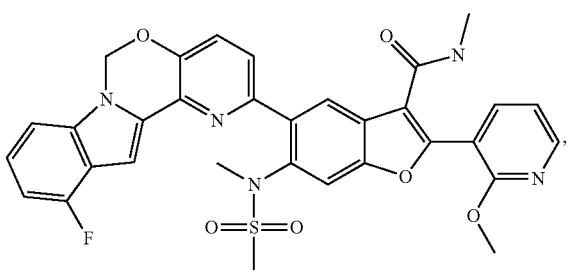
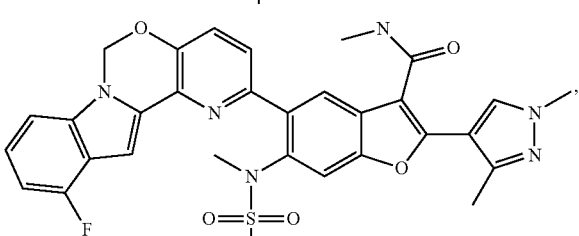
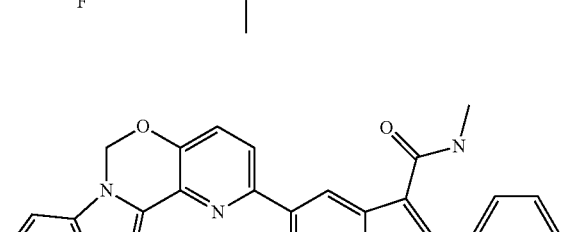
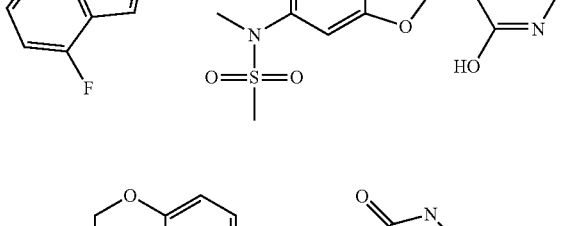
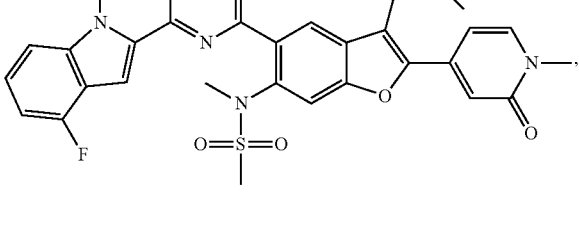
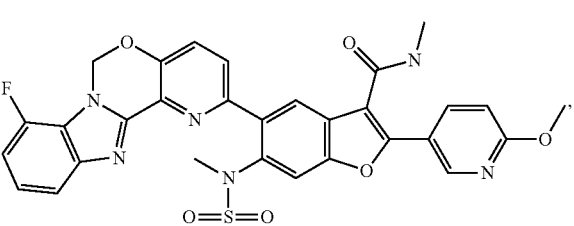
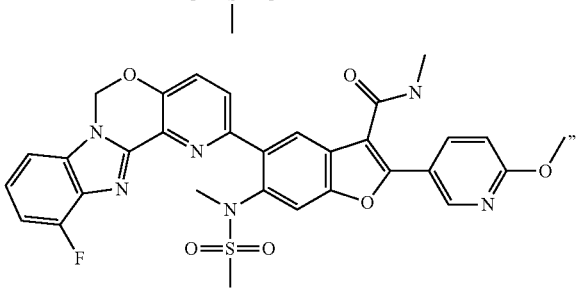

119
-continued
120
-continued
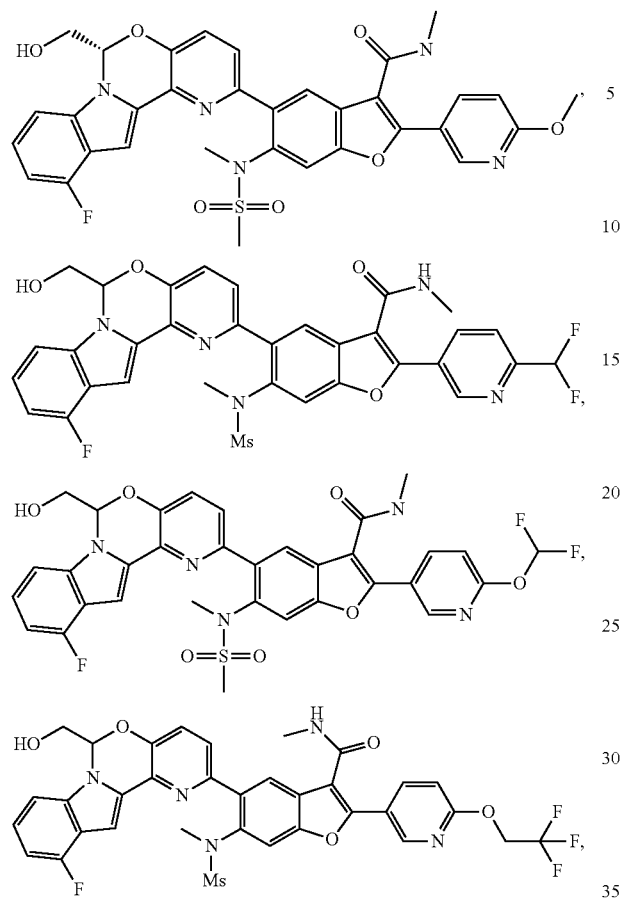
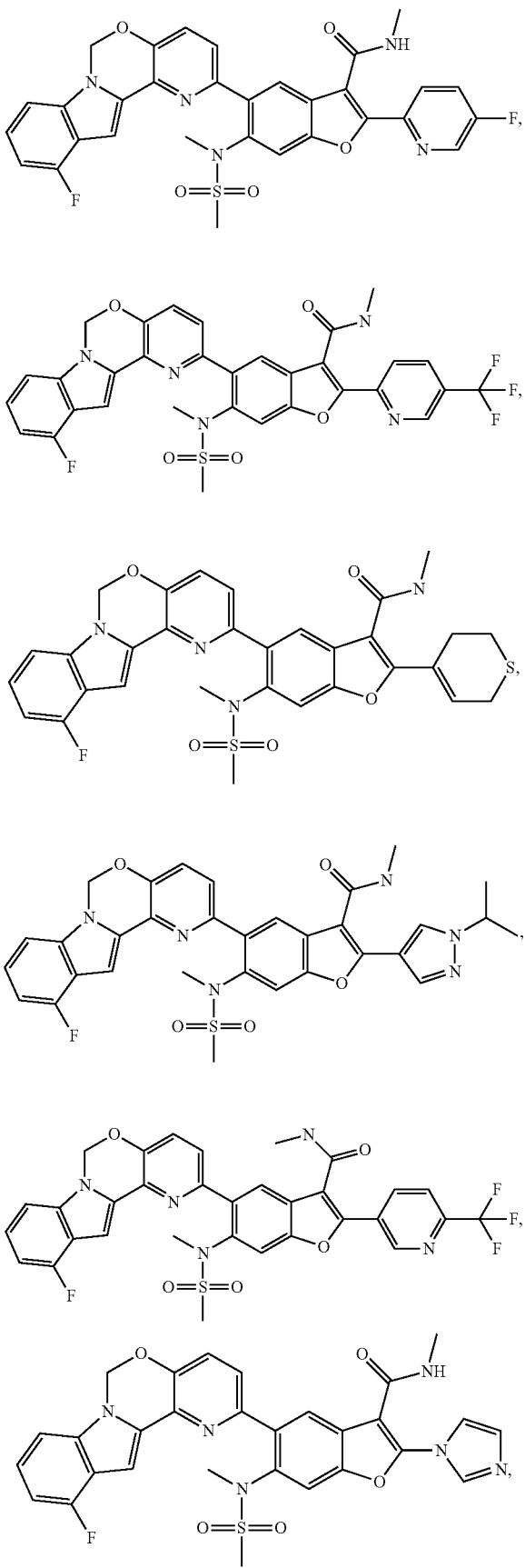

121
-continued
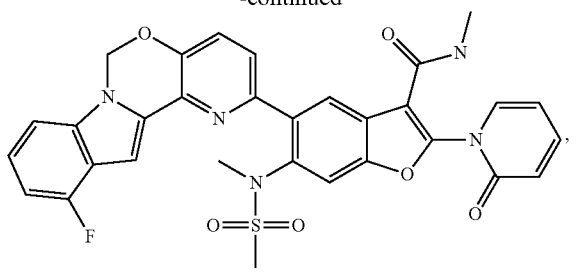
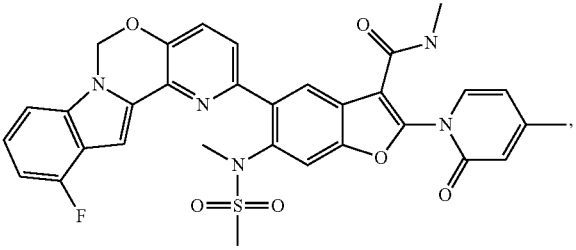
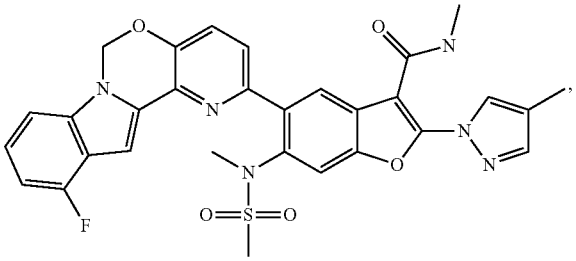
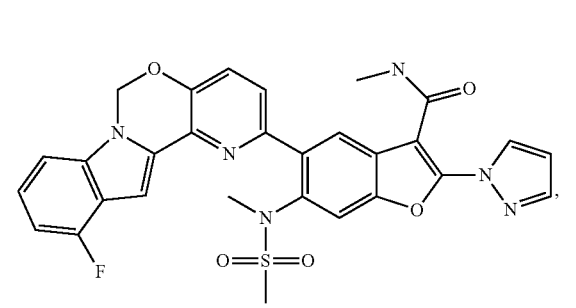
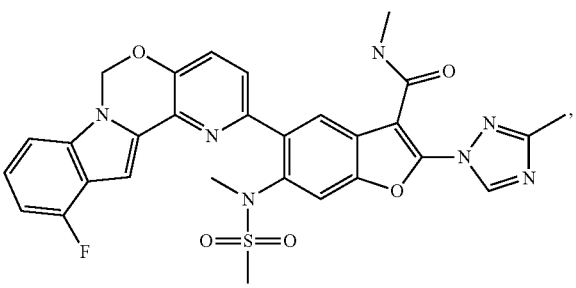
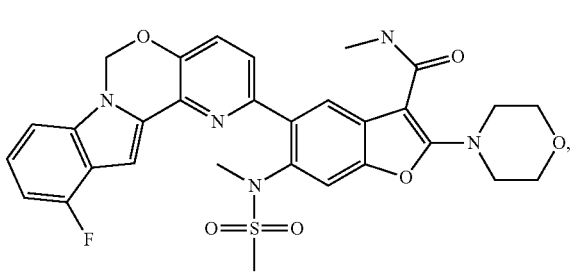
122
-continued
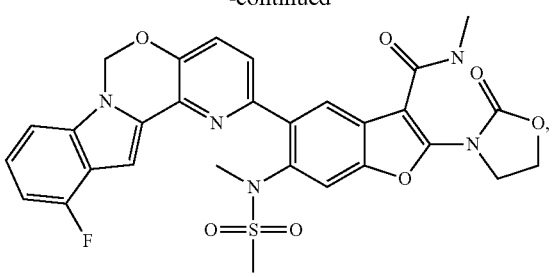
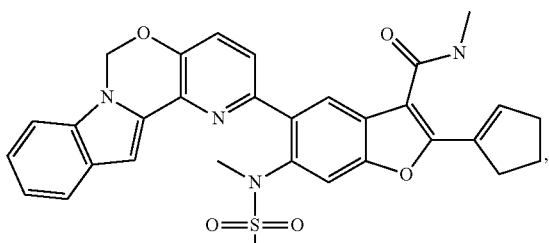
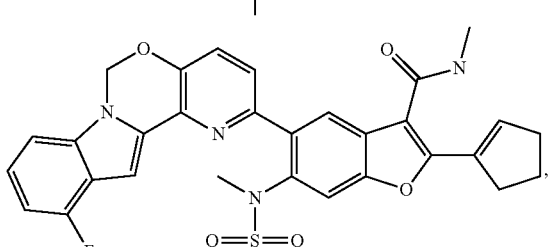
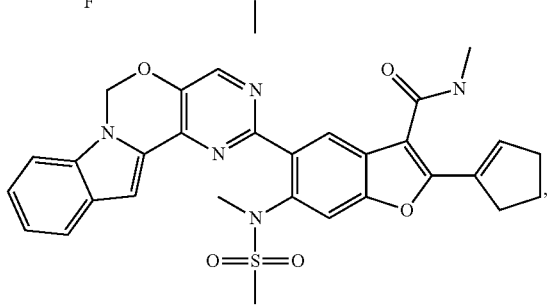
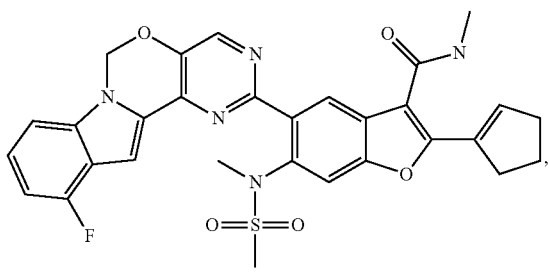
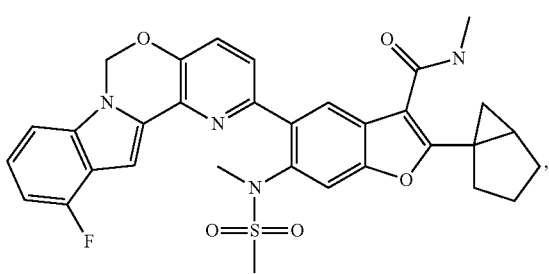

123
-continued
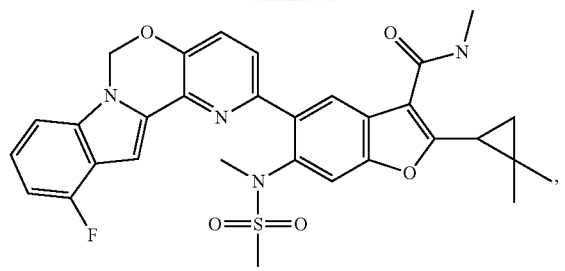
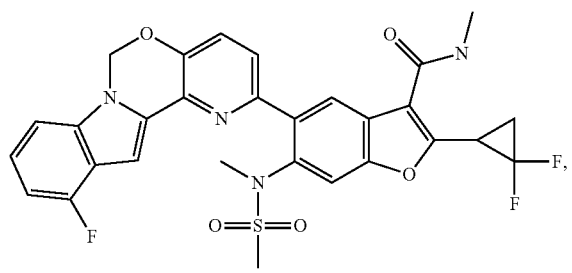
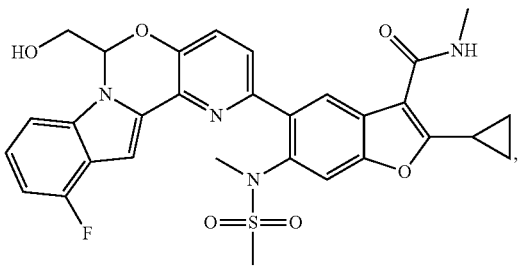
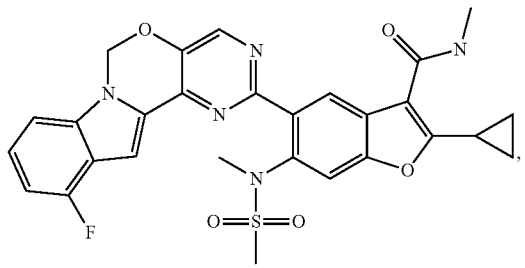
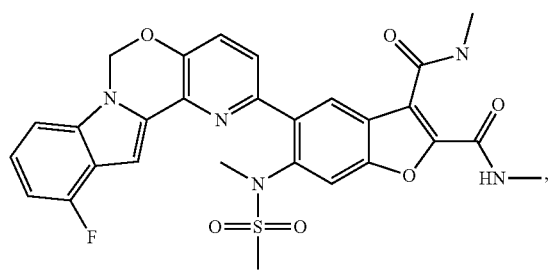
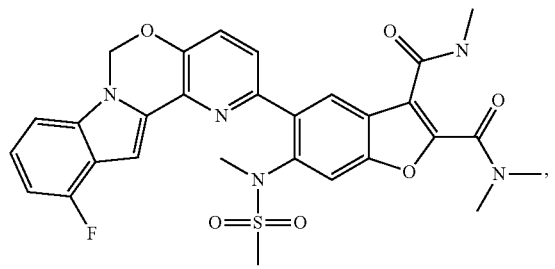
124
-continued
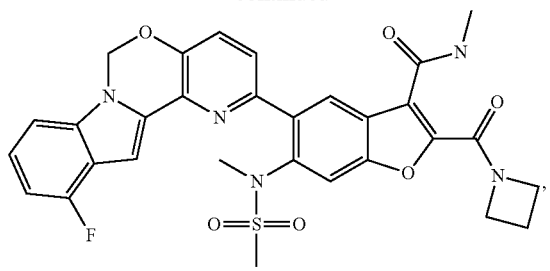
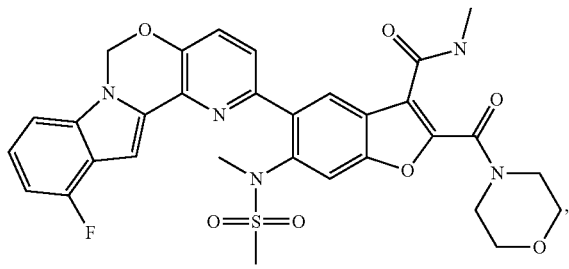
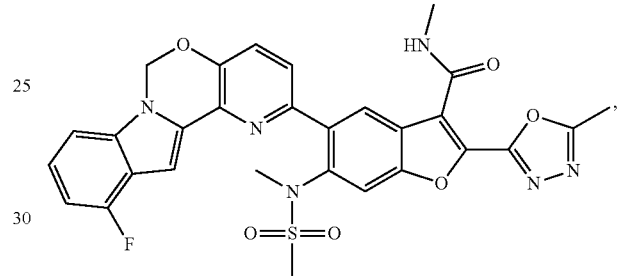
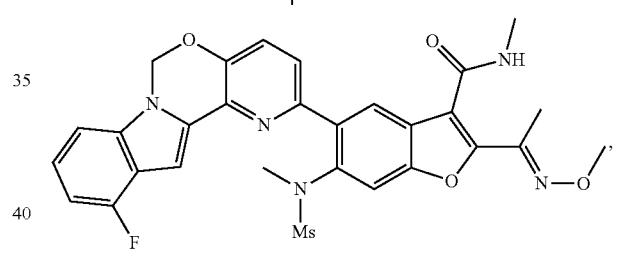
or a pharmaceutically acceptable salt thereof.
12. The compound of claim 1 which is any one of
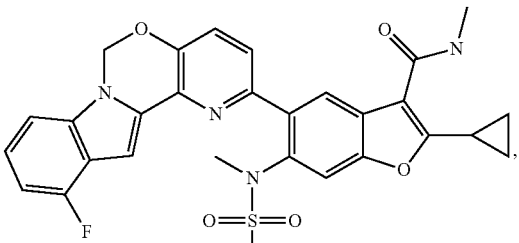
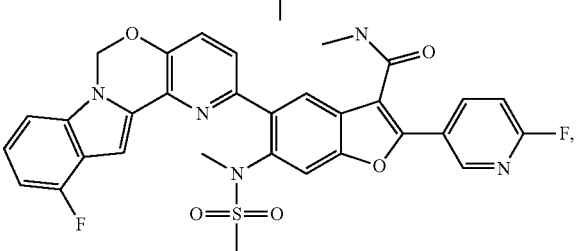

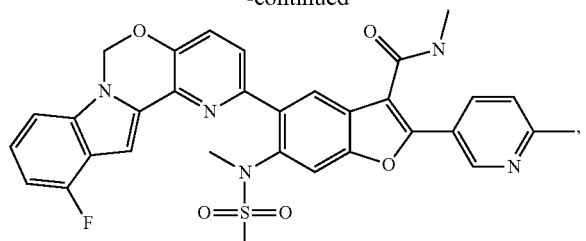

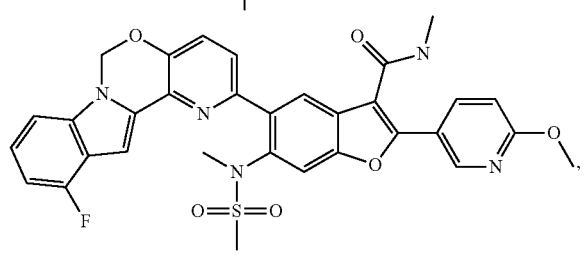

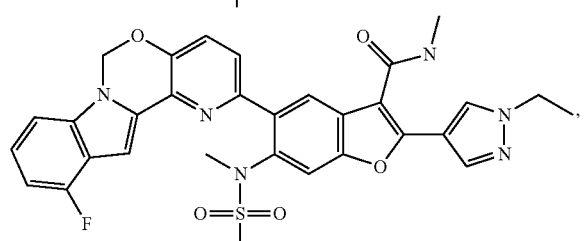

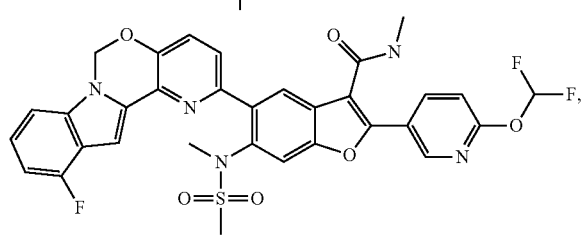

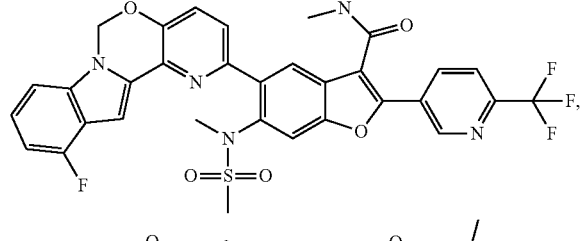

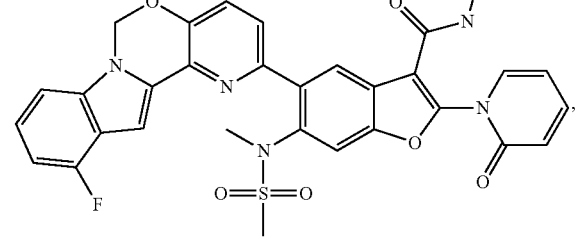

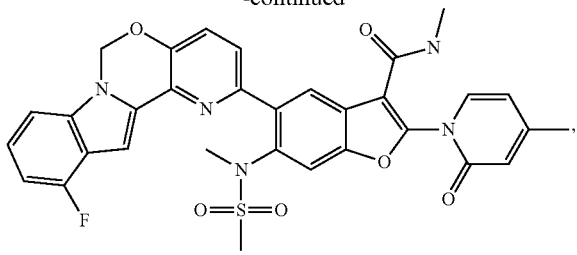

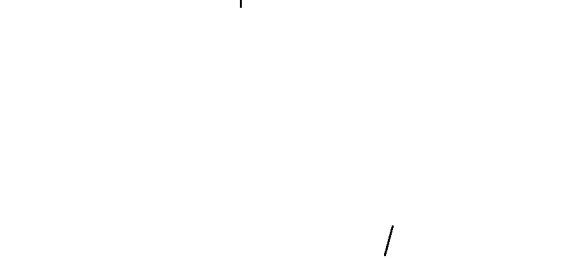

or a pharmaceutically acceptable salt thereof.

13. A pharmaceutical composition comprising (i) a pharmaceutically acceptable carrier and (ii) an effective amount of the compound of claim 1 or a pharmaceutically acceptable salt thereof.

14. The pharmaceutical composition of claim 13, further comprising a second therapeutic agent selected from the group consisting of HCV antiviral agents, immunomodulators, and anti-infective agents.

15. The pharmaceutical composition of claim 14, wherein the second therapeutic agent is selected from the group consisting of HCV NS3 and NS3/4A protease inhibitors, HCV NS5A inhibitors and HCV NS5B polymerase inhibitors.

16. A method of treating a patient infected with HCV, the method comprising administering to the patient the compound of claim 1, or a pharmaceutically acceptable salt thereof, in an amount effective to prevent and/or treat infection by HCV in the patient.

17. The method of claim 16, further comprising administering to said patient an effective amount of at least one second therapeutic agent selected from the group consisting of HCV NS3 and NS3/4A protease inhibitors, HCV NS5A inhibitors and HCV NS5B polymerase inhibitors.

* * * * *